United States Patent
Bristol et al.

(10) Patent No.: US 11,638,699 B2
(45) Date of Patent: May 2, 2023

(54) INTESTINAL ALKALINE PHOSPHATASE FORMULATIONS

(71) Applicant: Theriva Biologics, Inc., Rockville, MD (US)

(72) Inventors: Andrew Bristol, Rockville, MD (US); Ray Stapleton, Rockville, MD (US); Michael Kaleko, Rockville, MD (US); Christian Furlan Freguia, Rockville, MD (US); Steven Hubert, Rockville, MD (US); Cristina Freire, Rockville, MD (US); James Gubbins, Rockville, MD (US)

(73) Assignee: Theriva Biologics, Inc., Rockville, MD (US)

( * ) Notice: Subject to any disclaimer, the term of this patent is extended or adjusted under 35 U.S.C. 154(b) by 0 days.

(21) Appl. No.: 16/982,236

(22) PCT Filed: Mar. 20, 2019

(86) PCT No.: PCT/US2019/023142
§ 371 (c)(1),
(2) Date: Sep. 18, 2020

(87) PCT Pub. No.: WO2019/183208
PCT Pub. Date: Sep. 26, 2019

(65) Prior Publication Data
US 2021/0030686 A1    Feb. 4, 2021

Related U.S. Application Data

(60) Provisional application No. 62/645,421, filed on Mar. 20, 2018.

(51) Int. Cl.
*A61K 9/28* (2006.01)
*A61K 9/19* (2006.01)
*A61K 9/20* (2006.01)
*A61K 38/46* (2006.01)
*C12N 9/16* (2006.01)
*C12N 15/63* (2006.01)
*C12N 15/52* (2006.01)

(52) U.S. Cl.
CPC ............. *A61K 9/2846* (2013.01); *A61K 9/19* (2013.01); *A61K 9/2009* (2013.01); *A61K 9/2013* (2013.01); *A61K 9/2018* (2013.01); *A61K 9/2027* (2013.01); *A61K 9/2054* (2013.01); *A61K 9/2095* (2013.01); *A61K 9/2866* (2013.01); *A61K 9/2886* (2013.01); *A61K 9/2893* (2013.01); *A61K 38/465* (2013.01); *C12N 9/16* (2013.01); *C12Y 301/03001* (2013.01); *C12N 15/52* (2013.01); *C12N 15/63* (2013.01)

(58) Field of Classification Search
None
See application file for complete search history.

(56) References Cited

U.S. PATENT DOCUMENTS

| 5,773,226 A | 6/1998 | Millan |
|---|---|---|
| 5,821,095 A | 10/1998 | Hattori et al. |
| 5,891,699 A | 4/1999 | Boulain et al. |
| 5,948,410 A | 9/1999 | Van Scharrenburg et al. |
| 6,290,952 B1 | 9/2001 | Poelstra et al. |
| 6,406,899 B1 | 6/2002 | Hoelke et al. |
| 6,638,531 B1 | 10/2003 | Amerongen et al. |
| 6,649,390 B1 | 11/2003 | Sheng et al. |
| 6,686,392 B1 | 2/2004 | Avram et al. |
| 6,756,063 B2 | 6/2004 | Kiss |
| 6,793,928 B1 | 9/2004 | van Scharrenburg et al. |
| 6,884,602 B2 | 4/2005 | Mueller et al. |
| 6,905,689 B2 | 6/2005 | Schneidinger et al. |
| 7,011,965 B2 | 3/2006 | Kiss |
| 7,014,852 B2 | 3/2006 | Kiss |
| 7,048,914 B2 | 5/2006 | Kiss |
| 7,060,677 B1 | 6/2006 | Van Berkel et al. |
| 7,312,198 B2 | 12/2007 | Kiss |
| 7,374,754 B2 | 5/2008 | Kiss |
| 7,423,029 B1 | 9/2008 | Kiss |
| 7,501,116 B2 | 3/2009 | Kiss |
| 7,557,081 B2 | 7/2009 | Kiss |
| 7,589,083 B2 | 9/2009 | Kiss |
| 7,655,620 B2 | 2/2010 | Kiss |
| 7,695,714 B2 | 4/2010 | Kiss |

(Continued)

FOREIGN PATENT DOCUMENTS

| EP | 1952823 A1 | 8/2008 |
|---|---|---|
| EP | 1985697 A1 | 10/2008 |

(Continued)

OTHER PUBLICATIONS

Alshahrani, et al., "Stability-enhanced Hot-melt Extruded Amorphous Solid Dispersions via Combinations of Soluplus® and HPMCAS-HF," American Association of Pharmaceutical Scientists, vol. 16, No. 4, pp. 824-834, Aug. 2015.

Beumer, et al., "Calf Intestinal Alkaline Phosphatase, A Novel Therapeutic Drug for Lipopolysaccharide (LPS)-Mediated Diseases, Attenuates LPS Toxicity in Mice and Piglets," The Journal of Pharmacology and Experimental Therapeutics, vol. 307, No. 2, pp. 737-744 (Jul. 2003).

(Continued)

*Primary Examiner* — Hope A Robinson
(74) *Attorney, Agent, or Firm* — Morgan, Lewis & Bockius LLP

(57) ABSTRACT

The present invention provides for a formulation comprising an active alkaline phosphatase (AP)-based agent and an enteric agent, wherein the formulation is suitable for releasing a substantial amount of the active AP-based agent in the intestines.

16 Claims, 23 Drawing Sheets

Specification includes a Sequence Listing.

(56) References Cited

U.S. PATENT DOCUMENTS

| | | | |
|---|---|---|---|
| 7,718,170 B2 | 5/2010 | Kiss | |
| 7,763,712 B2 | 7/2010 | Crine et al. | |
| 7,781,423 B2 | 8/2010 | Kiss | |
| 7,786,082 B2 | 8/2010 | Kiss | |
| 7,790,685 B2 | 9/2010 | Kiss | |
| 7,858,085 B2 | 12/2010 | Kiss | |
| 7,943,126 B2 | 5/2011 | Tomatsu et al. | |
| 7,943,606 B2 | 5/2011 | Kiss | |
| 7,960,529 B2 | 6/2011 | Crine et al. | |
| 7,964,188 B2 | 6/2011 | Kiss | |
| 8,372,638 B2 | 2/2013 | Kiss | |
| 8,460,654 B2 | 6/2013 | Kiss | |
| 8,557,545 B2 | 10/2013 | Velders et al. | |
| 8,574,863 B2 | 11/2013 | Brands et al. | |
| 8,586,032 B2 | 11/2013 | Pickkers et al. | |
| 8,603,464 B2 | 12/2013 | Kiss | |
| 8,647,854 B2 | 2/2014 | Lee et al. | |
| 8,691,208 B2 | 4/2014 | Tomatsu et al. | |
| 8,735,087 B2 | 5/2014 | Brands et al. | |
| 8,778,674 B2 | 7/2014 | Kiss | |
| 8,784,805 B2 | 7/2014 | Brands | |
| 8,784,833 B2 | 7/2014 | Sly et al. | |
| 8,932,587 B2 | 1/2015 | Hodin et al. | |
| 9,133,446 B2 | 9/2015 | Aiba et al. | |
| 9,631,185 B2 | 4/2017 | Schyns et al. | |
| 9,926,544 B2 | 3/2018 | Raaben et al. | |
| 9,976,129 B2 | 5/2018 | Kamiya et al. | |
| 9,988,620 B2 | 6/2018 | Crine et al. | |
| 10,000,532 B2 | 6/2018 | Crine et al. | |
| 10,052,366 B2 | 8/2018 | Crine et al. | |
| 10,449,236 B2 | 10/2019 | Marozsan et al. | |
| 10,570,380 B2 | 2/2020 | Jonk et al. | |
| 10,603,361 B2 | 3/2020 | Odrljin | |
| 10,987,410 B2 * | 4/2021 | Wacher | A61K 47/02 |
| 2004/0091530 A1 | 5/2004 | Ende et al. | |
| 2007/0280922 A1 | 12/2007 | Kiss | |
| 2010/0221234 A1 | 9/2010 | Crine et al. | |
| 2010/0297119 A1 | 11/2010 | Crine et al. | |
| 2011/0206654 A1 | 8/2011 | Hodin et al. | |
| 2012/0308526 A1 | 12/2012 | Ohtake et al. | |
| 2013/0045192 A1 | 2/2013 | Movalia et al. | |
| 2013/0108635 A1 | 5/2013 | Crine et al. | |
| 2013/0280232 A1 | 10/2013 | Brands et al. | |
| 2013/0323244 A1 | 12/2013 | Crine et al. | |
| 2014/0056980 A1 | 2/2014 | Oliveira Varum et al. | |
| 2015/0216813 A1 | 8/2015 | Everett et al. | |
| 2017/0252327 A1 | 9/2017 | Hodin et al. | |
| 2018/0326018 A1 * | 11/2018 | Wacher | A61K 9/0095 |
| 2021/0030686 A1 * | 2/2021 | Bristol | A61K 9/2846 |
| 2021/0220448 A1 * | 7/2021 | Wacher | A61K 47/12 |

FOREIGN PATENT DOCUMENTS

| | | | | |
|---|---|---|---|---|
| EP | 1759001 B1 | | 4/2011 | |
| EP | 2158319 B1 | | 7/2011 | |
| EP | 2368999 B1 | | 3/2014 | |
| EP | 2662448 B1 | | 12/2016 | |
| WO | WO9951211 | * | 1/1999 | |
| WO | WO 1999/026654 A1 | | 6/1999 | |
| WO | WO 1999/033955 A1 | | 7/1999 | |
| WO | WO 1999/037678 A2 | | 7/1999 | |
| WO | WO 2000/032629 A2 | | 6/2000 | |
| WO | WO 2001/034641 A2 | | 5/2001 | |
| WO | WO 2001/056627 A1 | | 8/2001 | |
| WO | WO 2002/060503 A1 | | 8/2002 | |
| WO | WO 2004/112494 A2 | | 12/2004 | |
| WO | WO 2005/055956 A2 | | 6/2005 | |
| WO | WO 2005/074978 A1 | | 8/2005 | |
| WO | WO 2005/103263 A1 | | 11/2005 | |
| WO | WO 2007/055760 A2 | | 5/2007 | |
| WO | WO 2007/081654 A2 | | 7/2007 | |
| WO | WO 2008/024103 A1 | | 2/2008 | |
| WO | WO 2008/094037 A1 | | 8/2008 | |
| WO | WO 2008/104199 A1 | | 9/2008 | |
| WO | WO 2008/104200 A1 | | 9/2008 | |
| WO | WO 2008/133511 A2 | | 11/2008 | |
| WO | WO 2008/138131 A1 | | 11/2008 | |
| WO | WO-2008133511 A2 | * | 11/2008 | A61K 38/465 |
| WO | WO 2009/028943 A1 | | 3/2009 | |
| WO | WO 2009/106368 A1 | | 9/2009 | |
| WO | WO 2010/025267 A2 | | 3/2010 | |
| WO | WO 2010/151526 A1 | | 12/2010 | |
| WO | WO 2011/057250 A1 | | 5/2011 | |
| WO | WO 2011/134084 A1 | | 11/2011 | |
| WO | WO 2012/054057 A1 | | 4/2012 | |
| WO | WO 2012/169892 A2 | | 12/2012 | |
| WO | WO 2012/177100 A2 | | 12/2012 | |
| WO | WO 2013/058833 A1 | | 4/2013 | |
| WO | WO 2013/059491 A1 | | 4/2013 | |
| WO | WO 2015/112015 A1 | | 7/2015 | |
| WO | WO 2015/112017 A1 | | 7/2015 | |
| WO | WO 2015/166045 A2 | | 11/2015 | |
| WO | WO 2016/090251 A1 | | 6/2016 | |
| WO | WO 2016/123342 A2 | | 8/2016 | |
| WO | WO 2017/031114 A1 | | 2/2017 | |
| WO | WO 2017/058822 A1 | | 4/2017 | |
| WO | WO 2017/074466 A1 | | 5/2017 | |
| WO | WO 2017/155569 A1 | | 9/2017 | |
| WO | WO 2017/173395 A1 | | 10/2017 | |
| WO | WO 2017/173413 A1 | | 10/2017 | |
| WO | WO 2017/214130 A1 | | 12/2017 | |
| WO | WO 2018/009555 A1 | | 1/2018 | |
| WO | WO 2018/035420 A1 | | 2/2018 | |
| WO | WO 2018/127363 A1 | | 7/2018 | |
| WO | WO 2018/164995 A1 | | 9/2018 | |
| WO | WO 2018/175413 A1 | | 9/2018 | |
| WO | WO 2018/183720 A1 | | 10/2018 | |
| WO | WO 2017/203426 A1 | | 2/2019 | |
| WO | WO 2018/183720 A9 | | 7/2019 | |
| WO | WO 2019/139891 A1 | | 7/2019 | |
| WO | WO 2019/172766 A1 | | 9/2019 | |
| WO | WO 2019/183209 A1 | | 9/2019 | |
| WO | WO 2019/190752 A1 | | 10/2019 | |
| WO | WO 2019/245938 A1 | | 12/2019 | |
| WO | WO 2020/033867 A2 | | 2/2020 | |

OTHER PUBLICATIONS

Chen, et al., "A Role for Intestinal Alkaline Phosphatase in the Maintenance of Local Gut Community," Dig Dis Sci. Apr. 2011; 56(4): 1020-1027 (doi:10.1007/s 10620-010-1396-x).

Chen, et al. "Identification of specific targets for the gut mucosal defense factor intestinal alkaline phosphatase," American Journal of Physiology, Aug. 2010, Epub May 2012, vol. 299, No. 2 pp. G467-75.

Cui, et al., "Faecal microbiota transplantation protects against radiation-induced toxicity", EMBO Molecular Medicine vol. 9 | No. 412017, 14 pages.

Curatolo, et al., "Utility of Hydroxypropylmethylcellulose Acetate Succinate (HPMCAS) for Initiation and Maintenance of Drug Supersaturation in the GI Milieu," Pharmaceutical Research, vol. 26, No. 6, pp. 1419-1431 (Jun. 2009).

Economopoulos, et al., "Prevention of antibiotic-associated metabolic syndrome in mice by intestinal alkaline phosphatase," Diabetes, Obesity and Metabolism, vol. 18, No. 5., pp. 519-527 (May 2016).

Estaki, et al., "Interplay between intestinal alkaline phosphatase, diet, gut microbes and immunity," World Journal of Gastroenterology, 20(42), pp. 15650-15656 (Nov. 2014).

Friesen, et al., "Hydroxypropyl Methylcellulose Acetate Succinate-Based Spray-Dried Dispersions: An Overview," Molecular Pharmaceuticals, vol. 5, No. 6, pp. 1003-1019 (Dec. 2008).

Goldberg, et al., "Intestinal alkaline phosphatase is a gut mucosal defense factor maintained by enteral nutrition," PNAS, vol. 105, No. 9, pp. 3551-3556 (Mar. 2008).

Hauer-Jensen, et al., "Radiation Enteropathy—Pathogenesis, Treatment, and Prevention", Nat Rev Gastroenterol Hepatol. Aug. 2014; 11(8): 470-479. doi:10.1038/nrgastro.2014.46, 27pages.

(56) References Cited

OTHER PUBLICATIONS

International Search Report & Written Opinion, PCT/US2018/023327, datedMay 25, 2018, 12 pages.

Kaliannan, et al., "Intestinal alkaline phosphatase prevents metabolic syndrome in mice," PNAS, vol. 110, No. 17, pp. 7003-7008 (Apr. 2013).

Lallès, "Intestinal alkaline phosphatase: novel functions and protective effects," Nutrition Reviews, vol. 72(2), pp. 82-94 (2014).

Liu, et al., "Intestinal Alkaline Phosphatase Regulates Tight Junction Protein Levels", J Am Coll Surg. Jun. 2016: 222(6): 1009-1017. doi:10.1016/j.jamcollsurg.2015.12.006.

Malo, et al., "Intestinal alkaline phosphatase preserves the normal homeostasis of gut microbiota," Gut 2010;59:1476-1484 (doi:10.1136/gut.2010.211706).

Parlato, et al., "Human ALPI deficiency causes inflammatory bowel disease and highlights a key mechanism of gut homeostasis," EMBO Molecular Medicine, e8483, pp. 1-12 (Mar. 2018).

Peters, et al., "The Potential of Alkaline Phosphatase as a Treatment for Sepsis-Associated Acute Kidney Injury," Nephron Clin Pract 2014; 127: pp. 144-148 (Sep. 2014).

Ramasamy, et al., "Intestinal Alkaline Phosphatase Has Beneficial Effects in Mouse Models of Chronic Colitis", Inflamm Bowel Dis. Feb. 2011; 17(2): 532-542. doi:10.1002/ibd.21377.

Rentea, et al., "Radiation-induced changes in intestinal and tissue-nonspecific alkaline phosphatase: implications for recovery after radiation therapy", The American Journal of Surgery (2016) 212, 602-608, 7 pages.

Rieder, et al., "Animal models of intestinal fibrosis: new tools for the understanding of pathogenesis and therapy of human disease", Am J Physiol Gastrointest Liver Physiol 303: G786-G801, 2012, 16 pages.

Shah, et al., "Improved Human Bioavailability of Vemurafenib, a Practically Insoluble Drug, Using an Amorphous Polymer-Stabilized Solid Dispersion Prepared by a Solvent-Controlled Coprecipitation Process," Journal of Pharmaceutical Sciences, vol. 102, No. 3, pp. 967-981 (Mar. 2013).

Eriksson, et al., "Investigations into the stabilization of drugs by sugar glasses: II Delivery of an insulin-stabilised alkaline phosphatase in the intestinal lumen via the oral route," International Journal of Pharmaceutics, vol. 257, pp. 273-281, 2003.

International Search Report & Written Opinion, PCT Appl. No. PCT/US19/23142, dated Aug. 1, 2019, 17 pages.

\* cited by examiner

FIGURE 1

HIAP – SEQ ID NO: 1

1 mqgpwvllll glrlqlslgv ipaeeenpaf wnrqaeeald aakklqpiqk vaknlilflg 61 dglgvptvta trilkgqkng klgpetplam drfpylalsk tynvdrqvpd saatataylc 121 gvkanfqtig lsaaarfnqc nttrgnevis vmmrakqagk svgvvtttrv qhaspagtya 181 htvnrnwysd admpasarqe gcqdiatqli snmdidvilg ggrkymfpmg tpdpeypada 241 sqngirldgk nlvqewlakh qgawyvwnrt elmqasldqs vthlmglfep gdtlkyeihrd 301 ptldpslmem teaalrllsr nprgfylfve ggridhghhe gvayqaltea vmfddaiera 361 gqltseedtl tlvtadhshv fsfggytlrg ssifglapsk aqdskaytsi lygngpgyvf 421 nsgvrpdvne sesgspdyqq qaavplsset hggedvavfa rgpqahlvhg vqeqsfvahv 481 mafaaclepy tacdlappac ttdaahpvaa slpllagtll llgasaap BIAP II with 248D assignment – SEQ ID NO: 2. The signal peptide and sequence past 480 are derived from bIAP I.

1 mqgacvllll glhlqlslgl ipaeeenpaf wnrqaaqald vakklqpiqt aaknvilflg 61 dgmgvptvta trilkgqmng klgpetplam dqfpyvalsk tynvdrqvpd sagtataylc 121 gvkgnyrtig vsaaarynqc nttrgnevts vinrakkagk avgvvtttrv qhaspagaya 181 htvnrnwysd adlpadaqkn gcqdiaaqlv ynmdidvilg ggrmymfpeg tpdpeypdda

FIGURE 1 (continued)

241 svngvrkdkq nlvqewqakh qgaqyvwnrt allqaaddss vthlmglfep admkynvqqd
301 htkdptlaem teaalqvlsr nprgfylfve ggridhghhd gkaymaltea imfdnaiaka
361 neltseldtl ilvtadhshv fsfggytlrg tsifglapgk aldsksytsi lyngpgyal
421 gggsrpdvng stseepsyrq qaavplaset hggedvavfa rgpqahlvhg vqeetfvahi
481 mafagcvepy tdcnlpapat atsipdaahl aasppplall agamllllap tly

BIAP IV – SEQ ID NO: 3

1 mqwacvllll glwlqlsltf ipaeeedpaf wnrqaaqald vakklqpiqt aaknvilflg
61 dgmgvptvta trilkgqmng klgpetplam dqfpyvalsk tynvdrqvpd sagtataylc
121 gvkgnyktig vsaaarynqc nttsgnevts vmnrakkagk svgvvttsrv qhaspagaya
181 htvnmwysd adlpadaqty gcqdiatqlv nmmdidvilg ggrmymfpeg tpdpeypydv
241 nqtgvrkdkr nlvqewqakh qgaqyvwnrt ellqaandps vthlmglfep admkynvqqd
301 ptkdptleem teaalqvlsr npqgfylfve ggridhghhe gkaymaltdt vmfdnaiaka
361 neltseldtl ilatadhshv fsfggytlrg tsifglapsk asdnksytsi lyngpgyvl
421 ggglrpdvnd sisedpsyrq qaavplsses hggedvavfa rgpqahlvhg vqeetfvahv
481 mafagcvepy tdcnlpapsg lsdaahlaas ppslallaga mllllapaly

FIGURE 1 (continued)

HIAP with stop codon (SEQ ID NO: 4)

1 mqgpwvllll glrlqlslgv ipaeeenpaf wnrqaaeald aakklqpiqk vaknlilflg
61 dglgvptvta trilkgqkng klgpetplam drfpylalsk tynvdrqvpd saatataylc
121 gvkanfqtig lsaaarfnqc nttrgnevis vmmrakqagk svgvvtttrv qhaspagtya
181 htvnrnwysd admpasarqe gcqdiatqli snmdidvilg ggrkymfpmg tpdpeypada
241 sqngirldgk nlvqewlakh qgawyvwnrt elmqasldqs vthlmglfep gdtlkyeihrd
301 ptldpslmem teaalrllsr nprgfylfve ggridhghhe gvayqaltea vmfddaiera
361 gqltseedtl tlvtadhshv fsfggytlrg ssifglapsk aqdskaytsi lygngpgyvf
421 nsgvrpdvne sesgspdyqq qaavplsset hggedvavfa rgpqahlvhg vqeqsfvahv
481 mafaaclepy tacdllappag ttd BIAP II with stop codon (SEQ ID NO: 5)

1 mqgacvllll glhlqlslgl ipaeeenpaf wnrqaagald vakklqpiqt aaknvilflg
61 dgmgvptvta trilkgqmng klgpetplam dqfpyvalsk tynvdrqvpd sagtataylc
121 gvkgnyrtig vsaaarynqc nttrgnevts vinrakkagk avgvvtttrv qhaspagaya
181 htvnrnwysd adlpadaqkn gcqdiaaqlv ynmdidvilg ggrmymfpeg tpdpeypdda
241 svngvrkdkq nlvqewqakh qgaqyvvwnrt allqaaddss vthlmglfep admkynvqqd

FIGURE 1 (continued)

301 htkdptlaem teaalqvlsr nprgfylfve ggridhghhd gkaymaltea imfdnaiaka 361 neltseldtl ilvtadhshv fsfggytlrg tsifglapgk aldsksytsi lygngpgyal 421 gggsrpdvng stseepsyrq qaavplaset hggedvavfa rgpqahlvhg vqeetfvahi 481 mafagcvepy tdcnlpapat atsipd BIAP IV with stop codon (SEQ ID NO: 6)

1 mqwacvllll glwlqlsltf ipaeeedpaf wnrqaaqald vakklqpiqt aaknvilflg 61 dgmgvptvta trilkgqmng klgpetplam dqfpyvalsk tynvdrqvpd sagtataylc 121 gvkgnyktig vsaaarynqc nttsgnevts vmnrakkagk svgvvttsrv qhaspagaya 181 htvnrnwysd adlpadaqty gcqdiatqlv nnmdidvilg ggrmymfpeg tpdpeypydv 241 nqtgvrkdkr nlvqewqakh qgaqyvwnrt ellqaandps vthlmglfep admkynvqqd 301 ptkdptleem teaalqvlsr npqgfylfve ggridhghhe gkaymaltdt vmfdnaiaka 361 neltseldtl ilatadhshv fsfggytlrg tsifglapsk asdnksytsi lygngpgyvl 421 ggglrpdvnd sisedpsyrq qaavplsses hggedvavfa rgpqahlvhg vqeetfvahv 481 mafagcvepy tdcnlpapsg lsd BIAP IV with stop codon after amino acid 508 (SEQ ID NO: 7)

FIGURE 1 (continued)

```
  1 mqwacvllll glwlqsltf ipaeeedpaf wnrqaaqald vakklqpiqt aaknvilflg
 61 dgmgvptvta trilkgqmng klgpetplam dqfpyvalsk tynvdrqvpd sagtataylc
121 gvkgnyktig vsaaarynqc nttsgnevts vmmrakkagk svgvvtsrv qhaspagaya
181 htvnmwysd adlpadaqty gcqdiatqlv nmmdidvilg ggrmymfpeg tpdpeypydv
241 nqtgvrkdkr nlvqewqakh qgaqyvwnrt ellqaandps vthlmglfep admkynvqqd
301 ptkdptleem teaalqvlsr npqgfylfve ggridhghhe gkaymaltdt vmfdnaiaka
361 neltseldtl ilatadhshv fsfggytlrg tsifglapsk asdnksytsi lygngpgyvl
421 ggglrpdvnd sisedpsyrq qaavplsses hggedvavfa rgpqahlvhg vqeetfvahv
481 mafagcvepy tdcnlpapsg lsdaahla
```

BIAP II with Fc Fusion (SEQ ID NO: 8) – Fc domain is underlined

```
  1 mqgacvllll glhlqlslgl ipaeeenpaf wnrqaaqald vakklqpiqt aaknvilflg
 61 dgmgvptvta trilkgqmng klgpetplam dqfpyvalsk tynvdrqvpd sagtataylc
121 gvkgnyrtig vsaaarynqc nttrgnevts vinrakkagk avgvvtttrv qhaspagaya
181 htvnmwysd adlpadaqkn gcqdiaaqlv ynmdidvilg ggrmymfpeg tpdpeypdda
241 svngvrkdkq nlvqewqakh qgaqyvwnrt allqaaddss vthlmglfep admkynvqqd
301 htkdptlaem teaalqvlsr nprgfylfve ggridhghhd gkaymaltea imfdnaiaka
```

FIGURE 1 (continued)

```
361 neltseldtl ilvtadhshv fsfggytlrg tsifglapgk aldsksytsi lygngpgyal
421 gggsrpdvng stseepsyrq qaavplaset hggedvavfa rgpqahlvhg vqeetfvahi
481 mafagcvepy tdcnlpapat atsipdGGSGGSGGGSGGGSGGGSEPKSCDKTHTCPPCPAPE LLGGPSVFLFPPKPKDTLMI
SRTPEVTCVVVDVSHEDPQV KFNWYVDGVQVHNAKTKPRE QQYNSTYRVVSVLTVLHQNW LDGKEYKCKVSNKALPAPIE
KTISKAKGQPREPQVYTLPP SREEMTKNQVSLTCLVKGFY PSDIAVEWESNGQPENNYKT TPPVLDSDGSFFLYSKLTVD
KSRWQQGNVFSCSVMHEALH NHYTQKSLSLSPGK
```

BIAP IV with Fc Fusion (SEQ ID NO: 9) – Fc domain is underlined

```
1   mqwacvllll glwlqlsltf ipaeeedpaf wnrqaaqald vakklqpiqt aaknvilflg
61  dgmgvptvta trilkgqmng klgpetplam dqfpyvalsk tynvdrqvpd sagtatayle
121 gvkgnyktig vsaaarynqc nttsgnevts vmnrakkagk svgvvttsrv qhaspagaya
181 htvnrnwysd adlpadaqty gcqdiatqlv nmmdidvilg ggrmymfpeg tpdpeypydv
241 nqtgvrkdkr nlvqewqakh qgaqyvwnrt ellqaandps vthlmglfep admkynvqqd
301 ptkdptleem teaalqvlsr npqgfylfve ggridhghhe gkaymaltdt vmfdnaiaka
361 neltseldtl ilatadhshv fsfggytlrg tsifglapsk asdnksytsi lygngpgyvl
421 ggglrpdvnd sisedpsyrq qaavplsses hggedvavfa rgpqahlvhg vqeetfvahv
481 mafagcvepy tdcnlpapsg lsdGGSGGSGGGSGGGSGGGSEPKSCDKTHTCPPCPAPE LLGGPSVFLFPPKPKDTLMI
SRTPEVTCVVVDVSHEDPQV KFNWYVDGVQVHNAKTKPRE QQYNSTYRVVSVLTVLHQNW LDGKEYKCKVSNKALPAPIE
```

FIGURE 1 (continued)

KTISKAKGQPREPQVYTLPP SREEMTKNQVSLTCLVKGFY PSDIAVEWESNGQPENNYKT TPPVLDSDGSFFLYSKLTVD KSRWQQGNVFSCSVMHEALH NHYTQKSLSLSPGK

BIAP IV with the hPLAP Carboxy Terminus and Mutation for Unprocessed Secretion and RV3C Cleavage (at ...LEVLFQGP...): SEQ ID NO: 10

```
  1 mqwacvllll glwlqlsltf ipaeeedpaf wnrqaaqald vakklqpiqt aaknvilflg
 61 dgmgvptvta trilkgqmng klgpetplam dqfpyvalsk tynvdrq

FIGURE 1 (continued)

```
  1 mqwacvllll glwlqlsltf ipaeeedpaf wnrqaaqald vakklqpiqt aaknvilflg
 61 dgmgvptvta trilkgqmng klgpetplam dqfpyvalsk tynvdrqvpd sagtataylc
121 gvkgnyktig vsaaarynqc nttsgnevts vmnrakkagk svgvvttsrv qhaspagaya
181 htvnmmwysd adlpadaqty gcqdiatqlv nnmdidvilg ggrmymfpeg tpdpeypydv
241 nqtgvrkdkr nlvqewqakh qgaqyvwnrt ellqaandps vthlmglfep admkynvqqd
301 ptkdptleem teaalqvlsr npqgfylfve ggridhghhe gkaymaltdt vmfdnaiaka
361 neltseldtl ilatadhshv fsfggytlrg tsifglapsk asdnksytsi lygngpgyvl
421 ggglrpdvnd sisedpsyrq qaavplsses hggedvavfa rgpqahlvhg vqeetfvahv
481 mafagcvepy tdcnlappag ttdaahpieg rsvvpallpl ragtlllet atap
``` hIAP with native first intron (shown as bolded and underlined)- SEQ ID NO: 12

ATGCAGGGGCCCTGGGTGCTGCTGCTGCTGGGCCTGTGGCTCCAGAGCTCCCTGACCTTCATCCCAGGTAATGAGGCTCCCCAA
GCTGTTCCACACAGGGCACCCCTCAGCAGGCTGACCTGCAGCCCCTGCAGTCTCTACTCTCCCCCTGCCAGCTGAGGAGGAGAACC
GGCCTTCTGGAACCGCCAGGCAGCTGAGGCCCTGGATGCTGCCAAGAAGTGCCAGCCATCCAGAAGGTCGCCAAGAACCTCA
TCCTCTTCCTGGGCGATGGGTTGGGGTGCCACGGTGACAGCAGCGATCCTAAAGGGCAGAAGAATGGCAAACTGGGGC
CTGAGACGCCCCTGGCCATGGACCGTTCCCATACCTGTGCCAAGACATACAATGTGACAGACAGTGCCAGACAGCG
CAGCCACAGCCACGGCCTACCTGTGCGGGGTCAAGGGCAACTTCCAGACCATCGGCTTGAGTGCAGCCGCCGCTTAACCAGTG
CAACACGACACGCGGCAATGAGGTCATCTCCGTGATGAACCGGGCCAAGCAAGCAGGAAAGTCAGTAGGAGTGGTGACCACCA

FIGURE 1 (continued)

CACGGGTGCAGCACGCCTCGCCAGCCGGCACCTACGCACCACACAGTGAACCGCAACTGGTACTCAGATGCTGACATGCTGCCT
CAGCCCGCCAGGAGGGTGCCAGGACATCGCCACTCAGTCATCTCCAACATGGACATTGACGTGATCCTTGGCGGAGCCGCA
AGTACATGTTTCCCATGGGGACCCCAGACCCTGAGTACCCAGCTGATGCCAGCCAGAATGGAATCAGGCTGGACGGGAAGAACC
TGGTGCAGGAATGGCTGGCAAAGCACCAGGGTGCCTCTTTGAACCGCACTGAGTCTCATGCAGCGTCCTGGACCAGT
CTGTGACCCATCTCATGGGCCTCTTTGAGCCCTGCCGCTGCTGAGCACACGAGAAATATGAGATCACCGAGACCCACACTGGACCCCTCCTGAT
GGAGATGACAGAGGCTGCCTGCCGCTGTGAGCAGGAACCCCGGGCTTCTACCCTCTTTGTGGAGGGCGGCATCGACCA
TGGTCATCATGAGGGTGTGGCTTACCAGCACTCACTGTTGCAGCGCATTGAGAGGGCGGGCCAGCTCAC
CAGCGAGGAGGACACGCTGACCCCTCGTCACCGCTGACCACTCCCATGTCTCTTCTCCTTGGTGCTACACCTTGCGAGGGAGCTCC
ATCTTCGGGTTGGCCCCCAGCAAGGCTCAGGACACAGCAAAGCTACACGTCCATCCTGTACGGCAGCAGCCCGGGCTACGTGTTCA
ACTCAGGCGTGCGACCAGACAGAGAGCGAGAACGTGAATGAGACACCCCAAGGCGGGAGCCCGCCAGGCGCCCGCAGGAGCCGGCGGTGCCCTGTCCG
AGACCCACGAGGGCGAAAGACGTGGGGTGTTTGCGCGGCCCGGGGACCCCTGCTGCCCTGTGCCAGGAGCAGAGCTTCG
TAGCGCATGTCATGGCCTTCGCTGCCTGTCTCGGAGCCCTGCGACCCTGGCGCTCCCGCCCTGCACCACCGACGCCGC
GCACCCAGTTGCCCGCCACTGCTGCCGCTGCCTGCTGCTGGGGGCGTCCGCTGCCCTGA hIAP with native 3' UTR (shown as bolded and underlined) – SEQ ID NO: 13

ATGCAGGGGCCCTGGGTGCTGCTGCTCGAGGCTACAGCTCTCCCTGGCGTCATCCCAGCTGAGGAGGAGAACCCG
GCCTTCTGAACCGCCAGGCAGCTGAGGCCCTGAGCCCTGGATGCTGCCAAGAAGCTGCCAAGAAGGTCGCCAAGAACCTCATC
CTCTTCCTGGGCGATGGGTTGGGGGGTGCCCACGGTGACAGCAGCCACCAGGTCCTAAAGGGGCAGAAGAATGGCAAACTGGGGCCT
GAGACGCCCCTGGCCATGGACCGCTTCCCATACCTGGCTCTGTCCAAGACACATACAATGTGGACACAGGTGCCAGACAGCGCA
GCCACAGCCACGCCACGGCCTACCTGTGCGGGGTCAAGGCCAACTTCCAGACCATCGGCTTGAGTGCAGCCGCCGCTTTAACCAGTGCA
ACACGACACGCGGCAATGAGGTCATCTCCGTGATGAACCGGGCCAAGCAAGCAGGAAAGTCAGTAGGAGTGGTGACCACCA

FIGURE 1 (continued)

CGGGTGCAGCACGCCTCGCCAGCCGGCACCTACGCACACACAGTGAACCGCAACTGGTACTCAGATGTGACATGCTGCCTCA
GCCCGCCAGGAGGGTGCCAGGACATCGCCACTCAGCTCATCTCCAACATGGACATTGACGTGATCCTTGGCGGAGCCGCAAG
TACATGTTTCCCATGGGGACCCCAGACCCTGAGTACCCAGCTGATGCCAGCCAGAATGGAATCAGGCTGGACGGGAAGAACCTG
GTGCAGGAATGGCTGGCAAAGCACCAGGGTGCCTGGTATGTGTGGAACCGCACTGAGCTCATGCAGGCGTCCCTGACCAGTCT
GTGACCCATCTCATGGGCCTCTTTGAGCCCGGAGACACGAAATATGAGATCCACGAGACCCACACTGGACCCCTCCCTGATGG
AGATGACAGAGGCTGCCTGCCCTGAGCAGGAACCCCGGCTTCTACCTCTTTGTGAGGGGCGCATGCACCATG
GTCATCATGAGGGTGTGCTTACCAGGCACTCACTGAGGCGGTCATGTTCGACGCCATTGAGACGCCAGTCACCA
GCGAGGAGGACACGCTGGACCCCTCGTCACCGCTGACCACTCCCATGTCTTCTCCTTTGGTGCTACACCTTGCGAGGGAGCTCCAT
CTTCGGGTTGGCCCCCAGCAAGGCTCAGGACAGCAGCAAAGCCTACACGTCCATCATCGTATACGCAATGGCCCGGCTACGTGTTCAAC
TCAGGCGTGCGACCAGCAGACGTGAATGAGAGCGGGAGCGGGGAGCCCGATTACCAGCAGCCCCCTGTCCCTCGTCCGA
GACCCACGGAGGCGAAGACGTGGCGGTGTTGCGCGGCAGGCCACCTGGTGCATGGTGTGCAGGAGCAGAGCTTCGT
AGCGCATGTCATGGCCTTCGCTGCTCGTGTCTGCTGCCACTGGACCCTGCGGAGCCTACACGCCTGGCCGTCCCGCCTGCACCACCGACGCCGCG
CACCCAGTTGCCGGTCGCCGGTGCCGGACCCCTGCTGCGGGGGCGTCCCTGCTGTGGGGGCGTCCCTGATTTACTAAACCT
TGAAATAAAATTGTAAAACATCAGTTTGAAGGCCTGACTCTCAGGGTAGTTCTTTTTAATTCTGGGTTT bIAP IV with the first intron from bIAP I (shown as bolded and underlined) – SEQ ID NO: 14

ATGCAGTGGGCCTGTGTGCTGCTGCTGCTGGGCCTGTGGCTGCAGCCTGGGGCTGTCCTCATCCCAGGTAATCAGGGCGCTCCC
AGCAGCCCCCTACTCACAGGGCCTCTAGGGCCTCGAGGCTGACCTGACCAACACTCTCCCCTTGGGCAGCTGAGGAGGAAGACCCCG
CCTTCTGGAACCTGCCCAGGCCCAGCCCTTGATGTAGCCAAGAAGTTGCAGCCGATCCAGACAGCTGCCAAGAATGTCATCC
TCTTCTTGGGGGATGGGATGGGGGTGCCTACGCAGCCACTCGGATCCTAAAGGGCAGATGAATGGTAAGCTGGGACCTG
AGACACCCCTGGCCATGGACCCAGTTCCATACGTGGCTCTGTCCAAGACATACAACGTGGACAGACAGGCTGCCAGACAGCGCAG

FIGURE 1 (continued)

GCACTGCCACTGCCTACCTGTGTGTGGGTCAAGGGCAACTACAAACCATTGGTGTAAGTGCAGCCGCCCGCTACAACCAGTGCA
ACACAAACAAGTGGCAATGAGGTCACGTCTGTGATGAACCGGGCCAAGAAAGCAGGAAAGTCAGTGGGAGTGGTGACCACCTCC
AGGGTGCAGCATGCCTCCCCAGCCGGTGCTTATGCACACACGGTGAAACTGGTACTCAGATGCCGACCTGCCTGCCGAT
GCACAGACGTATGCCTGCCAGGACATCGCCACACACAACTGGTCAACAACATGGATATTGACGTGATCCTGGGTGGAGGCCGAATG
TACATGTTTCTGAGGGACCCCAGGCAAGCCACCCAGGAGCCCAGTATGTGTGGAACCGCACGGAGCTCCTTCAGCAGCCAATGACCCAGT
GTGCAGGAGTGGCAGGCAAGCCACCCAGGAGCCCAGTATGTGTGGAACCGCACGGAGCTCCTTCAGCAGCCAATGACCCAGT
GTAACACACCTCATGGGCCTCTTTGAGCGGCAGACATGAAGTATAATGTTCAGCAAGACCCACCAAGGACCCGACCCTGGAG
GAGATGACGGAGGGGGCCTGCAAGTGCTGAGCAGGAACCCCCAGGGCTTCTACCCTCTCGTGGAGGAGGCCGCATTGACCAC
GGTCACCATGAAGGCAAAGCTTATATGCACTGACTGATACAGTCATGTTGACAATGCCATGCCAAGGCTAACGAGCTCACTA
GCGAACTGGACACGCTGATCCTTGCCACTGCAGACCACTCCATGTCTTCTCTTTGGTGCTACACACTGCGTGGGACCTCCATT
TTCGGTCTGGCCCCCAGCAAGGCCTCAGACAACAAGTCCTACACCTCCATCCTCTATGGCAATGGCCCTGGCTACGTGCTTGGTG
GGGGCTTAAGGCCCGATGTTAATGACAGCATAAGCGAGGACCCCCTCGTGCCCGTGCCCCTGTCTAGTGAGT
CCCACGGGGGGAGGACGTGGCGGTGTTCGCGGAGCGGCCACTGGTGCAGGCGTGCAGGAGGAGACCTTCGTG
GCGCACGTCATGGCCTTTGCGGCCTTCGCGTGAGCCCTACACCGACTGCAATCTGCCGCCCCCTCTGCCCTCTCCGACGCCGGC
ACCTGGCGGCCAGCCCGCTTCGCTGCTGCTGCTGGGCGATGCTGCTGCTGCTGCCTTGTACTGA bIAP IV with the 3' UTR from bIAP I (shown as bolded and underlined) – SEQ ID NO: 15

ATGCAGTGGGCCTGTGTGCTGCTGCTGGGCCTGTGGCTACAGCTCTCCCTCACCTTCATCCCAGCTGAGGAGGAAGACCCCG
CCTTCTGGAACCGGCAGCCAGCCCAGGCCCTTGATGTAGCCAAGAAGTTGCAGCCGATCCAGCAGCTGCCAAGAATGTCATCC
TCTTCTTGGGGATGGATGGGGGTGCCTAGCAGCCACTCGGATCCTAAAGGGGCAGATGAATGTAAGCTGGGACCTG
AGACACCCCCTGGCCATGACCATGGACGGACCAGTCCATAACGTGGCTCTGTCCAAGACATACAACGTGGACAGGTGCCAGACAGGCAG
GCACTGCCACTGCCTACCTGTGTGTGGGTCAAGGGCAACTACAAAACCATTGGTGTAAGTGCAGCCGCCCGCTACAACCAGTGCA

FIGURE 1 (continued)

ACACAACAAGTGGCAATGAGGTCACGTCTGTGATGAACCGGGCCAAGAAAGTCAGTGGGAGTGGTGACCACCTCC
AGGGTGCAGCATGCCTCCCCAGCCGGTGCTTATGCACACACGGTGAACGGTGAAACTGGTACTCAGATGCCGATGCCTGCCGAT
GCACAGACGTATGGCTGCCAGGACATCGCCACACAACTGGTCAACAACATGGATATTGACGTGATCCTGGGTGGAGGCCGAATG
TACATGTTTCCTGAGGGACACCGGATCCTGAATACCCATCAGATGTCAATACGATGTCAATCAGACTGGAGTCCGAAGGACAAGCGGAATCTG
GTGCAGGAGTGGCAGGCCAAGCACCAGGAGGCCAGTATGTGTGGAACCGCACGAGCTCCTTCAGGCAGCAGCCAATGACCCAGT
GTAACACACCTCATGGGCCTCTTTGAGCCGGCAGACATGAAGTATAATGTTCAGCAAGACCCCACCAAGACCCGACCCTGAG
GAGATGACGAGGCGGCCCTGCAAGTGCGGCCATGGAACCCCCAGGGCTTCTACCTCTTCGTGAGGAGGCCGCATTGACCAC
GGTCACCATGAAGGCAAAGCTTATATGGCACTGACTGATACAGTCATGTTTGACAATGCCAAGGCTAACGAGCTCACTA
GCGAACTGGACACGCTGATCCTTGCCAGACCACTCGCAGACAACAAGTCCTACACCTCCATATCCTATGGCCTGGCGTGGGGACCTCCATT
TTCGGTCTGGCCCCCAGCAGCCCGATGTTAATGACAGCATAAGCGAGGACCCCGCCAGGCCACCTGGTGCAGCGGCTGCAGGAGAGACCTTCGTG
GGGGCTTAAGGCCCGATGTTAATGACAGCATAAGCGAGGACCCCGCCAGGCCACCTGGTGCAGCGGCTGCAGGAGAGACCTTCGTG
CCCACGGGGCGAGGACGTGTTCGCGCAGGACGCCCTGGAGCCCTACACCGACTGCAATCTGCCGGCCTCTCCGACGCCGCGC
GCGCACGTCATGGCCTTTGCGGGCTTGCTGGGGCCCCTGGAGCCCTACACCGACTGCAATCTGCCGGCCTCTCCGACGCCGCGC
ACCTGGCGGCCAGCCCGCTTCGCTGGCCAGCCCGATGCTGCTGGCCTTGTACTGAGGGACC
CGGGGGTGGGGACACAGCCCCTGAAGAGAAGCCCTAGGTGGGGCCAGCCAGACCAGAGTGTCTGGGCCACAGAGACCAAAGGCAACTCAGAAGACCAAAGGCAACTCAGAAGACCAAAGGCAACTCAGACTGG
GAGTGATACATGTCTGAAGAGAAGCCCTAGGTGGGGCCAGCCAGACCAGAGTGTCTGGGCCACAGAGACCAAAGGCAACTCAGAAGACCAAAGGCAACTCAGAAGACCAAAGGCAACTCAGACTGG
GGTTAGGGAGGGGTGATGAAGGGCTGACGTTGAGCAAGGCTGACGTTGAGCAAGCAACTCAGAAGACCAAGTGGTGCAGGACTGG
GTGTGGTCAGCAGGGGACTGGTTGGGGGATCC

Bacillus subtilis JH642 alkaline phosphatase IV, mature protein nucleotide sequence – SEQ ID NO: 16

AAAAAACAAGACAAAGCTGAGATCAGAAATGTCATTGTGATGATAGGCGACGGCATGGGGACGCCTTACATAAGAGCCTACCGT
TCCATGAAAATAACGGTGACACACCGAATAACCCGAAGTTAACAGAATTTGACCGGAACCTGACAGGCATGATGATGACGCAT
CCGGATGACCCTGACTATAATATTACAGATTCAGCCGGAACAGCAGCGTTAAGACATTAGCGACAGGCGTTAAGACATATAACAATGCA
ATTGGCGTCGATAAAAACGGAAAAAAGTGAAATCTGTACTTGAAGAGGCCAAACAGCAAGGCAAGTCAACAGGGCTGTGCG
CACGTCTGAAATTAACCACGCCACTCCAGCCGCCCACAATGGCCGCCAATGAATCACGGAAAAACATGACCAAATCGCCAACAG

FIGURE 1 (continued)

CTATATGGATGACAAGATAAAAGGCAAACATAAAATAGACGTGCTGCTCGGCGGCGGAAAATCTTATTTAACCGCAAGAACAG
AAACTTGACAAGGAATTCAAACAAGCCGGCTACAGCTATGTGACAACTAAACAAGCATTGAAAAAAATAAGATCAGCAGG
TGCTCGGGCTTTTCGCAGATGGAGGGCTTGCTAAAGCGCTCGACCGTGACAGTAAAACACCGTCTCAAAGACATGACGGTTC
AGCAATTGATCGCCTGAACCAAATAAAAAAGGATTTTCTTGATGGTCGAAGGGAGCCAGATTGACTGGGCGGCCATGACAA
TGATACAGTAGGAGCCATGAGCGAGGTTAAAGATTTTGAACAGGCCTATAAAGCCGCGATTGAATTTGCGAAAAAGACAAACA
TACACTTGTGATTGCAACTGCTGACCATACAACCGGCGCTTTACCATTGGCGCAAACGGGAAAAGAATTGCACGCAGAACC
GATTCTCCGCTAAGAAACACCTGAATTCATGGCCAAAAAATCAGGAAGGCAAGCCGGTTAAAGATGTGCTCGCCCGCTAT
GCCAATCTGAAAGTCACATCTGAAGAAATCAAAAAGCGTTGAAGCAGCTGCACAGGCTGACAAAAGCAAAGGGGCCTCCAAAGC
CATCATCAAGATTTTTAATACCCGCTCCAACAGCGGATGGACGAGTACCGATCATACCGGCGAAGAAGTACCGGTATACGCGTA
CGGCCCCGGAAAAGAAAATTCCGCGATTGATTAACAATACGGACCAGGCAAACATCATATTTAAGATTTTAAAAACTGGAAA
A

Bacillus subtilis JH642 alkaline phosphatase IV, mature protein amino acid sequence - SEQ ID NO: 17

KKQDKAEIRNVIVMIGDGMGTPYIRAYRSMKNNGDTPNNPKLTEFDRNLTGMMMTHPDDPDYNITDSAAAGTALATGVKTYNNAIG
VDKNGKKVKSVLEEAKQQGKSTGLVATSEINHATPAAYGAHNESRKNMDQIANSYMDDKIKGKHKIDVLLGGGKSYFNRKNRNLTK
EFKQAGYSYVTTKQALKKNKDQQVLGLFADGGLAKALDRDSKTPSLKDMTVSAIDRLNQNKKGFFLMVEGSQIDWAAHDNDTVGA
MSEVKDFEQAYKAAIEFAKKDKHTLVIATADHTTGGFTIGANGEKNWHAEPILSAKKTPEFMAKKISEGKPVKDVLARYANLKVTSEE
IKSVEAAAQADKSKGASKAIIKFNTRSNSGWTSTDHTGEEVPVYAYGPGKEKFRGLINNTDQANIIFKILKTGK

FIGURE 2

| | | Endpoint Analysis | | | | | | Kinetic Analysis | | | | | | | | | | |
|---|---|---|---|---|---|---|---|---|---|---|---|---|---|---|---|---|---|---|
| | | 1 day | | 5 days | | 13 days | | 25 days | | 34 days | | 48 days | | 56 days | | 68 days | |
| | | Activity (%) | S.D. (%) | Activity (%) | S.D. (%) | Activity (%) | S.D. (%) | Activity (%) | S.D. (%) | Activity (%) | S.D. (%) | Activity (%) | S.D. (%) | Activity (%) | S.D. (%) | Activity (%) | S.D. (%) |
| Freeze dried IAP: Sugar ratios (direct reconstitution) | Batch 1 | | | | | | | | | Batch 2 (Day 1) | | (Day 14) | | | | | |
| | IAP alone | 99.2 | 3.7 | 97.3 | 2.3 | 90.0 | 1.4 | | | 91.2 | 6.9 | 73.2 | 0.7 | | | | |
| | 1:2 Mannitol | 90.7 | 1.9 | 94.6 | 2.1 | | | | | | | | | | | | |
| | 1:2 Sucrose | 99.9 | 1.9 | 94.4 | 1.3 | | | | | | | | | | | | |
| | 1:2 Trehalose | 93.8 | 2.7 | 92.9 | 0.9 | | | | | | | 76.1 | 0.6 | 79.8 | 2.0 | 73.5 | 4.9 |
| | 1:10 Mannitol | 78.3 | 0.7 | 93.5 | 1.5 | | | | | | | | | | | 76.4 | 0.1 |
| | 1:10 Sucrose | 93.6 | 2.2 | 90.1 | 0.0 | | | | | | | | | 74.6 | 0.6 | 66.0 | 0.6 |
| | 1:10 Trehalose | 92.2 | 0.0 | 92.4 | 2.3 | | | | | | | | | | | | |
| Freeze dried IAP alone: With manipulation | Ground | | | 38.0 | 0.1 | 51.8 | 0.7 | (IAP:sucrose 1:2) 67.4 | 3.6 | | | | | | | | |
| | Sieved | | | | | 51.8 | 1.2 | | | | | | | | | | |
| | Broken up Lyophilisate | | | | | | | 51.7 | 0.0 | | | | | | | | |
| | Inner cake | | | | | | | | | 62.2 | 1.5 | | | | | | |
| | Outer cake | | | | | | | | | 66.4 | 0.4 | | | | | | |
| | Cake base | | | | | | | | | (Hygroscopicity noted)* 66.6 | 0.0 | | | | | | |
| | Cake surface | | | | | | | | | 60.5 | 0.1 | | | | | | |
| | Rinsed vial | | | | | | | | | 3.1 | 0.5 | | | | | | |

FIGURE 3

| | Endpoint Analysis | | | | Kinetic Analysis | | | | | | | | | |
|---|---|---|---|---|---|---|---|---|---|---|---|---|---|---|
| | 3 days | | 7 days | | 1 day | | 7 days | | 9 days | | 15 days | | 23 days | |
| | Activity (%) | SD (%) | Activity (%) | SD (%) | Activity (%) | SD (%) | Activity (%) | SD (%) | Activity (%) | SD (%) | Activity (%) | SD (%) | Activity (%) | SD (%) |
| IAP Alone | 13.0 | 2.0 | 21.2 | 0.2 | | | | | | | | | | |
| Prior IAP composition formulation | | | | | 102.6 | 1.6 | 79.9 | 0.4 | 74.4 | 1.5 | 73.6 | 0.2 | 75.8 | 0.4 |
| Prior IAP composition formulation Solution (not spray dried) | | | | | 72.4 | 0.5 | | | | | | | | |
| FD* IAP:trehalose 1:2 | | | | | 85.7 | 1.2 | 86.5 | 0.2 | | | 78.2 (15 days) | 1.3 | | |
| FD* IAP:trehalose 1:10 | | | | | 85.1 | 0.2 | 61.6 | 0.5 | | | 87.4 (15 days) | 4.2 | | |
| FD* IAP:mannitol 1:2 with desiccant | | | | | 29.6 | 0.1 | | | | | | | | |
| FD* IAP:mannitol 1:2 without desiccant | | | | | 31.7 | 1.0 | | | | | | | | |
| FD* IAP:mannitol 1:10 with desiccant | | | | | 17.8 | 0.1 | | | | | | | | |
| FD* IAP:mannitol 1:10 without desiccant | | | | | 19.0 | 0.5 | | | | | | | | |
| FD* IAP:sucrose 1:2 with desiccant | | | | | 72.2 | 0.6 | 79.4 (7 days) | 2.9 | | | | | | |
| FD* IAP:sucrose 1:2 without desiccant | | | | | 65.5 | 0.1 | 74.8 (7 days) | 6.3 | | | | | | |

*FD refers to freeze dried material, which has been subsequently resuspended, and spray dried.

FIGURE 5A-C

FIGURE 8
A)
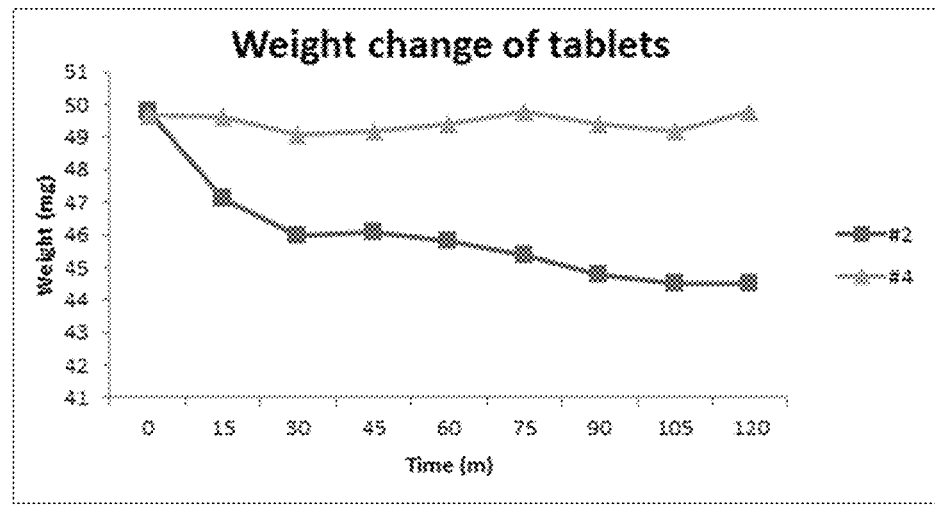
B)
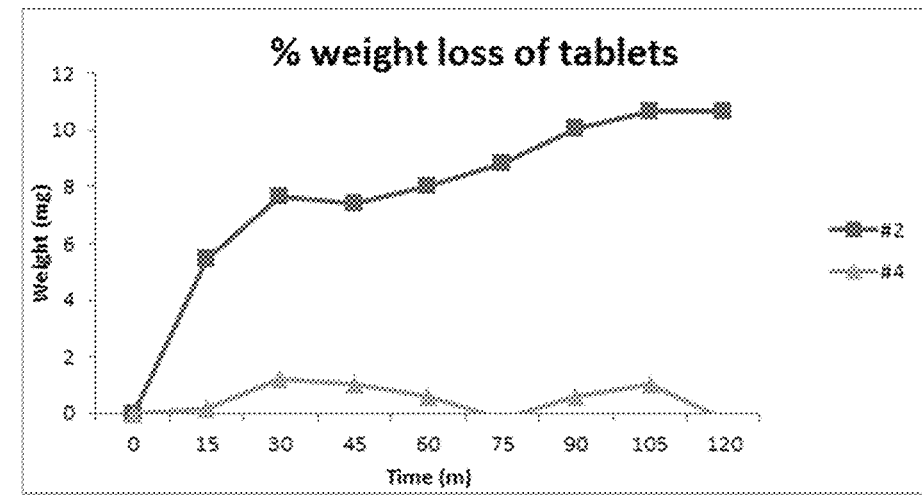

A)

B)

| Tablet: #1 (L30 D 55 coating alone) | Time (m) | 1 | | 2 | | 3 | |
|---|---|---|---|---|---|---|---|
| Sample | | Activity (%) | S.D. (%) | Activity as % of total (%) * | S.D. (%) | Release (%) | S.D (%) |
| #1 GF 1 hour | 60 | 0.76 | 0.18 | 1.16 | 0.27 | 0.96 | 0.07 |
| #1 GF 2 hours | 120 | 0.84 | 0.70 | 1.28 | 1.06 | 0.96 | 0.06 |
| #1 IF(pH 5.5) 0m | 130 | 2.45 | 0.24 | 3.73 | 0.37 | 23.56 | 0.22 |
| #1 IF(pH 5.5) 15m | 145 | 13.47 | 1.66 | 20.54 | 2.53 | 40.25 | 0.19 |
| #1 IF(pH 5.5) 30m | 160 | 24.57 | 0.01 | 37.46 | 0.02 | 61.83 | 0.18 |
| #1 IF(pH 5.5) 45m | 175 | 46.91 | 1.68 | 71.53 | 2.56 | 97.96 | 0.18 |
| #1 IF(pH 6.5) 15m | 190 | 53.75 | 1.00 | 81.96 | 1.52 | 108.48 | 1.32 |
| #1 IF(pH 6.5) 30m | 205 | 52.19 | 0.04 | 79.58 | 0.06 | 112.76 | 0.51 |
| #1 IF(pH 6.5) 45m | 220 | 55.91 | 0.43 | 85.25 | 0.65 | 111.44 | 0.28 |
| #1 IF(pH 6.5) 60m | 235 | 52.35 | 1.14 | 79.83 | 1.74 | 112.07 | 0.27 |
| #1 IF(pH 6.5) 75m | 250 | 50.97 | 1.14 | 77.72 | 1.74 | 110.82 | 0.08 |
| #1 IF(pH 6.5) 90m | 265 | 52.76 | 0.30 | 80.44 | 0.45 | 111.19 | 0.43 |
| #1 IF(pH 6.5) 120m | 295 | 54.79 | 0.17 | 83.54 | 0.26 | 111.57 | 0.09 |
| #1 Final 24h | 1440 | 54.19 | 0.47 | 82.63 | 0.72 | | |
| * the raw activity considering a total activity of 72.4% for tablet #1. | | | | | | | |

A)

B)

| Tablet: #2 (HPC subcoat + L 30 D 55) Sample | Time (m) | 1 | | 2 | | 3 | |
|---|---|---|---|---|---|---|---|
| | | Activity (%) | S.D. (%) | Activity as % of total (%) * | S.D. (%) | Release (%) | S.D. (%) |
| #2 GF 1 hour | 60 | 0.51 | 0.20 | 0.77 | 0.31 | 0.61 | 0.07 |
| #2 GF 2 hours | 120 | 1.37 | 0.39 | 2.09 | 0.60 | 0.38 | 0.10 |
| #2 IF(pH 5.5) 0m | 130 | 0.91 | 0.51 | 1.39 | 0.78 | 16.99 | 0.22 |
| #2 IF(pH 5.5) 15m | 145 | 13.98 | 1.34 | 21.31 | 2.05 | 17.98 | 0.21 |
| #2 IF(pH 5.5) 30m | 160 | 12.47 | 0.30 | 19.01 | 0.46 | 18.63 | 0.06 |
| #2 IF(pH 5.5) 45m | 175 | 21.14 | 0.05 | 32.24 | 0.07 | 21.60 | 0.10 |
| #2 IF(pH 6.5) 15m | 190 | 15.77 | 0.18 | 24.04 | 0.28 | 33.39 | 2.32 |
| #2 IF(pH 6.5) 30m | 205 | 35.30 | 3.16 | 53.83 | 4.83 | 41.18 | 0.35 |
| #2 IF(pH 6.5) 45m | 220 | 58.75 | 0.30 | 89.58 | 0.46 | 69.95 | 0.27 |
| #2 IF(pH 6.5) 60m | 235 | 49.73 | 0.92 | 75.83 | 1.40 | 99.07 | 0.12 |
| #2 IF(pH 6.5) 75m | 250 | 55.98 | 1.03 | 85.36 | 1.57 | 106.23 | 0.34 |
| #2 IF(pH 6.5) 90m | 265 | 58.29 | 1.52 | 88.89 | 2.32 | 110.59 | 0.68 |
| #2 IF(pH 6.5) 120m | 295 | 60.59 | 0.49 | 92.39 | 0.75 | 114.54 | 0.14 |
| #2 Final 24h | 1440 | 60.66 | 0.21 | 92.49 | 0.32 | | |

* the raw activity considering a total activity of 69.9% for tablet #2.

INTESTINAL ALKALINE PHOSPHATASE FORMULATIONS

CROSS-REFERENCE TO RELATED APPLICATIONS

This application is a National Stage Entry of International Patent Application No. PCT/US2019/023142, filed Mar. 20, 2019, which claims the benefit of U.S. Provisional Application No. 62/645,421, filed Mar. 20, 2018, the entire contents of which are hereby incorporated by reference in their entirety.

FIELD OF THE INVENTION

The present invention provides, in part, pharmaceutical dosage forms comprising alkaline phosphatase-based agents and uses thereof and methods of treatment for diseases, such as microbiome-related diseases.

DESCRIPTION OF THE TEXT FILE SUBMITTED ELECTRONICALLY

The contents of the text file submitted electronically herewith are incorporated herein by reference in their entirety: A computer readable format copy of the Sequence Listing (Filename: "SYN-035PC_ST25.txt"; Date created: Mar. 18, 2019; File size: 72.3 KB).

BACKGROUND

Alkaline phosphatases are dimeric metalloenzymes that catalyze the hydrolysis of phosphate esters and dephosphorylate a variety of target substrates at physiological and higher pHs. Alkaline phosphatases (APs) are found in prokaryotic as well as in eukaryotic organisms (e.g., in *E. coli* and mammals). Mammalian APs have been shown to play important roles in gut homeostasis, mucosal barrier function, promotion of commensal bacteria, and defense from pathogens. Mammalian APs exert their properties by primarily targeting lipopolysaccharide (LPS, a toll-like receptor-4 (TLR4) agonist), flagellin (a TLR5 agonist) and CpG DNA (a TLR9 agonist). APs also degrade intestine luminal nucleotide triphosphates (NTPs, e.g., ATP, GTP, etc.), which promotes the growth of good bacteria and reverses dysbiosis. Accordingly, APs may find clinical use as, for example, microbiome preserving agents for treating various gastrointestinal (GI) disorders upon localized delivery to targeted intestinal regions.

Further, formulating protein biologics are a particular challenge for treating patients that cannot easily be administered oral drugs. For example, powderizing and tableting protein biologics, including APs, is particularly challenging.

There remains a need for novel formulations and therapeutic uses of alkaline phosphatases for therapeutic use.

SUMMARY OF THE INVENTION

Accordingly, in some aspects, the present invention provides an enteric-coated formulation comprising an alkaline phosphatase (AP)-based agent and an enteric agent, wherein the formulation is in the form of a tablet, and the tablet solubilizes in a pH-dependent manner and is suitable for releasing a substantial and therapeutic amount of the AP-based agent in the intestines.

In some embodiments, the formulations are spray-dried and powderized with excipients in order to be compressed into tablets. For example, the present invention provides for formulations that are powderized and formed into tablets that exhibit resilience to friability and provide dissolution release profiles needed for targeting various regions of the intestines for treatment.

Other aspects and embodiments of the invention will be apparent from the following detailed description.

BRIEF DESCRIPTION OF THE DRAWINGS

FIG. 1 depicts sequences pertaining to alkaline phosphatase agents present in formulations described herein.

FIG. 2 depicts the stability of lyophilized IAP solution without additional sugar excipients by measuring IAP activity over time within the lyophilisates, using an endpoint assay for activity analysis.

FIG. 3 represents the IAP activity of spray dried material over time (stored at 4° C.), where the IAP activity is measured using endpoint analysis and kinetic analysis.

FIGS. 8A-B depict the weight change of Tablets #2 and #4 over time (FIG. 8A), and the % weight that was lost from Tablets #2 and #4 over time (FIG. 8B).

DETAILED DESCRIPTION OF THE INVENTION

A. Overview

Figure 4:
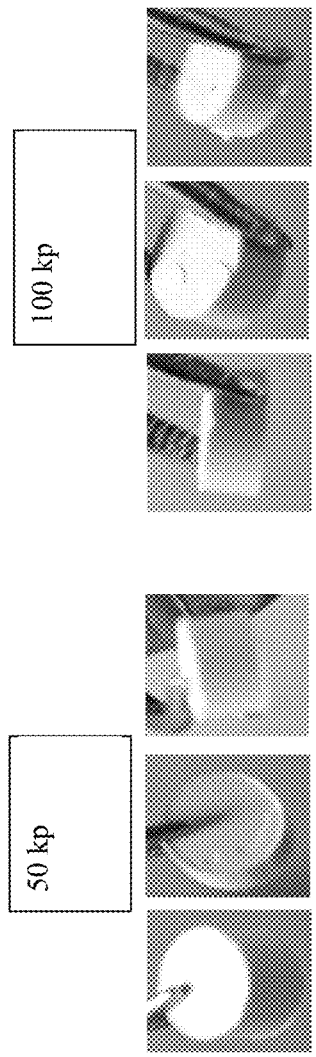
FIG. 4 depicts tablets formed through 50 kp and 100 kp of compression force, with an appreciable difference between the tablets in the heights of the tablets—the 100 kp tablet was shorter than the 50 kp tablet.

Treatment for gastrointestinal (GI) disorders is increasingly looking to the role of the microbiome as a mediator in preserving healthy functioning of the GI tract. As such, the role of alkaline phosphatases (APs) in promoting growth of good bacteria and reversing dysbiosis is a significant and growing field of study in the advancement of treatment options for GI disorders.

In particular, intestinal alkaline phosphatase (IAP) is an endogenous protein expressed by the intestinal epithelium that can be used to mitigate inflammation and maintain gut homeostasis. For example, loss of IAP expression or function is associated with increased intestinal inflammation, dysbiosis, bacterial translocation, and systemic inflammation. Its primary functions, among others, in maintaining intestinal homeostasis are generally recognized as the regulation of bicarbonate secretion and duodenal surface pH, long chain fatty acid absorption, mitigation of intestinal inflammation through detoxification of pathogen-associated molecular patterns, and regulation of the gut microbiome. Several substrates that are acted on by IAP's phosphatase functions include lipopolysaccharide (LPS), flagellin, CpG DNA, and nucleotide di- and tri-phosphates. Specifically, IAP is a target for therapeutics due to its ability to inactivate LPS, regulate the microbiome, tighten the gut barrier through enhanced expression of claudins and occludins, and affect metabolism of adenosine tri-phosphate and diphosphate (ATP and ADP).

Providing powder or tablet formulations that are both stable and exhibit sufficient dissolution/release profiles to allow for targeted release to the GI tract can be challenging due to the complicated nature of protein biologics.

Accordingly, the present invention provides formulations that are stable and withstand powderization and tableting as well as dissolve quickly and in the targeted locations in the gastrointestinal tract, e.g. the small intestine or large intestine.

B. Alkaline Phosphatase-Based Agents

The present invention is directed, in part, to pharmaceutical compositions, formulations, and uses of one or more alkaline phosphatase-based agents (AP-based agents). Illustrative AP-based agents that may be utilized in the present invention include, but are not limited to, intestinal alkaline phosphatase (IAP; e.g., human IAP, calf IAP or bovine IAP, chicken IAP, goat IAP), placental alkaline phosphatase (PLAP), placental-like alkaline phosphatase, germ cell alkaline phosphatase (GCAP), tissue non-specific alkaline phosphatase (TNAP; which is primarily found in the liver, kidney, and bone), bone alkaline phosphatase, liver alkaline phosphatase, kidney alkaline phosphatase, bacterial alkaline phosphatase, fungal alkaline phosphatase, shrimp alkaline phosphatase, modified IAP, recombinant IAP, or any polypeptide comprising alkaline phosphatase activity.

In various embodiments, the present invention contemplates the use of mammalian alkaline phosphatases including, but not limited to, intestinal alkaline phosphatase (IAP), placental alkaline phosphatase (PLAP), germ cell alkaline phosphatase (GCAP), and the tissue non-specific alkaline phosphatase (TNAP).

1. IAPs

In some embodiments, the AP-based agent is IAP. IAP is produced in the proximal small intestine and is bound to the enterocytes via a glycosyl phosphatidylinositol (GPI) anchor. Some IAP is released into the intestinal lumen in conjunction with vesicles shed by the cells and as soluble protein stripped from the cells via phospholipases. The enzyme then traverses the small and large intestine such that some active enzyme can be detected in the feces. In an embodiment, the IAP is human IAP (hIAP). In an embodiment, the IAP is calf IAP (cIAP), also known as bovine IAP (bIAP). There are multiple isozymes of bIAP, for example, with bIAP II and IV having higher specific activity than bIAP I. In an embodiment, the IAP is any one of the cIAP or bIAP isozymes (e.g., bIAP I, II, and IV). In an embodiment, the IAP is bIAP II. In another embodiment, the IAP is bIAP IV.

2. IAP Variants

Also included within the definition of IAPs are IAP variants. An IAP variant has at least one or more amino acid modifications, generally amino acid substitutions, as compared to the parental wild-type sequence. In some embodiments, an IAP of the invention comprises an amino sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the sequences disclosed herein. In addition, IAP variants retain most or all of their biochemical activity, measured as described herein.

Mammalian alkaline phosphatases are GPI anchored proteins. They have signal peptides and are translated into the secretory pathway. Once in the endoplasmic reticulum (ER), the proteins are glycosylated and folded. There are two disulfide bonds as well as a single free cysteine that is apparently not accessible on the surface. In the late ER, the carboxy terminus is removed and the GPI anchor is appended. GPI anchoring is therefore a process that occurs at the carboxy terminus of the alkaline phosphatase. The inclusion of stop codons at the anchor site enables secretion of biologically active protein (presumably the homodimer). While there is no consensus sequence, the carboxy terminus includes three amino acids, termed omega, omega+1, and omega+2 which are followed by a short stretch of hydrophilic amino acids and then a stretch of hydrophobic amino acids. Without wishing to be bound by theory, it is believed that the hydrophobicity is critical for embedding the carboxy terminus in the ER membrane. There, an enzymatic reaction replaces the carboxy terminus with the GPI anchor.

Within human placental alkaline phosphatase (hPLAP), the GPI anchor is attached at an aspartate in the sequence, DAAH. Similarly, hIAP, bIAP II, and bIAP IV also have this DAAH sequence conserved, potentially serving as the GPI anchor site. Mutational studies with hPLAP indicate that preventing GPI anchoring results in intracellular retention. In addition, mutations around the anchor site or in the hydrophobic domain either 1) prevent anchor attachment leading to intracellular retention or 2) do not block anchor attachment. Without wishing to be bound by theory, it is believed that the hydrophobic domain serves as a signal for GPI anchor attachment. Truncating or eliminating the hydrophobic domain leads to secretion. Finally, there is a single mutation in the hydrophobic domain that, in hPLAP, enables secretion of the protein with its hydrophobic domain intact.

In other embodiments, the AP-based agent of the invention is a secreted protein; that is, in some embodiments, the AP-based agent is not GPI anchored, leading to secretion rather than intracellular retention. This can be accomplished in several ways. In some embodiments, the AP-based agent may lack the GPI anchor site, e.g. have the DAAH site removed, leading to secretion. Alternatively, this can be accomplished in some embodiments, the AP-based agent comprises a stop codon that is inserted immediately before the GPI anchor site. In an embodiment, the AP-based agent comprises a stop codon after the aspartate in the DAAH consensus site (e.g., at amino acid 503 of hIAP and bIAP IV or amino acid 506 of bIAP II). FIG. 1 depicts HIAP with a stop codon (SEQ ID NO: 4), bIAP II with a stop codon (SEQ ID NO: 5), and bIAP IV with a stop codon (SEQ ID NO: 6). In an embodiment, the AP-based agent is bIAP IV and includes a stop codon after amino acid 508 to mimic a secreted PLAP construct as depicted in FIG. 1 (SEQ ID NO: 7).

3. Human IAP

In various embodiments, the AP-based agent is hIAP. In some embodiments, the AP-based agent is hIAP comprising the amino acid sequence of SEQ ID NO: 1 as depicted in FIG. 1 or a variant as described herein, as long as the hIAP variant retains at least 80, 85, 90, 95, 98 or 100% of the phosphatase activity as compared to the wild type enzyme using an assay as outlined herein.

Included within the definition of hIAP are amino acid modifications, with amino acid substitutions finding particular use in the present invention. For example, without wishing to be bound by theory, it is believed that a cysteine at the carboxy terminus of the AP-based agent (e.g., at position 500 of SEQ ID NO: 1) may interfere with protein folding. Accordingly, in some embodiments, the AP-based agent includes a mutation of the cysteine (e.g., at position 500 of SEQ ID NO: 1). In some embodiments, the cysteine is replaced with any amino acid, although glycine finds particular use in some embodiments. Furthermore, the C-terminal cysteine can also be deleted.

As will be appreciated by those in the art, additional amino acid modifications can be made in hIAP as discussed herein. For example, in some embodiments, a stop codon may be inserted after the aspartate in the DAAH consensus site (e.g., at amino acid 503 of hIAP). FIG. 1 depicts hIAP with an inserted stop codon (SEQ ID NO: 4).

4. Bovine IAPs

In some embodiments, the IAP is bovine IAP (bIAP).

a. bIAP II

In various embodiments, the AP-based agent is bovine IAP II (bIAP II) or a variant as described herein, as long as the bIAP variant retains at least 80, 85, 90, 95, 98 or 100% of the phosphatase activity using an assay as outlined herein. In an embodiment, the bIAP II comprises the signal peptide and carboxy terminus of bIAP I. In an embodiment, the bIAP II comprises an aspartate at position 248 (similar to bIAP IV). In an embodiment, the bIAP II comprises the amino acid sequence of SEQ ID NO: 2. FIG. 1 depicts BIAP II with 248D assignment—SEQ ID NO: 2. The signal peptide and sequence past 480 are derived from bIAP I.

Also included within the definition of bIAP II are amino acid variants as described herein. For example, in some embodiments, a stop codon may be inserted after the aspartate in the DAAH consensus site (e.g., at amino acid 506 of bIAP II). FIG. 1 depicts bIAP II with an inserted stop codon (SEQ ID NO: 5).

b. bIAP IV

In various embodiments, the AP-based agent is bIAP IV or a variant thereof as described herein, as long as the bIAP IV variant retains at least 80, 85, 90, 95, 98 or 100% of the phosphatase activity using an assay as outlined herein. In an embodiment, the bIAP IV comprises the amino acid sequence of SEQ ID NO: 3, as depicted in FIG. 1.

Also included within the definition of bIAP IV are amino acid variants as described herein. For example, in some embodiments, a stop codon may be inserted after the aspartate in the DAAH consensus site (e.g., at amino acid 503 of bIAP IV). FIG. 1 depicts bIAP IV with an inserted stop codon (SEQ ID NO: 6). In an embodiment, the AP-based agent is bIAP IV and includes a stop codon after amino acid 508 to mimic a secreted PLAP construct, as depicted in FIG. 1 (SEQ ID NO: 7).

5. Bacterial APs

In various embodiments, the present invention contemplates the use of bacterial alkaline phosphatases. In some embodiments, the AP-based agent of the invention is derived from *Bacillus subtilis*. *Bacillus subtilis* is a Gram-positive bacterium found in soil and the GI tract of humans. *Bacillus subtilis* secretes high levels of proteins into the environment and in the human GI tract that are properly folded. Without wishing to be bound by theory, it is believed that *Bacillus subtilis* secreted proteins in the GI tract may be resistant to degradation by common GI proteases. *Bacillus subtilis* expresses at high levels an alkaline phosphatase multigene family. Among those isozymes, alkaline phosphatase IV is responsible for the majority of total alkaline phosphatase expression and activity in *B. subtilis*. In some embodiments, the AP-based agent of the invention is derived from *Bacillus lichenformis*. In some embodiments, the AP-based agent of the invention is derived from *Escherichia coli*.

Accordingly, in an illustrative embodiment, the AP-based agent of the invention is derived from alkaline phosphatase IV of *Bacillus subtilis*. In an embodiment, the bacterial alkaline phosphatase may have nucleotide and amino acid sequences as depicted in FIG. 1, including *Bacillus subtilis* JH642 alkaline phosphatase IV, mature protein nucleotide sequence—SEQ ID NO: 16; and *Bacillus subtilis* JH642 alkaline phosphatase IV, mature protein amino acid sequence—SEQ ID NO: 17, or variants as described herein, as long as the hIAP variant retains at least 80, 85, 90, 95, 98 or 100% of the phosphatase activity using an assay as outlined herein.

In some embodiments, the AP-based agents include bacterial alkaline phosphatases that have one or more mutations that alter catalytic activity. In some embodiments, the bacterial alkaline phosphatases include one or more mutations such that their catalytic activity is similar or higher than mammalian alkaline phosphatases. In some embodiments, the bacterial alkaline phosphatases include one or more mutations that alter their de-phosphorylation profile. In an embodiment, the bacterial alkaline phosphatases of the invention exhibit similar de-phosphorylation profile as mammalian alkaline phosphatases. In some embodiments, the bacterial alkaline phosphatases include one or more mutations that alter their activity at higher pH. In an embodiment, the bacterial alkaline phosphatases of the invention exhibit similar activity at higher pH as mammalian alkaline phosphatases. In some embodiments, the bacterial alkaline phosphatases include one or more mutations that alter their metal requirements. In an embodiment, the bacterial alkaline phosphatases of the invention exhibit metal requirements (e.g., Mg) similar to mammalian alkaline phosphatases.

For example, in certain embodiments, the AP-based agent of the invention is derived from *Bacillus subtilis* JH642 alkaline phosphatase IV, and has one or more mutations at positions 101, 328, A330, and 374. For example, the AP-based agent may include one or more of the following mutations: D101A, W328H, A330N and G374C.

6. Fusion Proteins

In some embodiments, the AP-based agent comprises an alkaline phosphatase fused to a "fusion partner", which is a protein domain that is added either to the N- or C-terminus of the IAP domain, optionally including a linker. In some embodiments, the alkaline phosphatase is fused to a protein domain that promotes protein folding and/or protein purification and/or protein dimerization and/or protein stability. In various embodiments, the AP-based agent fusion protein has an extended serum half-life. In various embodiments, the AP-based agent of the invention is an Fc fusion protein.

In an embodiment, the alkaline phosphatase is fused to an immunoglobulin Fc domain and/or hinge region. In an embodiment, the AP-based agent of the invention comprises an alkaline phosphatase fused to the hinge region and/or Fc domain of IgG.

In various embodiments, the AP-based agent is fused to a Fc domain of IgG comprising one or more mutations. In some embodiments, the one or more mutations in the Fc domain of IgG function to increase serum half-life and longevity. In some embodiments, the Fc domain of IgG comprises one or more mutations at amino acid residues 251-256, 285-290, 308-314, 385-389 and 428-436, numbered according to the EU index as in Kabat (see Kabat et al., (1991) Sequences of Proteins of Immunological Interest, U.S. Public Health Service, National Institutes of Health, Washington, DC). In some embodiments, at least one of the amino acid substitutions in the Fc domain of IgG is at amino acid residue 252, 254, 256, 309, 311, 433 or 434. In an embodiment, the amino acid substitution at amino acid residue 252 is a substitution with tyrosine, phenylalanine, tryptophan or threonine. In an embodiment, the amino acid substitution at amino acid residue 254 is a substitution with threonine. In an embodiment, the amino acid substitution at amino acid residue 256 is a substitution with serine, arginine, glutamine, glutamic acid, aspartic acid, or threonine. In an embodiment, the amino acid substitution at amino acid residue 309 is a substitution with proline. In an embodiment, the amino acid substitution at amino acid residue 311 is a substitution with serine. In an embodiment, the amino acid substitution at amino acid residue 385 is a substitution with arginine, aspartic acid, serine, threonine, histidine, lysine, alanine or glycine. In an embodiment, the amino acid substitution at amino acid residue 386 is a substitution with threonine, proline, aspartic acid, serine, lysine, arginine, isoleucine, or methionine. In an embodiment, the amino acid substitution at amino acid residue 387 is a substitution with arginine, proline, histidine, serine, threonine, or alanine. In an embodiment, the amino acid substitution at amino acid residue 389 is a substitution with proline, serine or asparagine. In an embodiment, the amino acid substitution at amino acid residue 433 is a substitution with arginine, serine, isoleucine, proline, or glutamine. In an embodiment, the amino acid substitution at amino acid residue 434 is a substitution with histidine, phenylalanine, or tyrosine.

In some embodiments, the Fc domain of IgG comprises one or more mutations at amino acid residue 252, 254, 256, 433, 434, or 436. In an embodiment, the Fc domain of IgG includes a triple M252Y/S254T/T256E mutation or YTE mutation. In another embodiment, the Fc domain of IgG includes a triple H433K/N434F/Y436H mutation or KFH mutation. In a further embodiment, the Fc domain of IgG includes a YTE and KFH mutation in combination. Additional illustrative mutations in the Fc domain of IgG are described, for example, in Robbie, et al., Antimicrobial Agents and Chemotherapy (2013), 57(12):6147-6153, Dall'Acqua et al., JBC (2006), 281(33):23514-24, Dall'Acqua et al., Journal of Immunology (2002), 169:5171-80, and U.S. Pat. No. 7,083,784, the entire contents of which are hereby incorporated by reference. In various embodiments, the one or more mutations in the Fc domain of IgG increases affinity for the neonatal Fc receptor (FcRn). In some embodiments, the one or more mutations in the Fc domain of IgG increases affinity for FcRn at a pH of about 6.0, about 6.1, about 6.2, about 6.3, about 6.4, or about 6.5.

In various embodiments, the alkaline phosphatase is fused to one or more of PEG, XTENylation (e.g. as rPEG), polysialic acid (POLYXEN), albumin, elastin-like protein, elastin like protein (ELP), PAS, HAP, GLK, CTP, and transferrin. In various embodiments, the alkaline phosphatase is fused to one or more of the agents described in BioDrugs (2015) 29:215-239, the entire contents of which are hereby incorporated by reference.

a. Linkers

In an embodiment, the alkaline phosphatase is fused to a protein domain (e.g., an immunoglobulin Fc domain) via a linker to the GPI anchor site. For example, the alkaline phosphatase may be fused to a protein domain via the aspartate at the GPI anchor sequence. The invention contemplates the use of a variety of linker sequences. In various embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In some embodiments, the linker may be designed using linker designing databases and computer programs such as those described in Chen et al., (2013), Adv Drug Deliv Rev. 65(10):1357-1369 and Crasto et al., (2000), Protein Eng. 13(5):309-312, the entire contents of which are hereby incorporated by reference. In various embodiments, the linker may be functional. For example, without limitation, the linker may function to improve the folding and/or stability, improve the expression, improve the pharmacokinetics, and/or improve the bioactivity of the present AP-based agent. In another example, the linker may function to target the AP-based agent to a particular cell type or location.

In some embodiments, the linker is a polypeptide. In some embodiments, the linker is less than about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In some embodiments, the linker is flexible. In another embodiment, the linker is rigid.

In various embodiments, the linker is substantially comprised of glycine and serine residues (e.g. about 30%, or about 40%, or about 50%, or about 60%, or about 70%, or about 80%, or about 90%, or about 95%, or about 97% glycines and serines). In an embodiment, the linker sequence is GGSGGSGGGGSGGGS (SEQ ID NO: 18). Additional illustrative linkers include, but are not limited to, linkers having the sequence LE, GGGGS (SEQ ID NO: 19), (GGGGS)$_n$ (n=2-4) (SEQ ID NOs: 20-22), (Gly)$_8$ (SEQ ID NO: 23), (Gly)$_6$ (SEQ ID NO: 24), (EAAAK)$_n$ (n=1-3) (SEQ ID NOs: 25-27), A(EAAAK)$_n$A (n=2-5) (SEQ ID NOs: 28-31), AEAAAKEAAAKA SEQ ID NO: 32), A(EAAAK)$_4$ALEA(EAAAK)$_4$A (SEQ ID NO: 33), PAPAP (SEQ ID NO: 34), KESGSVSSEQLAQFRSLD (SEQ ID NO: 35), EGKSSGSGSESKST (SEQ ID NO: 36), GSAGSAAGSGEF (SEQ ID NO: 37), and (XP)$_n$, with X designating any amino acid, e.g., Ala, Lys, or Glu. In some embodiments, the linker is a hinge region of an antibody (e.g., of IgG, IgA, IgD, and IgE, inclusive of subclasses (e.g.

IgG1, IgG2, IgG3, and IgG4, and IgA1 and IgA2)). In some embodiments, the linker is a synthetic linker such as PEG.

Illustrative Fc fusion constructs of the invention include those depicted in FIG. 1, including BIAP II with Fc Fusion (SEQ ID NO: 8)—Fc domain underlined; and BIAP IV with Fc Fusion (SEQ ID NO: 9)—Fc domain underlined.

7. Pro-Enzyme Fusions

The invention additionally provides C-terminal fusions for pro-enzyme functions. Without wishing to be bound by theory, it is believed that mammalian alkaline phosphatases may also be generated as inactive pro-enzymes. This is because alkaline phosphatases can dephosphorylate ATP, so that activity in the ER could drain the ER of its major energy source. Without wishing to be bound by theory, it is believed that the inhibitory function is located to the carboxy terminus that would be relieved upon GPI anchor addition. Alternatively, other activities such as folding or metal (Zn or Mg) inclusion could control activity.

In various embodiments, the AP-based agent of the invention is a pro-enzyme. In an embodiment, the activity of the proenzyme is suppressed by a carboxy terminus. In an embodiment, protease removal of the carboxy terminus reactivates the enzymatic activity of the alkaline phosphatase. In an embodiment, the pro-enzyme is more efficiently secreted than the enzyme without the carboxy terminus.

A *Saccharomyces* alkaline phosphatase, Pho8, is produced as an inactive pro-enzyme. It is not GPI anchored, but is a transmembrane protein with its amino terminus extending out of a lysosome into the cytoplasm. Within the lysosome, an enzyme, PEP4, cleaves the carboxy terminus to activate the enzyme.

In some embodiments, for generation of the pro-enzyme, the native carboxy terminus of the alkaline phosphatase is replaced with the analogous sequence from hPLAP. In some embodiments, a mutation is made in the hydrophobic carboxy tail to promote protein secretion without cleavage of the carboxy terminus. In an illustrative embodiment, a single point mutation such as a substitution of leucine with e.g., arginine is generated in the hydrophobic carboxy terminus (e.g. ALLPLLAGTL is changed to e.g., ALLPLRAGTL) to result in secretion of the enzyme without removal of the carboxy terminus.

In an embodiment, the AP-based agent is altered to include a specific enzyme cleavage site which allows subsequent removal of the carboxy terminus. In an embodiment, the AP-based agent includes a protease cleavage site. Illustrative protease cleavage sites include, but are not limited to, cleavage sites recognized by furin, Rhinovirus 16 3C protease, factor Xa protease, trpysin, chymotrypsin, elastase, pepsin, papain subtilisin, thermolysin, V-8 protease, submaxillaris protease, clostripain, thrombin, collagenase, and any other endoproteases. In an alternative embodiment, the AP-based agent includes a cleavage site recognized by a digestive enzyme present in the GI tract. In such embodiments, the AP-based agent may be administered as a pro-drug that is subsequently activated in the GI tract.

In an illustrative embodiment, the proenzyme is a proenzyme of bIAP IV having sequences depicted in FIG. 1, including BIAP IV with the hPLAP Carboxy Terminus and Mutation for Unprocessed Secretion and RV3C Cleavage (at . . . LEVLFQGP . . . ) (SEQ ID NO: 10); and BIAP IV with hPLAP Carboxy Terminus and Mutation for Unprocessed Secretion and FXa Cleavage (at . . . IEGR . . . ) (SEQ ID NO: 11).

8. Expression Variants

In various embodiments, the AP-based agent of the invention is efficiently expressed and secreted from a host cell. In an embodiment, the AP-based agent of the invention is efficiently transcribed in a host cell. In another embodiment, the AP-based agent exhibits enhanced RNA stability and/or transport in a host cell. In another embodiment, the AP-based agent is efficiently translated in a host cell. In another embodiment, the AP-based agent exhibits enhanced protein stability.

In various embodiments, the AP-based agents are efficiently expressed in a host cell. In an embodiment, the Kozak sequence of the DNA construct encoding the AP-based agent is optimized. The Kozak sequence is the nucleotide sequence flanking the ATG start codon that instructs the ribosome to start translation. There is flexibility in the design of a Kozak sequence, but one canonical sequence is GCCGCCACCATGG (SEQ ID NO: 38). The purine in the −3 position and the G in the +4 position are the most important bases for translation initiation. For hIAP, bIAP II, and bIAP IV, the second amino acid, that is, the one after the initiator methionine, is glutamine. Codons for glutamine all have a C in the first position. Thus, their Kozak sequences all have an ATGC sequence. Accordingly, in various embodiments, the ATGC sequence is changed to ATGG. This can be achieved by changing the second amino acid to a glycine, alanine, valine, aspartate, or glutamic acid, all of whose codons have a G in the first position. These amino acids may be compatible with signal peptide function. In alternative embodiments, the entire signal peptide is substituted for peptide having a canonical Kozak sequence and is derived from a highly expressed protein such as an immunoglobulin.

In various embodiments, the signal peptide of the AP-based agent may be deleted and/or substituted. For example, the signal peptide may be deleted, mutated, and/or substituted (e.g., with another signal peptide) to ensure protein expression.

In some embodiments, the DNA construct encoding the AP-based agent of the invention comprises untranslated DNA sequences. Such sequences include an intron, which may be heterologous to the IAP protein or native to the IAP protein including the native first and/or second intron and/or a native 3' UTR. Without wishing to be bound by theory, it is believed that include of these sequences enhance protein expression by stabilizing the mRNA. Accordingly, in various embodiments, the DNA construct encoding the AP-based agent of the invention comprises the 5'UTR and/or the 3'UTR. Provided in FIG. 1 are illustrative IAP DNA sequences with a first intron and a 3'UTR, including hIAP with native first intron (shown as bolded and underlined)—SEQ ID NO: 12; hIAP with native 3' UTR (shown as bolded and underlined)—SEQ ID NO: 13; bIAP IV with the first intron from bIAP I (shown as bolded and underlined)—SEQ ID NO: 14; and bIAP IV with the 3' UTR from bIAP I (shown as bolded and underlined)—SEQ ID NO: 15.

In various embodiments, the AP-based agent of the invention comprises a nucleotide sequence having at least about 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with any of the sequences disclosed herein.

In various embodiments, the AP-based agent of the invention may comprise an amino acid sequence having one or more amino acid mutations relative to any of the protein sequences described herein. In some embodiments, the one or more amino acid mutations may be independently selected from substitutions, insertions, deletions, and truncations.

In various embodiments, the substitutions may also include non-classical amino acids (e.g. selenocysteine, pyrrolysine, N-formylmethionine β-alanine, GABA and S-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, 7-Abu, F-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β-methyl amino acids, C α-methyl amino acids, N α-methyl amino acids, and amino acid analogs in general).

Mutations may be made to the AP-based agent of the invention to select for agents with desired characteristics. For examples, mutations may be made to generate AP-based agents with enhanced catalytic activity or protein stability. In various embodiments, directed evolution may be utilized to generate AP-based agents of the invention. For example, error-prone PCR and DNA shuffling may be used to identify mutations in the bacterial alkaline phosphatases that confer enhanced activity.

C. Methods of Making the APs of the Invention

The IAPs of the invention are made using standard molecular biology techniques. For example, nucleic acid compositions encoding the IAPs of the invention are also provided, as well as expression vectors containing the nucleic acids and host cells transformed with the nucleic acid and/or expression vector compositions. As will be appreciated by those in the art, the protein sequences depicted herein can be encoded by any number of possible nucleic acid sequences, due to the degeneracy of the genetic code.

As is known in the art, the nucleic acids encoding the components of the invention can be incorporated into expression vectors as is known in the art, and depending on the host cells, used to produce the IAP compositions of the invention. Generally, the nucleic acids are operably linked to any number of regulatory elements (promoters, origin of replication, selectable markers, ribosomal binding sites, inducers, etc.). The expression vectors can be extra-chromosomal or integrating vectors.

The nucleic acids and/or expression vectors of the invention are then transformed into any number of different types of host cells as is well known in the art, including mammalian, bacterial, yeast, insect and/or fungal cells, with mammalian cells (e.g. CHO cells), finding use in many embodiments.

The IAPs of the invention are made by culturing host cells comprising the expression vector(s) as is well known in the art. Once produced, traditional purification steps are done.

D. Formulations

In various embodiments, the formulation is resistant to compression and therefore suitable for tableting. Generally, the AP agents are provided in a powder form that is then tableted, e.g., by physical compression of dried materials.

In various embodiments, the AP-based agent of the invention is stable and/or active in the GI tract, e.g. in one or more of the mouth, esophagus, stomach, duodenum, small intestine, duodenum, jejunum, ileum, large intestine, colon transversum, colon descendens, colon ascendens, colon sigmoidenum, cecum, and rectum. In a specific embodiment, the alkaline phosphatase is stable in the large intestine, optionally selected from one or more of colon transversum, colon descendens, colon ascendens, colon sigmoidenum and cecum. In a specific embodiment, the alkaline phosphatase is stable in the small intestine, optionally selected from one or more of duodenum, jejunum, and ileum. In some embodiments, the alkaline phosphatase is resistant to proteases in the GI tract, including for example, the small intestine. In some embodiments, the alkaline phosphatase is substantially active at a pH of about 5.0 or above. For example, the alkaline phosphatase may be substantially active at a pH of about 6.0 to about 12, e.g. about 6.0, or about 6.1, or about 6.2, or about 6.3, or about 6.4, or about 6.5, or about 6.6, or about 6.7, or about 6.8, or about 6.9, or about 7.0, or about 7.1, or about 7.2, or about 7.3, or about 7.4, or about 7.5, or about 8.0, or about 8.5, or about 9.0, or about 9.5, or about 10.0, or about 10.5, or about 11.0, or about 11.5, or about 12.0 (including, for example, via formulation, as described herein). In some embodiments, stable refers to an enzyme that has a long enough half-life and maintains sufficient activity for therapeutic effectiveness.

In various embodiments, the AP-based agent of the invention is stable in chyme. In order to assess AP-based agent stability in chyme, samples of AP-based agents are incubated in human chyme at 37 C. Stability is then evaluated by assessing aliquots withdrawn from the incubated samples at 0, 0.5, 1, 2, 3, 4, 5, and 6 hours for AP activity using a para-nitrophenyl phosphate (pNPP) AP substrate. Different chyme specimens can be used for evaluation of stability, including mixed chyme samples. Chyme samples are characterized for pH, liquid content, and protease activity.

In some embodiments, the AP-based agent of the invention is active in formulations until at least 2 weeks, 4 weeks, 8 weeks, 12 weeks, 16 weeks, 20 weeks, 24 weeks, 28 weeks, 32 weeks, 36 weeks, 40 weeks, 44 weeks, 48 weeks, or 52 weeks in storage. In some embodiments, the AP-based agent is active at least at 45%, at least at 50%, at least at 55%, at least at 60%, at least at 65% at least at 70%, or at least at 75% against the Sigma standard. In other words, in some embodiments, the AP-based agent of the invention maintains activity after a given number of weeks of storage.

In some embodiments, the AP-based agent described herein includes derivatives that are modified, i.e., by the covalent attachment of any type of molecule to the alkaline phosphatase such that covalent attachment does not prevent the activity of the enzyme. For example, but not by way of limitation, derivatives include alkaline phosphatases that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out, including, but not limited to specific chemical cleavage, acetylation, formylation, metabolic synthesis of tunicamycin, etc. Additionally, the derivative can contain one or more non-classical amino acids. In various embodiments, the AP-based agent is glycosylated to ensure proper protein folding.

1. Pharmaceutically Acceptable Salts

The AP-based agent described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, Journal of Pharmaceutical Science, 66, 2-19 (1977) and The Handbook of Pharmaceutical Salts; Properties, Selection, and Use. P. H. Stahl and C. G. Wermuth (eds.), Verlag, Zurich (Switzerland) 2002, which are hereby incorporated by reference in their entirety.

The term "pharmaceutically acceptable salt" also refers to a salt of the alkaline phosphatases having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

In some embodiments, the compositions described herein are in the form of pharmaceutically acceptable salts. In various embodiments, the formulation comprises 5%, about 10%, about 15%, about 20%, about 25%, about 30%, about 31%, about 32%, about 33%, about 34%, about 35%, about 36%, about 37%, about 38%, about 39%, about 40%, about 41%, about 42%, about 43%, about 43%, about 44%, about 45%, about 46%, about 47%, about 48%, about 49%, or about 50% by weight pharmaceutically acceptable salts.

2. Pharmaceutical Excipients

Further, any AP-based agent described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, cellulose, hypromellose, lactose, sucrose, trehalose, malt, rice, flour, chalk, silica gel, sodium stearate, glycerol monostearate, talc, sodium chloride, dried skim milk, glycerol, propylene, glycol, povidone, crosspovidone, water, ethanol and the like. Any agent described herein, if desired, can also comprise minor amounts of wetting or emulsifying agents, or pH buffering agents. Other examples of suitable pharmaceutical excipients are described in Remington's Pharmaceutical Sciences 1447-1676 (Alfonso R. Gennaro eds., 19th ed. 1995), incorporated herein by reference.

A suitable pharmaceutical excipient for the purposes of tableting can be Ludipress (Lactose, povidone, crospovidone; CAS-No.: 5989-81-1+9003-39-8). The following is incorporated by reference in their entireties: (1) Schmidt and Rubensdorfer, "Evaluation of Ludipress as a 'Multipurpose Excipient' for Direct Compression: Part I: Poweder Characteristics and Tableting Properties" *Drug Development and Industrial Pharmacy* Vol. 20 (1994) pp. 2899-2925; and (2) Schmidt and Rubensdorfer, "Evaluation of Ludipress as a 'Multipurpose Excipient' for Direct Compression: Part II: Interactive Blending and Tableting with Micronized Glibenclamide" *Drug Development and Industrial Pharmacy* Vol. 20 (1994) pp. 2927-2952.

Where necessary, the AP-based agent and/or pharmaceutical compositions (and/or additional therapeutic agents) can include a solubilizing agent. Also, the agents can be delivered with a suitable vehicle or delivery device. Combination therapies outlined herein can be co-delivered in a single delivery vehicle or delivery device.

The present invention provides the described AP-based agent and/or pharmaceutical compositions (and/or additional therapeutic agents) in various formulations. Any AP-based agent and/or pharmaceutical composition (and/or additional therapeutic agents) described herein can take the form of tablets, pills, pellets, capsules, capsules containing liquids, capsules containing multiparticulates, powders, solutions, emulsion, drops, suppositories, emulsions, aerosols, sprays, suspensions, delayed-release formulations, sustained-release formulations, controlled-release formulations, or any other form suitable for use.

The formulations comprising the AP-based agent and/or pharmaceutical compositions (and/or additional therapeutic agents) may conveniently be presented in unit dosage forms. For example, the dosage forms may be prepared by methods which include the step of bringing the therapeutic agents into association with a carrier, which constitutes one or more accessory ingredients. For example, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by press tableting).

In one embodiment, the AP-based agent (and/or additional therapeutic agents) described herein is formulated as a composition adapted for a mode of administration described herein.

In one embodiment, the AP-based agent and/or pharmaceutical compositions (and/or additional therapeutic agents) described herein are formulated as compositions adapted for oral administration. Compositions for oral delivery can be in the form of tablets, lozenges, aqueous or oily suspensions, granules, powders, sprinkles, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration to provide a sustained action over an extended period of time. Selectively permeable membranes surrounding an osmotically active agent driving any alkaline phosphatase (and/or additional therapeutic agents) described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include excipients such as mannitol, lactose, starch, magnesium stearate, sodium saccharin, cellulose, ethacrylic acid and derivative polymers thereof, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

In various embodiments, the AP-based agent and/or pharmaceutical compositions (and/or additional therapeutic agent) are formulated as solid dosage forms such as tablets, dispersible powders, granules, and capsules. In one embodiment, the AP-based agent and/or pharmaceutical compositions (and/or additional therapeutic agent) are formulated as a capsule. In another embodiment, the AP-based agent and/or pharmaceutical compositions (and/or additional therapeutic agent) are formulated as a tablet. In yet another embodiment, the AP-based agent and/or pharmaceutical compositions (and/or additional therapeutic agent) are formulated as a soft-gel capsule. In a further embodiment, the AP-based agent and/or pharmaceutical compositions (and/or additional therapeutic agent) are formulated as a gelatin capsule.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents.

In various embodiments, the formulations of the AP-based agents may additionally comprise a pharmaceutically acceptable carrier or excipient. As one skilled in the art will recognize, the formulations can be in any suitable form appropriate for the desired use and route of administration.

In some dosage forms, the agents described herein are mixed with at least one inert, pharmaceutically acceptable excipient or carrier such as sodium citrate, dicalcium phosphate, etc., and/or a) fillers or extenders such as starches, lactose, sucrose, glucose, mannitol, silicic acid, microcrystalline cellulose, and Bakers Special Sugar, etc., b) binders such as, for example, carboxymethylcellulose, alginates, gelatin, polyvinylpyrrolidone, sucrose, acacia, polyvinyl alcohol, polyvinylpyrrolidone, methylcellulose, hydroxypropyl cellulose (HPC), and hydroxymethyl cellulose etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., and i) lubricants such as talc, calcium stearate, magnesium stearate, solid polyethylene glycols, sodium lauryl sulfate, glyceryl behenate, etc., and mixtures of such excipients. One of skill in the art will recognize that particular excipients may have two or more functions in the oral dosage form. In the case of an oral dosage form, for example, a capsule or a tablet, the dosage form may also comprise buffering agents.

3. Surface Active Agents

The formulation can additionally include a surface active agent. Surface active agents suitable for use in the present invention include, but are not limited to, any pharmaceutically acceptable, non-toxic surfactant. Classes of surfactants suitable for use in the compositions of the invention include, but are not limited to polyethoxylated fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-olyoxypropylene block copolymers, sorbitan fatty acid esters, lower alcohol fatty acid esters, ionic surfactants, and mixtures thereof. In some embodiments, compositions of the invention may comprise one or more surfactants including, but not limited to, sodium lauryl sulfate, polysorbate 20, polysorbate 40, polysorbate 60, polysorbate 80, and triethyl citrate.

The formulation can also contain pharmaceutically acceptable plasticizers to obtain the desired mechanical properties such as flexibility and hardness. Such plasticizers include, but are not limited to, triacetin, citric acid esters, triethyl citrate, phthalic acid esters, dibutyl sebacate, cetyl alcohol, polyethylene glycols, polysorbates or other plasticizers.

The formulation can also include one or more application solvents. Some of the more common solvents that can be used to apply, for example, a delayed-release coating composition include isopropyl alcohol, acetone, methylene chloride and the like.

The formulation can also include one or more alkaline materials. Alkaline material suitable for use in compositions of the invention include, but are not limited to, sodium, potassium, calcium, magnesium and aluminum salts of acids such as phosphoric acid, carbonic acid, citric acid and other aluminum/magnesium compounds. In addition, the alkaline material may be selected from antacid materials such as aluminum hydroxides, calcium hydroxides, magnesium hydroxides and magnesium oxide.

In various embodiments, the formulation can additionally include magnesium and/or zinc. Without wishing to be bound by theory, the inclusion of magnesium and/or zinc in the formulation promotes protein folding (e.g., dimer formation) and bioactivity of the AP-based agent. In some embodiments, the formulation can include magnesium at a concentration of from about 1 μM to greater than 500 mM (e.g., from about 1 μM to more than 5 mM), inclusive of all ranges and values therebetween. In an embodiment, the magnesium is present in the formulation at 1.0 mM. In some embodiments, the formulation can include zinc at a concentration of about 1 μM to greater than 100 mM (e.g., from about 1 μM to more than 1 mM), inclusive of all ranges and values therebetween. In an embodiment, the zinc is present in the formulation at 0.1 mM. In various embodiments, the formulation of the present invention is substantially free of metal chelators.

In various embodiments, the pH of the formulation ensures that the AP-based agent is properly folded (e.g., dimer formation) and is bioactive. In some embodiments, the formulation is maintained at a pH such that the amino acids which coordinate the binding of magnesium and/or zinc within the AP-based agent are not protonated. Protonation of such coordinating amino acids may lead to loss of metal ions and bioactivity and dimer disassociation. In various embodiments, the pH of the formulation is greater than about 6, about 6.5, about 7, about 7.5, about 8, about 8.5, about 9, about 9.5, about 10, about 10.5, about 11, about 11.5, or about 12.

Besides inert diluents, the oral compositions can also include adjuvants such as sweetening, flavoring, and perfuming agents.

4. Delivery

Various methods may be used to formulate and/or deliver the agents described herein to a location of interest. For example, the alkaline phosphatase and/or pharmaceutical compositions (and/or additional therapeutic agents) described herein may be formulated for delivery to the GI tract. The GI tract includes organs of the digestive system such as mouth, esophagus, stomach, duodenum, small intestine, large intestine and rectum and includes all subsections thereof (e.g. the small intestine may include the duodenum, jejunum and ileum; the large intestine may include the colon transversum, colon descendens, colon ascendens, colon sigmoidenum and cecum). For example, the alkaline phosphatases and/or pharmaceutical compositions (and/or additional therapeutic agents) described herein may be formulated for delivery to one or more of the stomach, small intestine, large intestine and rectum and includes all subsections thereof (e.g. duodenum, jejunum and ileum, colon transversum, colon descendens, colon ascendens, colon sigmoidenum and cecum). In some embodiments, the compositions described herein may be formulated to deliver to the upper or lower GI tract. In an embodiment, the alkaline phosphatases and/or pharmaceutical compositions (and/or additional therapeutic agents) may be administered to a subject, by, for example, directly or indirectly contacting the mucosal tissues of the GI tract.

In various embodiments, the administration of the AP-based agent and/or pharmaceutical compositions (and/or additional therapeutic agents) is into the GI tract via, for example, oral delivery, nasogastral tube, intestinal intubation (e.g. an enteral tube or feeding tube such as, for example, a jejunal tube or gastro-jejunal tube, etc.), direct infusion (e.g., duodenal infusion), endoscopy, colonoscopy, or enema.

For example, in various embodiments, the present invention provides modified release formulations comprising at least one AP-based agent (and/or additional therapeutic agents), wherein the formulation releases a substantial amount of the AP-based agent (and/or additional therapeutic agents) into one or more regions of the GI tract. For example, the formulation may release at least about 60% of the AP-based agent after the stomach and into one or more regions of the GI tract.

In various embodiments, the modified-release formulation of the present invention releases at least 60% of the AP-based agent (or additional therapeutic agents) after the stomach into one or more regions of the intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (or additional therapeutic agents) in the intestines.

In various embodiments, the modified-release formulation of the present invention releases at least 60% of the AP-based agent (or additional therapeutic agents) in the small intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (or additional therapeutic agents) in the small intestine (e.g., one or more of duodenum, jejunum, ileum, and ileocecal junction).

In various embodiments, the modified-release formulation of the present invention releases at least 60% of the AP-based agent (or additional therapeutic agents) in the large intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the AP-based agent (or additional therapeutic agents) in the large intestine (e.g., one or more of cecum, ascending, transverse, descending or sigmoid portions of the colon, and rectum).

In various embodiments, the modified-release formulation does not substantially release the AP-based agent (or additional therapeutic agents) in the stomach.

In certain embodiments, the modified-release formulation releases the AP-based agent (or additional therapeutic agents) above a specific pH. For example, in some embodiments, the modified-release formulation is substantially stable in an acidic environment and substantially unstable (e.g., dissolves rapidly or is physically unstable) in a near neutral to alkaline environment. In some embodiments, stability is indicative of not substantially releasing while instability is indicative of substantially releasing. For example, in some embodiments, the modified-release formulation is substantially stable at a pH of about 7.0 or less, or about 6.5 or less, or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. In some embodiments, the present formulations are stable in lower pH areas and therefore do not substantially release in, for example, the stomach. In some embodiments, the modified-release formulation is substantially stable at a pH of about 1 to about 5 or lower and substantially unstable at pH values that are greater. In these embodiments, the modified-release formulation does not substantially release in the stomach. In these embodiments, the modified-release formulation substantially releases in the small intestine (e.g. one or more of the duodenum, jejunum, and ileum) and/or large intestine (e.g. one or more of the cecum, ascending colon, transverse colon, descending colon, and sigmoid colon). In some embodiments, modified-release formulation is substantially stable at a pH of about 4 to about 7 or lower and consequentially is substantially unstable at pH values that are greater and therefore is not substantially released in the stomach and/or proximal small intestine (e.g. one or more of the duodenum, jejunum). In these embodiments, the modified-release formulation substantially releases in the distal small intestine or large intestine (e.g. one or more of the cecum, ascending colon, transverse colon, descending colon, and sigmoid colon). In various embodiments, the pH values recited herein may be adjusted as known in the art to account for the state of the subject, e.g. whether in a fasting or postprandial state.

In some embodiments, the modified-release formulation is substantially stable in gastric fluid and substantially unstable in intestinal fluid and, accordingly, is substantially released in the small intestine (e.g. one or more of the duodenum, jejunum, and ileum) and/or large intestine (e.g. one or more of the cecum, ascending colon, transverse colon, descending colon, and sigmoid colon).

In some embodiments, the modified-release formulation is stable in gastric fluid or stable in acidic environments. These modified-release formulations release about 30% or less by weight of the alkaline phosphatase and/or additional therapeutic agent in the modified-release formulation in gastric fluid with a pH of about 4 to about 5 or less, or simulated gastric fluid with a pH of about 4 to about 5 or less, in about 15, or about 30, or about 45, or about 60, or about 90 minutes. Modified-release formulations of the of the invention may release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of the alkaline phosphatase and/or additional therapeutic agent in the modified-release formulation in gastric fluid with a pH of 4-5, or less or simulated gastric fluid with a pH of 4-5 or less, in about 15, or about 30, or about 45, or about 60, or about 90 minutes. Modified-release formulations of the invention may release about 1%, about 2%, about 3%, about 4%, about 5%, about 6%, about 7%, about 8%, about 9%, or about 10% by weight of the total alkaline phosphatase and/or additional therapeutic agent in the modified-release formulation in gastric fluid with a pH of 5 or less, or simulated gastric fluid with a pH of 5 or less, in about 15, or about 30, or about 45, or about 60, or about 90 minutes.

In some embodiments, the modified-release formulation is unstable in intestinal fluid. These modified-release formulations release about 70% or more by weight of the alkaline phosphatase and/or additional therapeutic agent in the modified-release formulation in intestinal fluid or simulated intestinal fluid in about 15, or about 30, or about 45, or about 60, or about 90 minutes. In some embodiments, the modified-release formulation is unstable in near neutral to alkaline environments. These modified-release formulations release about 70% or more by weight of the alkaline phosphatase and/or additional therapeutic agent in the modified-release formulation in intestinal fluid with a pH of about 4-5 or greater, or simulated intestinal fluid with a pH of about 4-5 or greater, in about 15, or about 30, or about 45, or about 60, or about 90 minutes. A modified-release formulation that is unstable in near neutral or alkaline environments may release 70% or more by weight of alkaline phosphatase and/or additional therapeutic agent in the modified-release formulation in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

In various embodiments, the modified-release formulation of the invention is substantially stable in chyme. For example, there is, in some embodiments, a loss of less than about 50% or about 40%, or about 30%, or about 20%, or about 10% of AP-based agent activity in about 10, or 9, or 8, or 7, or 6, or 5, or 4, or 3, or 2, or 1 hour from administration.

In various embodiments, the modified-release formulations of the present invention are designed for immediate release (e.g. upon ingestion). In various embodiments, the modified-release formulations may have sustained-release profiles, i.e. slow release of the active ingredient(s) in the body (e.g., GI tract) over an extended period of time. In various embodiments, the modified-release formulations may have a delayed-release profile, i.e. not immediately release the active ingredient(s) upon ingestion; rather, postponement of the release of the active ingredient(s) until the composition is lower in the GI tract; for example, for release in the small intestine (e.g., one or more of duodenum, jejunum, ileum) or the large intestine (e.g., one or more of cecum, ascending, transverse, descending or sigmoid portions of the colon, and rectum). For example, a composition can be enteric-coated to delay release of the active ingredient(s) until it reaches the small intestine or large intestine.

5. Enteric Coating

In various embodiments, the present powder formulations (e.g. AP-based agent as a powder) is coated to provide protection of the active agent in the GI tract, including the stomach. For example, in some embodiments, the present powder formulations can be encapsulated in an enterically-coated capsule. Additionally, in some embodiments, the powder formulations (e.g. AP-based agent as a powder) itself is coated with one or more coatings, e.g. one or more modified-release coatings as described herein (e.g. after a step of granulating the powder). Further, in some embodiments, the present powder formulations (e.g. AP-based agent as a powder) can be compressed into a tablet that is enterically coated.

In various embodiments, the modified-release formulation of the present invention may utilize one or more modified-release coatings such as delayed-release coatings to provide for effective, delayed yet substantial delivery of the alkaline phosphatase to the GI tract together with, optionally, additional therapeutic agents.

In various embodiments, the modified-release formulation of the present invention may utilize one or more modified-release coatings such as delayed-release coatings to provide for effective, delayed yet substantial delivery of the alkaline phosphatase to the intestines together with, optionally, other additional therapeutic agents.

In one embodiment, the delayed-release coating includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly (methacrylic acid, methylmethacrylate), hydroxypropyl methylcellulose acetate succinate, cellulose acetate trimellitate, shellac or other suitable enteric coating polymers. The polymers are described in international pharmacopeias such as Ph. Eur., USP/NF, DMF, and JPE. The EUDRAGIT®-type polymers include, for example, EUDRAGIT® FS 30D, L 30 D-55, L 100-55, L 100, L 12,5, L 12,5 P, RL 30 D, RL PO, RL 100, RL 12,5, RS 30 D, RS PO, RS 100, RS 12,5, NE 30 D, NE 40 D, NM 30 D, S 100, S 12,5, and S 12,5 P. Similar polymers include Kollicoat® MAE 30 DP and Kollicoat® MAE 100 P. In some embodiments, one or more of EUDRAGIT® FS 30D, L 30 D-55, L 100-55, L 100, L 12,5, L 12,5 P RL 30 D, RL PO, RL 100, RL 12,5, RS 30 D, RS PO, RS 100, RS 12,5, NE 30 D, NE 40 D, NM 30 D, S 100, S 12,5 S 12,5 P, Kollicoat® MAE 30 DP and Kollicoat® MAE 100 P is used. The following are incorporated by reference in their entireties: (1) Thakral et al., "Eudragit®: A technology evaluation" *Expert Opinion on Drug Delivery* Vol. 10 (2013) pp. 131-149; (2) Niranjan Patra et al., "Pharmaceutical significance of Eudragit: A review," *Future Journal of Pharmaceutical Sciences* Vol. 3 (10.1016/j.fjps.2017.02.001); (3) Sonje, Abhijit and Chandra, Amrish, "Comprehencive review on eudragit polymers," *International Research Journal of Pharmacy* Vol. 4 (10.7897/2230-8407.04515). In various embodiments, the enteric agent may be a combination of the foregoing solutions or dispersions. In an embodiment, the delayed-release coating includes the enteric agent EUDRAGIT® L 100.

By way of non-limiting example, there are various EUDRAGIT formulations that dissolve at rising pH, with formulations that dissolve at pH>5.5 (EUDRAGIT L30 D-550), pH>6.0 (EUDRAGIT L12, 5), and pH>7.0 (EUDRAGIT FS 30D). Since the ileum has the highest pH in the small intestine, ranging from 7.3 to 7.8, the use of EUDRAGIT FS 30D as an enteric agent, may delay dissolution until the ileum thereby localizing the release of the AP-based agent to the ileum. However, the jejunum has a pH that can range from 6.6 to 7.4, therefore, various EUDRAGIT formulations can be used to target release to this segment of the intestine. The different types of EUDRAGIT can be combined with each other, or multiple different types of EUDRAGIT coatings can be combined to fine tune the dissolution profile to achieve targeted delivery to achieve function. For example, EUDRAGIT L100, EUDRAGIT S100, and triethyl citrate may be mixed together at a ratio of, for example, about 72.7/18.2/9.1, to form a coating that substantially releases at a pH of greater than about 6.2. In another example, EUDRAGIT L100, EUDRAGIT S100, and triethyl citrate may be mixed together at a ratio of, for example, about 30/60.9/9, to form a coating that substantially releases at a pH of greater than about 6.7. In a further example, DuoCoat™ (Kuecept, Ltd.) may be used that uses two coatings of enteric polymers (like EUDRAGIT), an outer layer, and an inner layer of partially neutralized enteric polymer and a buffer agent. The DuoCoat™ technology allows more rapid release of the therapeutic agent initiated at the targeted pH compared to a single coating of the enteric polymer (Liu et al., 2010, European J. Pharmaceutics and Biopharmaceuticals 47:311, the entire contents of all of which are incorporated herein by reference). Release was demonstrated to be targeted to the ileum and/or ileoceacal junction in 10 healthy volunteers (Varum et al., 2013, European J. Pharmaceutics and Biopharmaceuticals 84:573, the entire contents of all of which are incorporated herein by reference).

In certain embodiments, one or more coating system additives are used with the enteric agent. For example, one or more PlasACRYL™ additives may be used as an anti-tacking agent coating additive. Illustrative PlasACRYL™ additives include, but are not limited to PlasACRYL™ HTP20 and PlasACRYL™ T20.

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, and EUDRAGIT NE®. Insoluble polymers useful in the present invention include polyvinyl esters, polyvinyl acetals, polyacrylic acid esters, butadiene styrene copolymers, and the like. In one embodiment, colonic delivery is achieved by use of a slowly-eroding wax plug (e.g., various PEGS, including for example, PEG6000) or pectin. In an embodiment, the present invention contemplates the use of a delayed-release coating that degrade as a function of time which comprises a swell layer comprising croscarmellos sodium and hydroxyproplycellulose. In such embodiment, the formulation may further include an osmotic rupture coating that comprises ethylcellulose such as ethylcellulose dispersions.

Alternatively, the stability of the modified-release formulation can be enzyme-dependent. Delayed-release coatings that are enzyme dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine, such as galactomannans. Also, the stability of the modified-release formulation can be dependent on enzyme stability in the presence of a microbial enzyme present in the gut flora. For example, in various embodiments, the delayed-release coating may be degraded by a microbial enzyme present in the gut flora. In an embodiment, the delayed-release coating may be degraded by bacteria present in the small intestine. In another embodiment, the delayed-release coating may be degraded by bacteria present in the large intestine.

In various embodiments, the modified release formulation is designed for release in the colon. Various colon-specific delivery approaches may be utilized. For example, the modified release formulation may be formulated using a colon-specific drug delivery system (CODES) as described for example, in Li et al., AAPS PharmSciTech (2002), 3(4): 1-9, the entire contents of which are incorporated herein by reference. Drug release in such a system is triggered by colonic microflora coupled with pH-sensitive polymer coatings. For example, the formulation may be designed as a core tablet with three layers of polymer. The first coating is an acid-soluble polymer (e.g., EUDRAGIT E), the outer coating is enteric, along with a hydroxypropyl methylcellulose barrier layer interposed in between. In another embodiment, colon delivery may be achieved by formulating the alkaline phosphatase (and/or additional therapeutic agent) with specific polymers that degrade in the colon such as, for example, pectin. The pectin may be further gelled or cross-linked with a cation such as a zinc cation. In an embodiment, the formulation is in the form of ionically crosslinked pectin beads which are further coated with a polymer (e.g., EUDRAGIT polymer). Additional colon specific formulations include, but are not limited to, pressure-controlled drug delivery systems (prepared with, for example, ethylcellulose) and osmotic controlled drug delivery systems (i.e., ORDS-CT).

Formulations for colon specific delivery of the AP-based agent (and/or additional therapeutic agents), as described herein, may be evaluated using, for example, in vitro dissolution tests. For example, parallel dissolution studies in different buffers may be undertaken to characterize the behavior of the formulations at different pH levels. Alternatively, in vitro enzymatic tests may be carried out. For example, the formulations may be incubated in fermenters containing suitable medium for bacteria, and the amount of drug released at different time intervals is determined. Drug release studies can also be done in buffer medium containing enzymes or rat or guinea pig or rabbit cecal contents and the amount of drug released in a particular time is determined. In a further embodiment, in vivo evaluations may be carried out using animal models such as dogs, guinea pigs, rats, and pigs. Further, clinical evaluation of colon specific drug delivery formulations may be evaluated by calculating drug delivery index (DDI) which considers the relative ratio of RCE (relative colonic tissue exposure to the drug) to RSC (relative amount of drug in blood i.e. that is relative systemic exposure to the drug). Higher drug DDI indicates better colon drug delivery. Absorption of drugs from the colon may be monitored by colonoscopy and intubation.

In various embodiments, the present formulations provide for substantial uniform dissolution of the AP-based agent (and/or additional therapeutic agent) in the area of release in the GI tract. In an embodiment, the present formulation minimizes patchy or heterogeneous release of the AP-based agent.

In various embodiments, the present invention provides for modified-release formulations that release multiple doses of the AP-based agent, at different locations along the intestines, at different times, and/or at different pH. In an illustrative embodiment, the modified-release formulation comprises a first dose of the AP-based agent and a second dose of the AP-based agent, wherein the first dose and the second dose are released at different locations along the intestines, at different times, and/or at different pH. For example, the first dose is released at the duodenum, and the second dose is released at the ileum. In another example, the first dose is released at the jejunum, and the second dose is released at the ileum. In other embodiments, the first dose is released at a location along the small intestine (e.g., the duodenum), while the second dose is released along the large intestine (e.g., the ascending colon). In various embodiments, the modified-release formulation may release at least one dose, at least two doses, at least three doses, at least four doses, at least five doses, at least six doses, at least seven doses, or at least eight doses of the AP-based agent at different locations along the intestines, at different times, and/or at different pH.

In various embodiments, the formulations of the present invention take the form of those as described in one or more of U.S. Pat. Nos. 8,535,713 and 8,911,777 and US Patent Publication Nos. 20120141585, 20120141531, 2006/001896, 2007/0292523, 2008/0020018, 2008/0113031, 2010/0203120, 2010/0255087, 2010/0297221, 2011/0052645, 2013/0243873, 2013/0330411, 2014/0017313, and 2014/0234418, the contents of which are hereby incorporated by reference in their entirety.

In various embodiments, the formulations of the present invention take the form of those described in one or more of U.S. Pat. Nos. 4,196,564; 4,196,565; 4,247,006; 4,250,997; 4,268,265; 5,317,849; 6,572,892; 7,712,634; 8,074,835; 8,398,912; 8,440,224; 8,557,294; 8,646,591; 8,739,812; 8,810,259; 8,852,631; and 8,911,788 and US Patent Publication Nos. 2014/0302132; 2014/0227357; 20140088202; 20130287842; 2013/0295188; 2013/0307962; and 20130184290, the contents of which are hereby incorporated by reference in their entirety.

In various embodiments, the process of formulating the AP-based agent is sufficiently gentle such that the tertiary structure of the AP-based agent (e.g., dimeric structure) is substantially intact. In various embodiments, the process of formulating the AP-based agent includes a step of refolding the AP-based agent. In such embodiments, the step of refolding the AP-based agent may include the addition of magnesium and/or cyclodextrin.

In various embodiments, the modified-release formulation is a modified-release powder formulation.

In various embodiments, the modified-release formulation including AP-based agents described herein, and variants thereof, and/or additional therapeutic agents is administered orally.

Suitable dosage forms for oral use include, for example, solid dosage forms such as tablets, capsules, powders, and granules. In various embodiments, the modified-release formulation is in the form of powders. In some embodiments, the powdered formulations of the present invention can be added to food (e.g. juices, strained and/or pureed foods (e.g. fruits, vegetables), sauces, infant formulas, milk, etc.). In various embodiments, the modified-release formulation is packaged in the form of a sachet. In various embodiments, the modified-release formulation is in the form of tablets. In an embodiment, the modified-release formulation is in the form of tablets comprising powders. In various embodiments, the modified-release formulation is in the form of capsules. In an embodiment, the modified-release formulation is in the form of capsules comprising powders.

In various embodiments, the modified-release formulation of the invention is in the form of powders. In various embodiments, the powders are formed by spray drying and/or by spray-dried dispersion (SDD) technology. In some embodiments, the powders comprising AP-based agents are formed by dissolving AP-based agents and polymers in a solvent and then spray-drying the solution. The resulting powder comprises the AP-based agents dispersed within a solid polymeric matrix.

Various types of polymers may be used for the modified-release formulation of the invention. In some embodiments, the polymer is an enteric polymer that is substantially stable in acidic environments and substantially unstable in near neutral to alkaline environments. In an embodiment, the enteric polymer is substantially stable in gastric fluid.

Illustrative polymers include, but are not limited to, copovidone, polyvinyl caprolactam-polyvinyl acetate-polyethyleneglycol copolymer, poly(vinylpyrrolidinone) (PVP), hydroxypropylmethylcellulose or hypromellose (HPMC), hypromellose phthalate (HPMCP), hydroxypropylmethylcellulose or hypromellose acetate succinate (HPMCAS), methacrylate/methacrylic acid copolymer, and mixtures thereof. In an embodiment, the polymer is HPMCAS. In various embodiments, the poymer is HPMCAS LF, LG, MF, MG, HF, or HG. In an embodiment, the polymer is HPMCAS-LF.

6. Buffers

Various types of solvents/buffers may be used for preparation of the powders of the invention. In an embodiment, the solvents/buffers are organic solvents/buffers. Illustrative solvents/buffers that may be used to dissolve the AP-based agent and polymer prior to spray-drying include, but are not limited to, ethanol, methanol, acetone, IPA, tetrahydrafuran, dichloromethane, and mixtures thereof. In various embodiments, the solvent used is water such as distilled DI water. In various embodiments, the buffer used is monosodium phosphate monohydrate.

In some embodiments, enzyme co-factors including zinc and magnesium are used. In an embodiment, the enzyme co-factor zinc is used. In an embodiment, the zinc is provided as zinc sulfate heptahydrate. In another embodiment, the enzyme co-factor magnesium is used. In an embodiment, the magnesium is provided as magnesium sulfate heptahydrate.

In some embodiments, the formulation includes a protein stabilizer such as trehalose, sucrose, lactose, mannitol, Tween 80, or polyvinyl alcohol. In an embodiment, the stabilizer is sucrose. In an embodiment, the stabilizer is lactose.

In some embodiments, surfactants may be included for the preparation of the powders of the invention. The surfactants may be used as solubilizers or emulsifying agents. Illustrative surfactants include, but are not limited to, vitamin E polyethylene glycol succinate, sorbitan monostearate—60/80, polysorbate 20, polysorbate 80, and polyoxyl 40 hydrogenated castor oil.

In various embodiments, the powders comprising AP-based agents becomes a gel. In various embodiments, the powders comprising an AP-based agent becomes a gel in the intestines. In various embodiments, the AP-based agent is released from the gel into one or more regions of the intestines. In various embodiments, at pH values greater than about 5 (e.g. about 5, or 6, or 7, or 8, or 9) the gel transforms back into the solution phase and releases the AP enzyme. In various embodiments, the gel is used to control the release of the AP-based agent in the intestines. In some embodiments, the AP-based agent is released from the gel into one or more of the group consisting of the small intestine, duodenum, jejunum, ileum, large intestine, colon transversum, colon descendens, colon ascendens, colon sigmoidenum, cecum, and rectum.

In various embodiments, the formulation of the present invention is in the form of powders comprising the AP-based agent dispersed within a solid polymeric matrix. In some embodiments, the powders are formed by dissolving AP-based agent and polymers in a solvent to form a solution that is subsequently spray-dried. In various embodiments, the solution for spray-drying comprises about 0.1-1% by weight of AP-based agent. For example, the AP-based agent may be present about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, or about 1.0% by weight. In some embodiments, the solution comprises about 1-10% by weight a polymer (e.g., HPMCAS-LF). For example, the polymer may be present at about 1%, about 2%, about 3%, about 4%, about 5%, about 6%, about 7%, about 8%, about 9%, or about 10% by weight. In some embodiment, the solution comprises about 0.05-0.5% by weight buffer (e.g., monosodium phosphate monohydrate). For example, the buffer may be present at about 0.05%, about 0.06%, about 0.07%, about 0.08%, about 0.09%, about 0.10%, about 0.11%, about 0.12%, about 0.13%, about 0.14%, about 0.15%, about 0.16%, about 0.17%, about 0.18%, about 0.19%, about 0.20%, about 0.25%, about 0.30%, about 0.35%, about 0.40%, about 0.45%, or about 0.50% by weight. In some embodiment, the solution comprises about 0.001-0.01% by weight zinc (e.g., zinc sulfate heptahhydrate). For example, the zinc may be present at about 0.001%, about 0.002%, about 0.003%, about 0.004%, about 0.005%, about 0.006%, about 0.007%, about 0.008%, about 0.009%, or about 0.01% by weight. In some embodiment, the solution comprises about 0.01-0.1% by weight magnesium (e.g., magnesium sulfate heptahhydrate). For example, the magnesium may be present at about 0.01%, about 0.02%, about 0.03%, about 0.04%, about 0.05%, about 0.06%, about 0.07%, about 0.08%, about 0.09%, or about 0.1% by weight. In some embodiment, the solution comprises about 0.1-1% by weight a protein stabilizer (e.g., trehalose). For example, the protein stabilizer may be present at about 0.1%, about 0.2%, about 0.3%, about 0.4%, about 0.5%, about 0.6%, about 0.7%, about 0.8%, about 0.9%, or about 1% by weight. In some embodiments, the solution comprises about 90-99.9% by weight solvent (e.g., water). For example, the solvent may be present at about 90%, about 91%, about 92%, about 93%, about 94%, about 95%, about 96%, about 97%, about 98%, or about 99% by weight.

In various embodiments, the modified-release formulation of the invention is in the form of tablets or capsules. In some embodiments, the modified-release formulation is in the form of tablets or capsules comprising the powders of the invention. A variety of approaches for generating tablets or capsules may be utilized to include powders of the invention. In some embodiments, tablets of the invention are generated by granulation such as dry granulation. In such embodiments, the powders are pre-compressed and the resulting tablet or slug is milled to yield granules. Alternatively, the powders are pre-compressed with pressure rolls to yield granules. In yet other embodiments, the powders are encapsulated into capsules. In an embodiment, the capsule is a gelatin capsule, such as a hard gelatin capsule. In another embodiment, the capsule is a hydroxypropyl methylcellulose (HPMC) capsule.

In various embodiments, the tablets or capsules comprise a delayed-release coating that includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly(methacrylic acid, methylmethacrylate), hydroxypropyl methylcellulose acetate succinate, cellulose acetate trimellitate, shellac or other suitable enteric coating polymers. The polymers are described in international pharmacopeias such as Ph. Eur., USP/NF, DMF, and PE. The EUDRAGIT®-type polymers include, for example, EUDRAGIT® FS 30D, L 30 D-55, L 100-55, L 100, L 12,5, L 12,5 P, RL 30 D, RL PO, RL 100, RL 12,5, RS 30 D, RS PO, RS 100, RS 12,5, NE 30 D, NE 40 D, NM 30 D, S 100, S 12,5, and S 12,5 P. Similar polymers include Kollicoat® MAE 30 DP and Kollicoat® MAE 100 P. In some embodiments, one or more of EUDRAGIT® FS 30D, L 30 D-55, L 100-55, L 100, L 12,5, L 12,5 P RL 30 D, RL PO, RL 100, RL 12,5, RS 30 D, RS PO, RS 100, RS 12,5, NE 30 D, NE 40 D, NM 30 D, S 100, S 12,5 S 12,5 P, Kollicoat® MAE 30 DP and Kollicoat® MAE 100 P is used. In various embodiments, the enteric agent may be a combination of the foregoing solutions or dispersions. In an embodiment, the delayed-release coating includes the enteric agent EUDRAGIT® L 100. In some embodiments, the tablet or capsule is coated with the enteric agent at a coating weight of about 1-20% such as about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% coating weight.

E. Formulation Embodiments

For the purpose of illustration, various embodiments of the present invention comprise particular formulations. The below are not intended to be limiting.

In specific embodiments, the components of the formulations of the present invention are first mixed as a liquid solution (minus the magnesium-stearate) and then spray-dried together into a powder (SD powder). The spray-dried material is then compressed into a tablet (with magnesium-stearate). Tablets are then enteric-coated with either one or two layers of enteric coating.

In various embodiments, the formulation of the present invention is in the form of a tablet (e.g., formed by compressing spray-dried material (SD powder)) comprising an active alkaline phosphatase and enteric-coated. In such embodiments, the tablet formulation comprises between about 5-50% by weight of alkaline phosphatase (e.g. bIAP, or the other alkaline phophatase agents described herein, and variants thereof). For example, the alkaline phosphatase (e.g. bIAP, or the other alkaline phosphatase agents described herein, and variants thereof) may be present at about 5%, about 10%, about 15%, about 20%, about 25%, about 30%, about 31%, about 32%, about 33%, about 34%, about 35%, about 36%, about 37%, about 38%, about 39%, about 40%, about 41%, about 42%, about 43%, about 43%, about 44%, about 45%, about 46%, about 47%, about 48%, about 49%, or about 50% by weight.

In some embodiments, the tablet formulation comprises between about 5-50% by weight sugar excipient (e.g., lactose, sucrose, or trehalose). For example, the sugar excipient may be present at about 5%, about 10%, about 15%, about 20%, about 25%, about 30%, about 31%, about 32%, about 33%, about 34%, about 35%, about 36%, about 37%, about 38%, about 39%, about 40%, about 41%, about 42%, about 43%, about 43%, about 44%, about 45%, about 46%, about 47%, about 48%, about 49%, or about 50% by weight.

In various embodiments, the tablet formulations comprise between about 5-50% by weight a binder excipient (e.g., hydroxypropylcellulose (HPC) or hydroxypropyl methylcellulose acetate succinate (HPMCAS, optionally the HF, MF, or LF form)). For example, the binder excipient may be present at about 5%, about 6%, about 7%, about 8%, about 9%, or about 10%, about 15%, about 20%, about 25%, about 26%, about 27%, about 28%, about 29%, about 30%, about 31%, about 32%, about 33%, about 34%, or about 35% by weight. In some embodiments, the tablet formulation does not comprise hydroxypropyl methylcellulose.

In some embodiments, the tablet formulation comprises between about 1-10% by weight of Ludipress (Lactose, povidone, crospovidone; CAS-No.: 5989-81-1+9003-39-8). For example, the Ludipress may be present at about 1%, about 2%, about 3%, about 4%, about 5%, about 6%, about 7%, about 8%, about 9%, or about 10% by weight.

In some embodiments, the tablet formulation further comprises between about 1-10% by weight buffer salts, optionally selected from a Tris base, magnesium chloride, zinc sulfate. For example, the buffer salts may be present at about 1%, about 2%, about 3%, about 4%, about 5%, about 6%, about 7%, about 8%, about 9%, or about 10% by weight.

In some embodiments, the tablet formulation comprises between about 1-2% by weight of magnesium-stearate. For example, the magnesium-stearate may be present at about 1.1%, about 1.2%, about 1.3%, about 1.4%, about 1.5%, about 1.6%, about 1.7%, about 1.8%, about 1.9%, or about 2% by weight. The weight as described herein refers to the total weight of all components.

In some embodiments, the tablet formulation comprises an enteric coating. In various embodiments the tablet formulation comprises between about 10-30% by weight of an enteric polymer (e.g., EUDRAGIT L30D 55 (poly(methacrylic acid-ethyl acrylate copolymer) 1:1)). For example, the enteric polymer (e.g., EUDRAGIT L30D 55) may be present at about about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% by weight. In some embodiments, the tablet formulation comprises a second enteric coating. In various embodiments, the tablet formulation comprises between about 1-30% by weight of a second enteric polymer (e.g., EUDRAGIT S100). For example, the second enteric polymer (e.g., EUDRAGIT S100) may be present at about about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% by weight. In some embodiments, the tablet formulation comprises a first coating that serves as a subcoat prior to application of an enteric coating.

In various embodiments the tablet formulation comprises between about 1-30% by weight subcoat (e.g., HPC). For example, the subcoat (e.g., HPC) may be present at about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% by weight.

1. Formulation 1

In various embodiments, the formulation of the present invention is in the form of a tablet (e.g., formed by compressing spray-dried material (SD powder)) comprising an alkaline phosphatase and enterically coated. In certain embodiments, the kinetics of release differ based on formulation and enteric coating. For example, in some embodiments, the Formulation 1 tablets exhibit a sustained release profile. Specifically, Formulation 1 tablets may dissolve and release some of the bIAP between a pH of 5.5 and pH 6.5, as assessed by in vitro dissolution assay, and in such embodiments, the bIAP is about 39% released from the tablet after 45 minutes of dissolution at pH 5.5 and about 72% released bIAP at 150 minutes at pH 6.5.

In some embodiments, the tablet formulation comprises between about 20-40%, about 25-35%, about 28-34%, about 29-33%, about 30-32%, or about 30-35% by weight of alkaline phosphatase (e.g. bIAP, or the other alkaline phophatase agents described herein, and variants thereof). In some embodiments, the tablet formulation comprises between about 20-40%, about 25-35%, about 28-34%, about 29-33%, about 30-32%, or about 30-35% by weight sugar excipient (e.g., lactose, sucrose, or trehalose). In various embodiments, the tablet formulations comprise between about 20-40%, about 25-35%, about 28-34%, about 29-33%, about 30-32%, or about 30-35% by weight a binder excipient (e.g., hydroxypropylcellulose (HPC) or hydroxypropyl methylcellulose acetate succinate (HPMCAS, optionally L, M, or H grade)). In some embodiments, the tablet formulation does not comprise hydroxypropyl methylcellulose acetate succinate. In some embodiments, the tablet formulation further comprises between about 1-13%, about 2-12%, about 3-11%, about 4-10%, about 5-9%, or about 6-8% by weight buffer salts, optionally selected from a Tris base, magnesium chloride, zinc sulfate. In some embodiments, the tablet formulation comprises between about 0.5-2%, about 0.5-1.5%, or about 1-2% by weight of magnesium-stearate. The weight as described herein refers to the total weight of all components.

In various embodiments, the tablet formulation further comprises an enteric coating. In various embodiments, the enteric coating is Eudragit L 30 D 55. In some embodiments, the tablet formulation further comprises two coatings, wherein the first coating comprises a HPC (hydroxypropyl cellulose) subcoat and the second coating comprises Eudragit L 30 D 55. In some embodiments, the tablet coating comprises between about 5-15%, about 6-14%, about 7-13%, about 8-12%, about 9-10% weight gain of an enteric polymer (e.g., EUDRAGIT L 30 D 55). In various embodiments, the tablet is coated with about a 7%, 8%, 9%, 10%, 11% or 12% weight gain of Eudragit L 30 D 55. In some embodiments, the tablet coating comprises between 1-15%, between 2-14%, between 3-13%, between 4-12%, between 5-11%, between 6-10%, between 7-9% weight gain of a HPC subcoat that serves to isolate the IAP from the acidic EUDRAGIT L 30 D 55 polymer. In various embodiments, the tablet is coated with about a 5%, 6%, 7%, 8% or 9% weight gain HPC subcoat.

In some embodiments, the tablet formulation comprises about 31% by weight of the alkaline phosphatase (e.g. bIAP, or the other alkaline phosphatase agents described herein, and variants thereof); about 31% by weight sucrose; about 31% by weight a binder excipient (e.g., hydroxypropylcellulose (HPC) or hydroxypropyl methylcellulose acetate succinate (HPMCAS, optionally L, M, or H grade)); about 1% by weight of magnesium-stearate; and about 7% by weight buffer salts, optionally selected from a Tris base, magnesium chloride, zinc sulfate. The weight as described herein refers to the total weight of all components.

In particular embodiments, the tablet formulation comprises about 30.65% by weight of the alkaline phosphatase (e.g. bIAP, or the other alkaline phosphatase agents described herein, and variants thereof); about 30.65% by weight sucrose; about 30.65% by weight a binder excipient (e.g., hydroxypropylcellulose (HPC) or hydroxypropyl methylcellulose acetate succinate (HPMCAS, optionally L, M, or H grade)); about 1% by weight of magnesium-stearate; and about 7.05% by weight buffer salts, optionally selected from a Tris base, magnesium chloride, zinc sulfate. The weight as described herein refers to the total weight of all components.

2. Formulation 2

In various embodiments, the formulation of the present invention is in the form of a tablet (e.g., formed by compressing spray-dried material (SD powder)) comprising an alkaline phosphatase and enterically coated. In certain embodiments, the kinetics of release differ based on formulation and enteric coating. For example, in some embodiments, Formulation 2 tablets exhibit fast-release, or burst, profiles. Specifically, Formulation 2 tablets may dissolve and release some of the bIAP between a pH of 5.5 and pH 6.5, as assessed by in vitro dissolution assay, and in such embodiments, the bIAP is 66% released from the tablet after 15 minutes of dissolution at pH 5.5 and then 86% released bIAP at 30 minutes at pH 6.5.

In some embodiments, the tablet formulation comprises about 25-45%, about 30-45%, about 30-40%, about 32.5-38.5%, about 33.5-37.5%, about 34.5-36.5%, or about 35-40% by weight of alkaline phosphatase (e.g. bIAP, or the other alkaline phophatase agents described herein, and variants thereof). In some embodiments, the tablet formulation comprises about 25-45%, about 30-45%, about 30-40%, about 32.5-38.5%, about 33.5-37.5%, about 34.5-36.5%, or about 35-40% by weight excipient (e.g., lactose, sucrose, or trehalose). In various embodiments, the tablet formulations comprise about 5-15%, about 6-14%, about 7-13%, about 8-12%, about 9-11% or about 10-15% by weight a binder excipient (e.g., hydroxypropylcellulose (HPC) or hydroxypropyl methylcellulose acetate succinate (HPMCAS, optionally L, M, or H grade)). In some embodiments, the tablet formulation does not comprise hydroxypropyl methylcellulose acetate succinate. In some embodiments, the tablet formulation comprises about 5-15%, about 6-14%, about 7-13%, about 8-12%, about 9-11% or about 10-15% by weight of Ludipress. In some embodiments, the tablet formulation further comprises about 3-13%, about 4-12%, about 5-11%, about 6-10%, or about 7-9% by weight buffer salts, optionally selected from a Tris base, magnesium chloride, zinc sulfate. In some embodiments, the tablet formulation comprises about 0.5-2%, about 0.5-1.5%, or about 1-2% by weight of magnesium-stearate. The weight as described herein refers to the total weight of all components.

In various embodiments, the tablet formulation further comprises an enteric coating. In various embodiments, the enteric coating is Eudragit L 30 D 55. In some embodiments, the tablet formulation further comprises two coatings, wherein the first coating comprises a HPC (hydroxypropyl cellulose) subcoat and the second coating comprises Eudragit L 30 D 55. In various embodiments, the HPC subcoats serves to isolate the IAP from the acidic Eudragit L 30 D 55 polymer. In some embodiments, the tablet coating comprises about 5-15%, about 6-14%, about 7-13%, about 8-12%, about 9-10% weight gain of an enteric polymer (e.g., EUDRAGIT L 30 D 55). In various embodiments, the tablet is coated with about a 7%, 8%, 9%, 10%, 11% or 12% weight gain of Eudragit L 30 D 55. In some embodiments, the tablet coating comprises between 1-15%, between 2-14%, between 3-13%, between 4-12%, between 5-11%, between 6-10%, between 7-9% weight gain of a HPC subcoat that serves to isolate the IAP from the acidic EUDRAGIT L 30 D 55 polymer. In various embodiments, the tablet is coated with about a 5%, 6%, 7%, 8% or 9% weight gain HPC subcoat.

In some embodiments, the tablet formulation comprises about 35.5% by weight of the alkaline phosphatase (e.g. bIAP, or the other alkaline phosphatase agents described herein, and variants thereof); about 35.5% by weight sucrose; about 10% by weight a binder excipient (e.g., hydroxypropylcellulose (HPC) or hydroxypropyl methylcellulose acetate succinate (HPMCAS, optionally L, M, or H grade)); about 1% by weight of magnesium-stearate; about 10% Ludipress; about 8% by weight buffer salts, optionally selected from a Tris base, magnesium chloride, zinc sulfate. The weight as described herein refers to the total weight of all components.

In particular embodiments, the tablet formulation comprises about 35.52% by weight of the alkaline phosphatase (e.g. bIAP, or the other alkaline phosphatase agents described herein, and variants thereof); about 35.52% by weight sucrose; about 9.9% by weight a binder excipient (e.g., hydroxypropylcellulose (HPC) or hydroxypropyl methylcellulose acetate succinate (HPMCAS, optionally L, M, or H grade)); about 1% by weight of magnesium-stearate; about 9.9% Ludipress; and about 8.17% by weight buffer salts, optionally selected from a Tris base, magnesium chloride, zinc sulfate. The weight as described herein refers to the total weight of all components.

3. Formulation 3

In various embodiments, the formulation of the present invention is in the form of a tablet (e.g., formed by compressing spray-dried material (SD powder)) comprising an alkaline phosphatase and enterically coated. In certain embodiments, the kinetics of release differ based on formulation and enteric coating. For example, in some embodiments, Formulation 3 tablets exhibit release profiles between sustained and fast-release. Specifically, Formulation 3 tablets may dissolve and release some of the the bIAP between a pH of 5.5 and pH 6.5, as assessed by in vitro dissolution assay, and in such embodiments, the bIAP is 43% released from the tablet after 30 minutes of dissolution at pH 5.5 and then 83% released bIAP at 75 minutes at pH 6.5.

In some embodiments, the uncoated tablet formulation comprises about 30-45%, about 35-45%, about 35-40%, about 36-44%, about 37-43%, about 38-42%, or about 39-41% by weight of alkaline phosphatase (e.g. bIAP, or the other alkaline phophatase agents described herein, and variants thereof). In some embodiments, the tablet formulation comprises about 30-45%, about 35-45%, about 35-40%, about 36-44%, about 37-43%, about 38-42%, or about 39-41% by weight sugar excipient (e.g., lactose, sucrose, or trehalose). In some embodiments, the tablet formulation does not comprise hydroxypropyl methylcellulose acetate succinate. In some embodiments, the tablet formulation comprises about 5-15%, about 6-14%, about 7-13%, about 8-12%, about 9-11% or about 10-15% by weight of Ludipress. In some embodiments, the tablet formulation further comprises about 3-15%, about 4-14%, about 5-13%, about 6-12%, or about 7-11% by weight buffer salts, optionally selected from a Tris base, magnesium chloride, zinc sulfate. In some embodiments, the tablet formulation comprises about 0.5-2%, about 0.5-1.5%, or about 1-2% by weight of magnesium-stearate. The weight as described herein refers to the total weight of all components.

In various embodiments, the tablet formulation further comprises an enteric coating. In various embodiments, the enteric coating is Eudragit L 30 D 55. In some embodiments, the tablet formulation further comprises two coatings, wherein the first coating comprises a HPC (hydroxypropyl cellulose) subcoat and the second coating comprises Eudragit L 30 D 55. In various embodiments, the HPC subcoats serves to isolate the IAP from the acidic Eudragit L 30 D 55 polymer. In some embodiments, the tablet coating comprises about 5-15%, about 6-14%, about 7-13%, about 8-12%, about 9-10% weight gain of an enteric polymer (e.g., EUDRAGIT L 30 D 55). In various embodiments, the tablet is coated with about a 7%, 8%, 9%, 10%, 11% or 12% weight gain of Eudragit L 30 D 55. In some embodiments, the tablet coating comprises between 1-15%, between 2-14%, between 3-13%, between 4-12%, between 5-11%, between 6-10%, between 7-9% weight gain of a HPC subcoat that serves to isolate the IAP from the acidic EUDRAGIT L 30 D 55 polymer. In various embodiments, the tablet is coated with about a 5%, 6%, 7%, 8% or 9% weight gain HPC subcoat.

In some embodiments, the tablet formulation comprises about 40% by weight of the alkaline phosphatase (e.g. bIAP, or the other alkaline phosphatase agents described herein, and variants thereof); about 40% by weight sucrose; 0% by weight a binder excipient (e.g., hydroxypropylcellulose (HPC) or hydroxypropyl methylcellulose acetate succinate (HPMCAS, optionally L, M, or H grade)); about 1% by weight of magnesium-stearate; about 10% Ludipress; and about 9% by weight buffer salts, optionally selected from a Tris base, magnesium chloride, zinc sulfate. The weight as described herein refers to the total weight of all components.

In particular embodiments, the tablet formulation uncoated comprises about 39.96% by weight of the alkaline phosphatase (e.g. bIAP, or the other alkaline phosphatase agents described herein, and variants thereof); about 39.96% by weight sucrose; 0% by weight a binder excipient (e.g., hydroxypropylcellulose (HPC) or hydroxypropyl methylcellulose acetate succinate (HPMCAS, optionally L, M, or H grade)); about 1% by weight of magnesium-stearate; about 9.9% Ludipress; and about 9.19% by weight buffer salts, optionally selected from a Tris base, magnesium chloride, zinc sulfate. The weight as described herein refers to the total weight of all components.

In some embodiments, the coated tablet (coated with 15% Eudragit L30D 55) formulation comprises about 25-45%, about 27-43%, about 29-41%, about 30-40%, about 32-38%, or about 33-37% by weight of alkaline phosphatase ((e.g. bIAP, or the other alkaline phosphatase agents described herein, and variants thereof). In some embodiments, the coated tablet formulation comprises about 25-45%, about 27-43%, about 29-41%, about 30-40%, about 32-38%, or about 33-37% by weight sugar excipient (e.g., lactose, sucrose, or trehalose). In some embodiments, the coated tablet formulation comprises about 5-11%, about 6-10%, about 7-9%, about 7-8% or about 8-10% by weight buffer salts, optionally chosen from a Tris base, magnesium chloride, and zinc sulfate. In some embodiments, the coated tablet formulation comprises about 5-12%, about 6-11%, about 7-10%, or about 8-9% by weight Ludipress. In an embodiment, the coated tablet formulation comprises about 0.5-2%, about 0.5-1.5%, about 0.5-1%, about 1-2%, or about 1.5-2% by weight magnesium stearate. In some embodiments, the coated tablet formulation comprises about 0.5-2%, about 0.5-1.5%, about 0.5-1%, or about 1-2% by weight triethyl citrate (TEC). In some embodiments, the coated tablet formulation comprises about 5-20%, about 7-18%, about 9-15%, or about 10-13% by weight Eudragit L30D 55. In some embodiments, the coated tablet formulation comprises about 2-12%, about 3-11%, about 4-10%, about 5-9%, or about 6-8% by weight HPC subcoat.

In particular embodiments, the coated tablet (coated with 15% Eudragit L30D 55) formulation comprises about 35% by weight of alkaline phosphatase ((e.g. bIAP, or the other alkaline phosphatase agents described herein, and variants thereof); about 35% by weight sucrose; about 8% by weight buffer salts, optionally selected from a Tris base, magnesium chloride, and zinc sulfate; about 9% by weight Ludipress; about 1% by weight magnesium stearate; about 1% by weight triethyl citrate (TEC); and about 13% by weight Eudragit L30D 55.

In certain embodiments, the coated tablet (coated with a 7% HPC subcoat and 10% Eudragit L30D55) formulation comprises about 33.6% by weight of alkaline phosphatase ((e.g. bIAP, or the other alkaline phosphatase agents described herein, and variants thereof); about 33.6% by weight sucrose; about 7.7% by weight buffer salts, optionally selected from a Tris base, magnesium chloride, zinc sulfate; about 8.3% by weight Ludipress; about 0.84% by weight magnesium stearate; about 5.89% by weight HPC; about 0.9% by weight triethyl citrate (TEC); and about 9.01% by weight Eudragit L30D 55.

4. Formulation 4

In various embodiments, the formulation of the present invention is in the form of a tablet (e.g., formed by compressing spray-dried material (SD powder)) comprising an alkaline phosphatase and enterically coated. In certain embodiments, the kinetics of release differ based on formulation and enteric coating. For example, in some embodiments, Formulation 4 tablets exhibit fast-release profiles. Specifically, Formulation 4 tablets may dissolve and release some of the bIAP between a pH of 5.5 and pH 6.5, and in such embodiments, the bIAP is 78% released from the tablet after 15 minutes of dissolution at pH 5.5 and then 87% released bIAP at 60 minutes at pH 6.5.

In some embodiments, the tablet formulation comprises about 35-50%, about 40-50%, about 41-49%, about 42-48%, about 43-47%, about 44-46%, or about 45-50% by weight of alkaline phosphatase (e.g. bIAP, or the other alkaline phophatase agents described herein, and variants thereof). In some embodiments, the tablet formulation comprises about 35-50%, about 40-50%, about 41-49%, about 42-48%, about 43-47%, about 44-46%, or about 45-50% by weight sugar excipient (e.g., lactose, sucrose, or trehalose). In some embodiments, the tablet formulation does not comprise hydroxypropyl methylcellulose acetate succinate. In some embodiments, the tablet formulation further comprises about 5-15%, about 6-14%, about 7-13%, about 8-12%, about 9-11% or about 10-15% by weight buffer salts, optionally selected from a Tris base, magnesium chloride, zinc sulfate. In some embodiments, the tablet formulation comprises about 0.5-2%, about 0.5-1.5%, or about 1-2% by weight of magnesium-stearate. The weight as described herein refers to the total weight of all components.

In various embodiments, the tablet formulation further comprises an enteric coating. In various embodiments, the enteric coating is Eudragit L 30 D 55. In some embodiments, the tablet formulation further comprises two coatings, wherein the first coating comprises a HPC (hydroxypropyl cellulose) subcoat and the second coating comprises Eudragit L 30 D 55. In various embodiments, the HPC subcoat serves to isolate the IAP from the acidic Eudragit L 30 D 55 polymer. In some embodiments, the tablet coating comprises about 5-15%, about 6-14%, about 7-13%, about 8-12%, about 9-10% weight gain of an enteric polymer (e.g., EUDRAGIT L 30 D 55). In various embodiments, the tablet is coated with about a 7%, 8%, 9%, 10%, 11% or 12% weight gain of Eudragit L 30 D 55. In some embodiments, the tablet coating comprises between 1-15%, between 2-14%, between 3-13%, between 4-12%, between 5-11%, between 6-10%, between 7-9% weight gain of a HPC subcoat that serves to isolate the IAP from the acidic EUDRAGIT L 30 D 55 polymer. In various embodiments, the tablet is coated with about a 5%, 6%, 7%, 8% or 9% weight gain HPC subcoat.

In some embodiments, the tablet formulation comprises about 45% by weight of the alkaline phosphatase (e.g. bIAP, or the other alkaline phosphatase agents described herein, and variants thereof); about 45% by weight lactose; 0% by weight a binder excipient (e.g., hydroxypropylcellulose (HPC) or hydroxypropyl methylcellulose acetate succinate (HPMCAS, optionally L, M, or H grade)); about 1% by weight of magnesium-stearate; and about 10% by weight buffer salts, optionally selected from a Tris base, magnesium chloride, zinc sulfate. The weight as described herein refers to the total weight of all components.

In particular embodiments, the uncoated tablet formulation comprises about 44.8% by weight of the alkaline phosphatase (e.g. bIAP, or the other alkaline phosphatase agents described herein, and variants thereof); about 44.8% by weight lactose; 0% by weight a binder excipient (e.g., hydroxypropylcellulose (HPC) or hydroxypropyl methylcellulose acetate succinate (HPMCAS, optionally L, M, or H grade)); about 1% by weight of magnesium-stearate; and about 10.21% by weight buffer salts, optionally selected from a Tris base, magnesium chloride, zinc sulfate. The weight as described herein refers to the total weight of all components.

In some embodiments, the coated tablet (coated with 15% Eudragit L30D 55) formulation comprises about 30-50%, about 35-45%, about 36-44%, about 37-43%, or about 39-41% by weight of alkaline phosphatase ((e.g. bIAP, or the other alkaline phosphatase agents described herein, and variants thereof). In some embodiments, the coated tablet formulation comprises about 30-50%, about 35-45%, about 36-44%, about 37-43%, or about 39-41% by weight sugar excipient (e.g., lactose, sucrose, or trehalose). In some embodiments, the coated tablet formulation comprises about 5-15%, about 6-14%, about 7-13%, about 8-12%, or about 9-11% by weight buffer salts, optionally chosen from a Tris base, magnesium chloride, and zinc sulfate. In an embodiment, the coated tablet formulation comprises about 0.5-2%, about 0.5-1.5%, about 0.5-1%, about 1-2%, or about 1.5-2% by weight magnesium stearate. In some embodiments, the coated tablet formulation comprises about 0.1-2%, about 0.5-2%, about 0.5-1.5%, about 0.5-1%, or about 1-2% by weight triethyl citrate (TEC). In some embodiments, the coated tablet formulation comprises about 5-20%, about 7-18%, about 9-15%, or about 10-13% by weight Eudragit L30D 55. In some embodiments, the coated tablet formulation comprises about 2-12%, about 3-11%, about 4-10%, about 5-9%, or about 6-8% by weight HPC subcoat.

In certain embodiments, the coated tablet (coated with 10% Eudragit L30D 55) formulation comprises about 40.0% by weight of alkaline phosphatase ((e.g. bIAP, or the other alkaline phosphatase agents described herein, and variants thereof); about 40.0% by weight lactose; about 10% by weight buffer salts, optionally selected from a Tris base, magnesium chloride, zinc sulfate; about 1% by weight magnesium stearate; about 1% by weight triethyl citrate (TEC); and about 9.0% by weight Eudragit L30D 55.

In particular embodiments, the coated tablet (coated with a 7% HPC subcoat and 10% Eudragit L30D55) formulation comprises about 37.38% by weight of alkaline phosphatase ((e.g. bIAP, or the other alkaline phosphatase agents described herein, and variants thereof); about 37.38% by weight lactose; about 8.6% by weight buffer salts, optionally selected from a Tris base, magnesium chloride, zinc sulfate; about 0.84% by weight magnesium stearate; about 5.89% by weight HPC; about 0.9% by weight triethyl citrate (TEC); and about 9.01% by weight Eudragit L30D 55.

5. Formulation 5

In various embodiments, the formulation of the present invention is in the form of a tablet (e.g., formed by compressing spray-dried material (SD powder)) comprising an alkaline phosphatase and enterically coated. In certain embodiments, the kinetics of release differ based on formulation and enteric coating. For example, in some embodiments, Formulation 5 tablets exhibit sustained-release profiles. Specifically, Formulation 5 tablets may dissolve and release some of the bIAP at pH 6.5, as assessed by in vitro dissolution assay, and in such embodiments, the bIAP is 67% released from the tablet after 120 minutes of dissolution at pH 6.5.

In some embodiments, the tablet formulation comprises about 20-40%, about 25-35%, about 27-33%, about 28.5-32.5%, about 29.5-31.5%, or about 30-31%, by weight of alkaline phosphatase (e.g. bIAP, or the other alkaline phophatase agents described herein, and variants thereof). In some embodiments, the tablet formulation comprises about 20-40%, about 25-35%, about 27-33%, about 28.5-32.5%, about 29.5-31.5%, or about 30-31% by weight excipient (e.g., lactose, sucrose, or trehalose). In various embodiments, the tablet formulations comprise about 20-40%, about 25-35%, about 27-33%, about 28.5-32.5%, about 29.5-31.5%, or about 30-31% by weight a binder excipient (e.g., hydroxypropylcellulose (HPC) or hydroxypropyl methylcellulose acetate succinate (HPMCAS, optionally L, M, or H grade)). In some embodiments, the tablet formulation does not comprise hydroxypropyl methylcellulose acetate succinate. In some embodiments, the tablet formulation further comprises about 3-12%, about 4-11%, about 5-10%, about 6-9%, or about 7-8% by weight buffer salts, optionally selected from a Tris base, magnesium chloride, zinc sulfate. In some embodiments, the tablet formulation comprises about 0.5-2%, about 0.5-1.5%, or about 1-2% by weight of magnesium-stearate. The weight as described herein refers to the total weight of all components.

In various embodiments, the tablet formulation further comprises an enteric coating. In various embodiments, the enteric coating is Eudragit L 30 D 55. In some embodiments, the tablet formulation further comprises two coatings, wherein the first coating comprises a HPC (hydroxypropyl cellulose) subcoat and the second coating comprises Eudragit L 30 D 55. In various embodiments, the HPC subcoats serves to isolate the IAP from the acidic Eudragit L 30 D 55 polymer. In some embodiments, the tablet coating comprises about 5-15%, about 6-14%, about 7-13%, about 8-12%, about 9-10% weight gain of an enteric polymer (e.g., EUDRAGIT L 30 D 55). In various embodiments, the tablet is coated with about a 7%, 8%, 9%, 10%, 11% or 12% weight gain of Eudragit L 30 D 55. In some embodiments, the tablet coating comprises between 1-15%, between 2-14%, between 3-13%, between 4-12%, between 5-11%, between 6-10%, between 7-9% weight gain of a HPC subcoat that serves to isolate the IAP from the acidic EUDRAGIT L 30 D 55 polymer. In various embodiments, the tablet is coated with about a 5%, 6%, 7%, 8% or 9% weight gain HPC subcoat.

In some embodiments, the tablet formulation comprises about 31% by weight of the alkaline phosphatase (e.g. bIAP, or the other alkaline phosphatase agents described herein, and variants thereof); about 36% by weight sucrose; about 31% by weight a binder excipient (e.g., hydroxypropylcellulose (HPC) or hydroxypropyl methylcellulose acetate succinate (HPMCAS, optionally L, M, or H grade)); about 1% by weight of magnesium-stearate; and about 7% by weight buffer salts, optionally selected from a Tris base, magnesium chloride, zinc sulfate. The weight as described herein refers to the total weight of all components.

In particular embodiments, the tablet formulation comprises about 30.52% by weight of the alkaline phosphatase (e.g. bIAP, or the other alkaline phosphatase agents described herein, and variants thereof); about 30.52% by weight sucrose; about 30.52% by weight a binder excipient (e.g., hydroxypropylcellulose (HPC) or hydroxypropyl methylcellulose acetate succinate (HPMCAS, optionally L, M, or H grade)); about 1.00% by weight of magnesium-stearate; and about 7.02% by weight buffer salts, optionally selected from a Tris base, magnesium chloride, zinc sulfate. The weight as described herein refers to the total weight of all components.

6. Formulation 6

In various embodiments, the formulation of the present invention is in the form of a tablet (e.g., formed by compressing spray-dried material (SD powder)) comprising an alkaline phosphatase and enterically coated. In certain embodiments, the kinetics of release differ based on formulation and enteric coating.

In some embodiments, the tablet formulation comprises about 30-50%, about 35-45%, about 36-44%, about 37-43%, about 38-42%, or about 39-41%, by weight of alkaline phosphatase (e.g. bIAP, or the other alkaline phophatase agents described herein, and variants thereof). In some embodiments, the tablet formulation comprises about 30-50%, about 35-45%, about 36-44%, about 37-43%, about 38-42%, or about 39-41% by weight excipient (e.g., lactose, sucrose, or trehalose). In various embodiments, the tablet formulations comprise about 4-15%, about 5-14%, about 6-13%, about 7-12%, about 8-11%, or about 9-10% by weight a binder excipient (e.g., hydroxypropylcellulose (HPC) or hydroxypropyl methylcellulose acetate succinate (HPMCAS, optionally L, M, or H grade)). In some embodiments, the tablet formulation further comprises about 3-14%, about 4-13%, about 5-12%, about 6-11%, about 7-10%, or about 8.5-9.5% by weight buffer salts, optionally selected from a Tris base, magnesium chloride, zinc sulfate. In some embodiments, the tablet formulation comprises about 0.5-2%, about 0.5-1.5%, or about 1-2% by weight of magnesium-stearate. The weight as described herein refers to the total weight of all components.

In various embodiments, the tablet formulation further comprises an enteric coating. In various embodiments, the enteric coating is Eudragit L 30 D 55. In some embodiments, the tablet formulation further comprises two coatings, wherein the first coating comprises a HPC (hydroxypropyl cellulose) subcoat and the second coating comprises Eudragit L 30 D 55. In various embodiments, the HPC subcoats serves to isolate the IAP from the acidic Eudragit L 30 D 55 polymer. In some embodiments, the tablet coating comprises about 5-15%, about 6-14%, about 7-13%, about 8-12%, about 9-10% weight gain of an enteric polymer (e.g., EUDRAGIT L 30 D 55). In various embodiments, the tablet is coated with about a 7%, 8%, 9%, 10%, 11% or 12% weight gain of Eudragit L 30 D 55. In some embodiments, the tablet coating comprises between 1-15%, between 2-14%, between 3-13%, between 4-12%, between 5-11%, between 6-10%, between 7-9% weight gain of a HPC subcoat that serves to isolate the IAP from the acidic EUDRAGIT L 30 D 55 polymer. In various embodiments, the tablet is coated with about a 5%, 6%, 7%, 8% or 9% weight gain HPC subcoat.

In some embodiments, the tablet formulation comprises about 40% by weight of the alkaline phosphatase (e.g. bIAP, or the other alkaline phosphatase agents described herein, and variants thereof); about 40% by weight sucrose; about 10% by weight a binder excipient (e.g., hydroxypropylcellulose (HPC) or hydroxypropyl methylcellulose acetate succinate (HPMCAS, optionally L, M, or H grade)); about 1% by weight of magnesium-stearate; and about 9% by weight buffer salts, optionally selected from a Tris base, magnesium chloride, zinc sulfate. The weight as described herein refers to the total weight of all components.

In particular embodiments, the tablet formulation comprises about 40.00% by weight of the alkaline phosphatase (e.g. bIAP, or the other alkaline phosphatase agents described herein, and variants thereof); about 40.00% by weight sucrose; about 9.90% by weight a binder excipient (e.g., hydroxypropylcellulose (HPC) or hydroxypropyl methylcellulose acetate succinate (HPMCAS, optionally L, M, or H grade)); about 1.00% by weight of magnesium-stearate; and about 9.20% by weight buffer salts, optionally selected from a Tris base, magnesium chloride, zinc sulfate. The weight as described herein refers to the total weight of all components.

F. Assays

1. Dissolution/pH Test

It is important to design the tablet formulation to release in its targeted area of the body. For example, solubility is a critical parameter for informing formulation strategies and extrapolating performance in humans. A disintegration assay in various pH levels may be performed using a disintegration apparatus combined with biologically relevant buffers (e.g., Fasted State Simulated Intestinal Fluid (FaSSIF) and Fasted State Simulated Gastric Fluid (FaSSGF)) for uncoated tablets in order to assess the dissolution rate of the various tablet formulations as described herein. FaSSIF is a buffer that simulates fasting conditions in the small intestine, resulting in a pH representative to values measured from the mid-duodenum to the proximal ileum, usually in the range of pH 4-7. FaSSGF is a buffer that simulates fasting conditions in the stomach, usually pH 1.6.

Dissolution rate is the percent of active ingredient released over time from the tablet. Tablets may exhibit fast-release, or "burst," release profiles, for example 78% release in 15 minutes and 87% release at 60 minutes, as shown in Example 3. Tablets may exhibit a sustained release profile, or an intermediate release profile that falls between sustained release and burst release profiles, also depicted in Example 3. Dissolution tests may also be performed on enterically coated tablets. Disintegration assays in various pH levels may be performed using a disintegration apparatus combined with biologically relevant buffers, such as FaSSGF for 2 hours, followed by addition of FaSSIF, with a pH adjustment to pH 5.5 for 45 minutes, and finally, with an additional pH adjustment to pH 6.5 for 2-3 hours.

2. Friability

Friability refers to the tendency of a solid substance to break into smaller pieces under duress or contact, and is important because determining the friability of a formulated tablet will yield information as to the durability of the tablet to remain intact prior to administration. A friability assay may be performed on the tablets of the formulations described herein in order to test the resilience of the tablets in terms of destruction and subsequent weight loss of the tablets in response to simulated pan coating conditions and how compression forces affect the structural stability of the tablets.

3. Dispersibility

The dispersibility of a powder in water is its ability to break down into particles passing through a sieve. A powder sample of known water content may be spread evenly on the surface of 25° C. water. The mixture is then stirred manually for a short time and part of the mixture is filtered through a sieve. The total solids content of the collected liquid is determined. Dispersibility is calculated from the mass of the test portion and the values for water content and total solids.

4. Alkaline Phosphatase Activity

In order to test alkaline phosphatase enzyme activity, assays known to those in the art can be performed. For example, an endpoint AP activity assay and/or a kinetic AP activity assay can be used.

a. Endpoint IAP Activity Assay

An endpoint AP activity assay utilizes purified alkaline phosphatase as a standard by which the activity of samples assayed are quantified. AP solution can also be used as an indicative control. Samples are tested using 2 replicate wells from which S.D. values are generated. Briefly, various samples are dissolved in Sodium dihydrogen phosphate buffer ($NaH_2PO_4$ 50 mM+$ZnSO_4$ 0.5 mM, pH 7.0). A standard curve of AP concentrations of the Sigma standard ranging from 0-20 nM is prepared alongside the AP samples. 80 µl of samples or standards are added to the wells of a flat bottomed 96-well plate, followed by 50 µl of 5 mM pNPP solution. The plate is then incubated for one hour at 25° C. in a light protected environment. After one hour, 20 µl of stop solution is added to each well, then the OD at $A_{405}$ is read in a plate reader, and concentrations are derived through comparison to the standard curve generated through a linear fit trend line, the Y=X equation of which is used to calculate concentration values.

b. Kinetic IAP Activity Assay

A kinetic AP activity assay utilizes purified alkaline phosphatase as a control to test the activity of samples assayed. AP solution can also be used as an indicative control. Briefly, various samples are dissolved in diethanolamine based buffer (pH 9.8 at 37° C.), and after five minutes of pre-incubation at 37° C., are combined with a 5 mM solution of p-nitrophenyl phosphate (pNPP). After an additional 10 minutes, the colorimetric output at 405 nm as a function of pNPP→NPP dephosporylation via enzyme phosphatase activity is measured every 20 seconds over 5 minutes using a plate reader. This provides a readout of enzyme kinetics over this time period, the slope of which can be converted to enzyme activity using the substrate extinction coefficient (18.5 $OD_{405}$ units/mM*cm pathlength) or which can be compared to the slope generated from the AP standard.

5. Stability in Chyme

In order to assess AP-based agent stability in chyme, samples of AP-based agents are incubated in human chyme at 37 C. Stability is then evaluated by assessing aliquots withdrawn from the incubated samples at 0, 0.5, 1, 2, 3, 4, 5, and 6 hours for AP activity using a pNPP AP substrate (absorbance is read at 405 nm using a plate reader). Different chyme specimens can be used for evaluation of stability, including mixed chyme samples. Chyme samples are characterized for pH, liquid content, and protease activity.

G. Methods of Treatment

Without wishing to be bound by theory, it is believed that AP-based agent including alkaline phosphatases (e.g., IAPs) play a key role in many GI and systemic processes including, for example, participating in intestinal defense, mediating anti-inflammatory functions, maintaining normal gut microflora profiles, maintaining mucosal barrier integrity, and regulating digestion and nutrient (fat) absorption. Accordingly, the present invention provides the use of AP-based agents in a broad-range of therapeutic applications for modulating immune functions, metabolic functions, and neurological functions. In various embodiments, the present invention provides for the treatment of microbiome-related disorders, GI dysbiosis, GI inflammation, colitis (e.g., ulcerative colitis, Crohn's disease, acute and chronic radiation enteropathy, colitis and proctitis), metabolic diseases (e.g., metabolic syndrome, obesity, cachexia, NASH and diabetes), neurological diseases (e.g., multiple sclerosis, neuropsychiatric disorders), cystic fibrosis, sepsis, radiation-related disorders (e.g., radiation enteropathy) and renal failure with an AP, including, without limitation a pharmaceutical composition comprising an AP-based agent, such as the modified release formulations described herein.

In various aspects, the present invention provides methods for modulating and protecting a subject's GI microbiome, comprising administering an effective amount of a pharmaceutical composition comprising an AP-based agent (and/or additional therapeutic agents) to the subject. In some embodiments, methods of the invention may be used to treat subjects with reduced levels and/or function of GI tract microbiome by administering an AP-based agent of the invention so as to increase or preserve the number of commensal bacteria and composition of the GI microbiome. In other embodiments, methods of the invention relate to treating infections by pathogenic bacteria and/or inhibiting the growth or decrease the number of pathogenic bacteria in the GI tract.

In various embodiments, the methods of the invention comprise treating or preventing a microbiome-mediated disorder. Illustrative microbiome-mediated disorder includes, but are not limited to, for example, those found in Table 3 of WO 2014/121298, the entire contents of which are incorporated herein by reference. For example, the methods described can be used to treat symptoms associated with reduced levels of commensal bacteria and/or function of GI tract microbiome, e.g., antibiotic-associated diarrhea (AAD), *Clostridium difficile*-associated disease (CDAD), inflammatory disorders, acquired immunodeficiency syndrome (AIDS) including HIV-mediated gut dysbiosis and GI barrier dysfunctions, hypothyroidism, and obesity.

1. Treatment of CDI and/or CDAC

In various aspects, the present invention provides pharmaceutical compositions comprising an AP-based agent of the invention (and/or additional therapeutic agents) for use in treating an antibiotic-induced adverse effect in the GI tract and/or prevention or treatment of CDI and/or a CDAD in a subject in need thereof. Without wishing to be bound by theory, it is believed that AP-based agent of the invention mediates NTP dephosphorylation which promotes the growth of commensal bacteria in preference to pathologic bacteria and hasten the recovery from antibiotic-induced dysbiosis. Accordingly, treatment with the AP-based agents of the invention has the potential to protect from CDI and enteric gram negative pathogens. In various embodiments, the antibiotic-induced adverse effect and/or CDI or CDAD is one or more of: antibiotic-associated diarrhea, *C. difficile* diarrhea (CDD), *C. difficile* intestinal inflammatory disease, colitis, pseudomembranous colitis, fever, abdominal pain, dehydration and disturbances in electrolytes, megacolon, peritonitis, and perforation and/or rupture of the colon.

In various embodiments, the subjects include, but are not limited to, subjects that are at a particular risk for a microbiome-mediated disorder, such as, by way of non-limiting example, those undergoing treatment or having recently undergone treatment with an antibiotic. For example, the subject may have taken an antibiotic during the past about 30 or so days and/or have an immune system that is weak (e.g. from a chronic illness) and/or is a woman and/or is elderly (e.g. over about 65 years old) and/or is undergoing (or has undergone) treatment with for heartburn or stomach acid disorders (e.g. with agents such as PREVACID, TAGAMET, PRILOSEC, or NEXIUM and related drugs) and/or has recently been in the hospital, including in an intensive care unit, or lives in a nursing home. Accordingly, in some embodiments, the methods and uses of the present invention treat or prevent a nosocomial infection and/or a secondary emergent infection and/or a hospital acquired infection (HAI).

In various embodiments, the present invention provides methods for treating antibiotic-induced adverse effects in the GI tract, comprising administration of an effective amount of an alkaline phosphatase of the invention (and/or additional therapeutic agents) to a subject in need thereof. In another embodiment, the present invention provides methods for preventing an antibiotic-induced adverse effect in the GI tract, comprising an effective amount of an alkaline phosphatase of the invention (and/or additional therapeutic agents) to a subject in need thereof.

In various embodiments, the alkaline phosphatase of the invention protects the intestinal microbiome from antibiotics-induced damage. In an embodiment, the AP-based agent protects the intestinal microbiome from cephalosporin-induced damage. In some embodiments, the AP-based agent of the invention protects the intestinal microbiome from ceftriaxone (CRO)-induced damage. In some embodiments, the methods of the invention treat or prevent an antibiotics-associated adverse effect including but not limited to diarrhea, nausea, vomiting, dysgeusia, colitis, and pseudomembranous colitis disease and/or symptoms. In an embodiment, methods of the invention can be used to treat or prevent antibiotic-associated diarrhea (AAD).

In various embodiments, the present invention provides for compositions and methods for treating infections by pathogenic bacteria and/or inhibiting the growth or decrease the number of pathogenic bacteria in the GI tract. In various embodiments, the present invention provides for compositions and methods that mitigate or prevent the overgrowth of various coliforms in a patient's gut (including coliforms that are virulent and/or antibiotic resistant). Illustrative coliforms include *Citrobacter, Enterobacer, Hafnia, Kelbsiella*, and *Escherichia*. In various aspects, the methods and compositions described herein prevent or diminish secondary infections with resistant organisms. In an embodiment, the pathogenic bacteria is an enterobacteria such as *Salmonella*.

In various embodiments, the present invention provides methods for treating or preventing CDI and/or a CDAD, comprising administering an effective amount of an alkaline phosphatase of the invention a subject in need thereof. In an embodiment, the present invention provides methods for preventing CDI and/or a CDAD, comprising administering an effective amount of administering an effective amount of an alkaline phosphatase of the invention to a subject in need thereof (by way of non-limiting example, a patient that is being administered or will be administered an antibiotic).

In some embodiments, the invention relates to a method of preventing CDI and/or a CDAD, comprising administering an effective amount of an alkaline phosphatase of the invention to a subject in need thereof, wherein the subject is undergoing therapy with a primary antibiotic. A "primary antibiotic" refers to an antibiotic that is administered to a patient and which may result in CDI and/or CDAD. These include the antibiotics that most often lead to CDI and/or CDAD: e.g., fluoroquinolones, cephalosporins, clindamycin and penicillins. In some embodiments the antibiotic is a selected from beta-lactams, carbapenems, monobactams, β-lactamase inhibitors, aminoglycosides, tetracyclines, rifamycins, macrolides, ketolides, lincosamides, streptogramins, sulphonamides, oxazolidinones, and quinolones. In some embodiments the antibiotic includes, but is not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, and methicillin); monobactam antibiotics (aztreonam); and carbapenem antibiotics (ertapenem, doripenem, imipenem/cilastatin, and meropenem), and vancomycin.

In various embodiments, the CDI and/or CDAD is treated or prevented in the context of initial onset or relapse/recurrence (e.g. due to continued or restarted antibiotic therapy). For example, in a patient that has previously suffered from CDI, the present alkaline phosphatase may be administered upon the first symptoms of recurrence. By way of non-limiting example, symptoms of recurrence include, in a mild case, about 5 to about 10 watery bowel movements per day, no significant fever, and only mild abdominal cramps while blood tests may show a mild rise in the white blood cell count up to about 15,000 (normal levels are up to about 10,000), and, in a severe case, more than about 10 watery stools per day, nausea, vomiting, high fever (e.g. about 102-104° F.), rectal bleeding, severe abdominal pain (e.g. with tenderness), abdominal distention, and a high white blood count (e.g. of about 15,000 to about 40,000).

Regardless of initial onset or relapse/recurrence, CDI and/or CDAD may be diagnosed via any of the symptoms described herein (e.g. watery diarrhea about 3 or more times a day for about 2 days or more, mild to bad cramping and pain in the belly, fever, blood or pus in the stool, nausea, dehydration, loss of appetite, loss of weight, etc.). Regardless of initial onset or relapse/recurrence, CDI and/or CDAD may also be diagnosed via enzyme immunoassays, e.g., to detect the *C. difficile* toxin A or B antigen and/or glutamine dehydrogenase (GDH), which is produced by *C. difficile* organisms), polymerase chain reactions (e.g., to detect the *C. difficile* toxin A or B gene or a portion thereof (e.g. tcdA or tcdB), including the ILLUMIGENE LAMP assay), a cell cytotoxicity assay. For example, any of the following tests may be used: Meridian ImmunoCard Toxins A/B; Wampole Toxin A/B Quik Chek; Wampole *C. diff* Quik Chek Complete; Remel Xpect *Clostridium difficile* Toxin A/B; Meridian Premier Toxins A/B; Wampole *C. difficile* Tox A/B II; Remel Prospect Toxin A/B EIA; Biomerieux Vidas *C. difficile* Toxin A&B; BD Geneohm *C. diff*; Prodesse Progastro CD; and Cepheld Xpert *C. diff* In various embodiments, the clinical sample is a patient stool sample. Also a flexible sigmoidoscopy "scope" test and/or an abdominal X-ray and/or a computerized tomography (CT) scan, which provides images of your colon, may be used in assessing a patient (e.g. looking for characteristic creamy white or yellow plaques adherent to the wall of the colon). Further, biopsies (e.g. of any region of the GI tract) may be used to assess a potential CDI and/or CDAD patient.

In some embodiments, the methods and uses of the present invention include those in which an initial and/or adjunctive therapy is administered to a subject. Initial and/or adjunctive therapy indicates therapy that is used to treat, for example, a microbiome-mediated disorder or disease upon detection of such disorder or disease. In an embodiment, initial and/or adjunctive therapy indicates therapy that is used to treat CDI and/or CDAD upon detection of such disease. In some embodiments, the initial and/or adjunctive therapy is one or more of metronidazole, vancomycin, fidaxomicin, rifaximin, charcoal-based binder/adsorbent, fecal bacteriotherapy, probiotic therapy, and antibody therapy. In various embodiments, the methods and uses of the present invention include use of the alkaline phosphatase as an adjuvant to any of these initial and/or adjunctive therapies (including co-administration or sequential administration). In various embodiments, the methods and uses of the present invention include administration of the AP-based agent described herein to a subject undergoing initial and/or adjunctive therapies.

In various embodiments, the alkaline phosphatase of the invention is administered to a subject who suffers from an increased mucosal permeability of the GI tract. In some embodiments, increased mucosal permeability of the GI tract is the result of a decreased perfusion or ischemia of the intestines. Ischemia, or a lack of oxygen supply by the bloodstream, may be caused by, for example, heart failure, congenital heart disease, congestive heart failure, coronary heart disease, ischemic heart disease, injuries, trauma or surgery. In an embodiment, the AP-based agent is administered to a subject who suffers from leaky gut syndrome.

In some embodiments, the increased mucosal permeability of the GI tract is associated with or caused by autoimmune and inflammatory bowel diseases (IBD), for example, Celiac's disease, Crohn's disease, and colitis (e.g., ulcerative colitis). Accordingly, in some embodiments, the present invention provides methods for treating or preventing autoimmune and IBD, for example, Celiac disease, Crohn's disease, and colitis (e.g., ulcerative colitis), comprising administering an effective amount of an AP-based agent of the invention to a subject in need thereof. IBD is a group of inflammatory conditions of the large intestine and, in some cases, the small intestine. The main forms of IBD are Crohn's disease and ulcerative colitis (UC). IBD also includes collagenous colitis, lymphocytic colitis, ischemic colitis, diversion colitis, Behçet's syndrome, infective colitis, and indeterminate colitis.

2. Celiac Disease

In some embodiments, the present invention provides methods of treating Celiac disease. In some embodiments, the present invention provides methods of treating GI disorders associated with Celiac disease. Celiac disease is an autoimmune disorder that can occur in genetically predisposed people where the ingestion of gluten leads to damage in the small intestine. Individuals with celiac disease have increased intestinal permeability, which allows gluten breakdown products (the triggering antigens of Celiac disease) to reach gut-associated lymphoid tissue, thus initiating an inflammatory response including inflammatory cytokine release and T-cell recruitment. Celiac disease is characterized by chronic inflammation of the small intestinal mucosa that may result in atrophy of the small intestinal villi and diverse symptoms, such as malabsorption, diarrhea, abdominal pain, bloating, fatigue, and nausea. In various embodiments, methods of the invention effectively treat one or more symptoms of Celiac disease including GI symptoms, abdominal symptoms, and non-GI symptoms.

Methods for measuring the improvement in one or more symptoms of Celiac disease can include assessment of the lactulose-to-mannitol (LAMA) ratio, which is an experimental biomarker of intestinal permeability (Kelly et al., (2012) Aliment Pharmacol Ther 2013; 37: 252-262, the entire disclosure is hereby incorporated by reference); measurement of anti-transglutaminase antibody levels; and assessment of clinical symptoms using the Celiac Disease Patient Reported Outcome (CeD PRO), Gastrointestinal Symptom Rating Scale (GSRS), Celiac Disease Gastrointestinal Symptom Rating Scale (CeD GSRS), Bristol Stool Form Scale (BSFS), General Well-Being Questionnaire, Short Form 12 Health Survey Version 2 (SF12V2), Celiac Disease Quality of Life Questionnaire (CeD-QoL), and Clinician Global Assessment of Disease Activity (CGA) as disclosed, for example, in WO/2015/154010, the entire disclosure of which is hereby incorporated by reference. In various embodiments, the present methods of treating Celiac disease provide for a therapeutic effect as assessed by one or more of these measurements.

In some embodiments, the present methods treat Celiac disease and allow a subject to introduce gluten into their diet without substantial symptoms.

3. AIDS Treatment

In some embodiments, the increased mucosal permeability of the GI tract is associated with or caused by Acquired Immunodeficiency Syndrome (AIDS). Accordingly, in some embodiments, the present invention provides methods of treating GI disorders associated with AIDS. GI disorders are among the most frequent complaints in patients with human immunodeficiency virus 1 (HIV-1) or human immunodeficiency virus 2 (HIV-2)-associated AIDS. GI manifestations of HIV disease include diarrhea, dysphagia, odynophagia, nausea, vomiting, weight loss, abdominal pain, anorectal disease, jaundice, hepatomegaly, GI tract bleeding, and GI tumors (e.g., Kaposi's sarcoma and non-Hodgkin's lymphoma).

Progressive HIV infection often results in GI tract damage, microbial translocation, inflammation, and immune activation which drive progression of disease to AIDS. The term "HIV enteropathy" has been used to describe changes in mucosal structure and function associated with gut-mediated immune dysfunction, as well as to denote the clinical syndrome of chronic diarrhea without an identified infectious cause. In addition to chronic diarrhea, HIV enteropathy is often characterized by increased GI inflammation, increased intestinal permeability, and malabsorption of bile acids and vitamin B12—abnormalities that are thought to be due to direct or indirect effects of HIV on the enteric mucosa (Brenchley J M, Douek D C. Mucosal Immunol 2008; 1:23-30). Clinical consequences include decreased fat and carbohydrate absorption, a trend toward decreased small-bowel transit time, and jejunal atrophy. In various embodiments, methods of the invention effectively treat the symptomatic effects of HIV enteropathy. In various embodiments, methods of the invention prevent, slow, or reverse the progression of HIV infection to AIDS. In various embodiments, methods of the invention prevent or slow the progression of AIDS to death.

Further still, the HIV-1 subtype that a subject becomes infected with may be a factor in the rate of progression to AIDS. In various embodiments, the present methods effectively treat a patient infected with HIV-1 subtype C, D, and G. In another embodiment, the present methods effectively treat a patient infected with HIV-1 subtype A.

In some embodiments, the present invention provides methods of treating various GI disorders associated with HIV infection and/or AIDS. For example, the present invention provides methods of treating HIV-mediated gut dysbiosis and GI barrier dysfunctions, which in various embodiments, may be caused by the HIV, the antibiotics administered to the HIV infected subject, and/or the medications being administered to the HIV infected subject. For example, the HIV infected subject may be taking one or more nucleoside analogues such as deoxyadenosine analogues (e.g., didanosine, vidarabine), adenosine analogues (e.g., BCX4430), deoxycytidine analogues (e.g., cytarabine, emtricitabine, lamivudine, zalcitabine), guanosine and deoxyguanosine analogues (e.g., abacavir, aciclovir, entecavir), thymidine and deoxythymidine analogues (e.g., stavudine, telbivudine, zidovudine), and deoxyuridine analogues (e.g., idoxuridine, trifluridine). In some embodiments, the HIV infected subject may be taking one or more drugs of the highly active anti-retroviral therapy (HAART) regimen. Illustrative HAART medications include entry inhibitors or fusion inhibitors (e.g., maraviroc, enfuvirtide), nucleoside reverse transcriptase inhibitors (NRTI) and nucleotide reverse transcriptase inhibitors (NtRTI) such as the nucleoside and nucleotide analogues described herein, non-nucleoside reverse transcriptase inhibitors (e.g., nevirapine, efavirenz, etravirine, rilpivirine), integrase inhibitors (e.g., raltegravir), and protease inhibitors (e.g., lopinavir, indinavir, nelfinavir, amprenavir, ritonavir, darunavir, atazanavir).

In various embodiments, the present methods reduce local inflammation, alter composition of the GI microbiota, enhance clearance of products of microbial translocation from the circulation, and repair enterocyte barrier in an HIV infected subject and/or a subject having AIDS. In an embodiment, the present methods reduce GI tract damage and gut dysbiosis in an HIV infected subject and/or a subject having AIDS. For example, the present methods may reverse the changes in GI microbiota observed in HIV infected subjects or subjects having AIDS. By way of example, these changes in GI microbiota that may be reversed by the present methods include an altered microbiota featuring increased pathobionts such as *Staphylococcus* spp., *Psedomonas* spp., Enterobacteriaceae family members with pro-inflammatory potential, as well as enteropathogenic bacteria that catabolize tryptophan into kynurenine derivatives (including *Psudemonas, Xanthomonas, Bacillus*, and *Burkholderia* spp.) In an embodiment, the present methods reduce GI barrier dysfunctions in an HIV infected subject and/or a subject having AIDS. For example, the present methods may reverse the increased intestinal permeability (e.g., leaky gut syndrome) in an HIV infected subject and/or a subject having AIDS. In an embodiment, the present methods reduce microbial translocations or translocations of microbial products and inflammatory mediators (e.g., LPS) into the systemic circulation in an HIV infected subject and/or a subject having AIDS. In such methods, the levels of LPS, EndoCAb, sCD14, and I-FABP in the subject's plasma may be reduced. In an embodiment, the present methods reduce immune activation and inflammation (e.g., local and systemic immune activation and inflammation) in an HIV infected subject and/or a subject having AIDS. For example, the present methods may decrease inflammation in the gut-associated lymphoid tissue (GALT) and increase the number of CD4+ cells and Th17 cells. The present methods may further inhibit the release of cytotoxic T cells as well as the production of inflammatory mucosal cytokines and markers such as interferon-α, tumor necrosis factor-α, CRP, IL-1, IL-2, IL-4, IL-6 and IL-13.

4. Cystic Fibrosis

In some embodiments, the present invention provides methods for treating or preventing dysbiosis and GI dysfunction in patients with cystic fibrosis (CF). The genetic disease CF is associated with mutations in the CF transmembrane conductance regulator (CFTR), which regulates epithelial cell ion and water permeability. In some embodiments, the present methods are used to treating a subject who is homozygous for one or more mutations in the CFTR gene. In some embodiments, the subject is heterozygous for one or more mutations in the CFTR gene. In some embodiments, the one or more CFTR mutations are nonsense mutations. In some embodiments, the one or more CFTR mutations are gating mutations. In some embodiments, the one or more CFTR mutations are protein processing mutations. In some embodiments, the one or more CFTR mutations are conductance mutations. In some embodiments, the one or more CFTR mutations are translation mutations. Examples of CFTR mutations include, but are not limited to, F508del, G542X, G85E, R334W, Y122X, G551D, R117H, A455E, S549R, R553X, V520F, R1162X, R347H, N1203K, S549N, R347P, R560T, G1244E, G1349D, G178R, G551S, S1251N, S1255P, S549R, S1255X, Add9T, Y1092X, M1191K, W 1282X, 3659delC, 394delTT, 3905insT, 1078delT, delta 1507, 3876delA, 2184delA, 2307insA, 711+1G>T, 1717-1G>A, 2789+5G>A, 1898+5G>T, 3120+1G>A, 621+1G>T, 3849+10kbC>T, 1898+1G>A, 2183 AA>G, and/or 5/7/9T. In various embodiments, methods of the invention are used to treat a CF patient having one or more of the CFTR mutations disclosure herein. In an embodiment, the patient has one or more of the following CFTR mutations: G551D, G1244E, G1349D, G178R, G551S, S1251N, S1255P, S549N, S549R and/or R117H. In an embodiment, the patient has a F508del mutation. Methods for screening a patient's genotype for CFTR mutations are known and may be carried out by, for example, DNA sequencing such as bidirectional sequencing.

CF patients often exhibit symptoms including chronic respiratory infections and dysfunction at GI mucosal surfaces, resulting insubstantial morbidity and mortality. One of the earliest manifestations of CF is GI dysfunction including severe and recurrent intestinal obstruction as well as nutrient malabsorption, which result in growth failure. CF patients also exhibit GI dysbiosis such as an overabundance of *E. coli* in the fecal microbiota and a decrease in the relative abundance of *Bifidobacterium* species. In various embodiments, methods of the invention effectively treat one or more GI-related symptoms of in CF patients.

Methods for measuring change and/or improvement in GI tract function can include, but are not limited to: endoscopy for direct examination of epithelium and mucosa; histological evaluation and/or tissue procurement for direct evaluation of structural changes and/or immune biomarkers; urine tests for assessment of permeability with non-absorbable sugars and LPS levels; stool tests for assessment of inflammation and/or microbiota changes (for example by PCR); and/or blood tests for assessment of specific markers, including CD4+ cell counts, Th17 cell counts, and/or LPS levels.

In some embodiments, the present invention provides methods of treating GI disorders associated with hypothyroidism. Hypothyroidism is a condition in which the thyroid gland does not produce enough thyroid hormone (thyroxine or T4). Often, hypothyroidism slows the actions of the digestive tract causing constipation, or the digestive tract may stop moving entirely. Methods of the invention may alleviate the one or more GI symptoms associated with hypothyroidism.

5. NEC Treatment

In one aspect, the present invention provides methods for preventing or treating necrotizing enterocolitis (NEC). The present methods comprise administering to a subject in need thereof an AP-based agent as described herein or a pharmaceutical composition or a formulation such as a modified-release formulation as described herein.

In various embodiments, methods of the invention relate to a pediatric subject for the prevention or treatment of NEC. In various embodiments, the pediatric subject may be from about 1 day to about 1 week old, from about 1 week to about 1 month old, from about 1 month to about 12 months old, from about 12 months to about 18 months old, from about 18 to about 36 months old, from about 1 to about 5 years old, from about 5 to about 10 years old, from about 10 to about 15 years old, or from about 15 to about 18 years old. In some embodiments, the pediatric subject is an infant of about 1 day, about 2 days, about 3 days, about 4 days, about 5 days, about 6 days, about 1 week, about 2 weeks, about 3 weeks, about 4 weeks, about 1 month, about 2 months, about 3 months, about 4 months, about 5 months, about 6 months, about 7 months, about 8 months, about 9 months, about 10 months, about 11 months, or about 12 months of age. In various embodiments, the pediatric subject is feeding on formula and/or milk. In various embodiments, the pediatric subject is undergoing treatment or has recently undergone treatment with an antibiotic.

In various embodiments, the pediatric subject is a premature infant. In some embodiments, the premature infant is born at less than 37 weeks of gestational age. In some embodiments, the premature infant is born at about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, or about 37 weeks of gestational age. In other embodiments, the pediatric subject is a full term infant, for example, an infant who is born later than about 37 weeks of gestational age. In some embodiments, the pediatric subject may exhibit one or more of prenatal asphyxia, shock, sepsis, or congenital heart disease. In various embodiments, the pediatric subject is of low birth weight. In various embodiments, the pediatric subject weighs less than about 5 pounds, about 4 pounds, about 3 pounds, or about 2 pounds.

In various embodiments, methods of the invention relate to a pregnant woman for the prevention or treatment of NEC. In some embodiments, the pregnant woman is undergoing treatment or has recently undergone treatment with an antibiotic.

The presence and severity of NEC is graded using the staging system of Bell et al., J. Ped. Surg., 15:569 (1980) as follows: In various embodiments, the present methods treat disease at any of these stages.

In various embodiments, methods of the invention effectively treat one or more symptoms of NEC including any of the symptoms described above as well as those symptoms known in the art, including GI symptoms, abdominal symptoms, and non-GI symptoms. In various embodiments, methods of the invention effectively prevent the development of NEC in a subject such as a pediatric subject. In various embodiments, methods of the invention effectively prevent progression of NEC in a subject such as a pediatric subject, for example, from stage I to stage II or from stage II to stage III. In various embodiments, methods of the invention effectively result in regression of NEC in a subject such as a pediatric subject, for example, from stage III to stage II or stage I to complete cure, or from stage II to stage I or to complete cure.

Intestinal dysbiosis is associated with the development of NEC and can be detected in a subject prior to any clinical evidence of the disease. In various embodiments, methods of the invention effectively restore normal microbiota in the intestinal tract of the treated subject. In some embodiments, methods of the invention maintain a normal microbiota in the intestinal tract. For instance, in some embodiments, the methods of the invention maintain a healthy balance (e.g. a healthy ratio and/or healthy distribution) of intestinal microbiota of a subject. In another embodiment, the methods of the invention treat or prevent the overgrowth of one or more pathogenic microorganisms in the GI tract. In certain embodiments, methods of the invention effectively reduce the levels of *Clostridium butyricum* and/or *Clostridium perfringens* in the intestinal tract.

Methods for measuring the improvement in one or more symptoms of NEC include diagnostic imaging modalities such as X-ray and ultrasonography. Methods for measuring change and/or improvement in Gl tract function can include, but are not limited to: endoscopy or colonoscopy for direct examination of epithelium and mucosa; histological evaluation and/or tissue procurement for direct evaluation of structural changes and/or immune biomarkers; stool tests for assessment of inflammation and/or microbiota changes (for example by PCR); and/or blood tests for assessment of specific markers and cells.

In some embodiments, the present invention provides methods of treating or preventing metabolic syndrome, diabetes, hypertension, cardiovascular disease, nonalcoholic fatty liver and other metabolic diseases. In various embodiments, the metabolic syndrome is associated with elevated triglycerides, elevated low density lipoproteins, reduced high density lipoproteins, reduced lipoprotein index, elevated fasting glucose levels, elevated fasting insulin, reduced glucose clearance following feeding, insulin resistance, impaired glucose tolerance, obesity and combinations thereof. For example, the present methods may be used to treat subjects having metabolic syndrome and having abdominal obesity (e.g., waist circumference of 40 inches or above in men or 35 inches or above in women), a blood triglyceride level of 150 mg/dL or greater, HDL of less than 40 mg/dL in men or less than 50 mg/dL in women, systolic blood pressure of 130 mm Hg or greater or diastolic blood pressure of 85 mm Hg or greater and/or fasting glucose of 100 mg/dL or greater. Additional metabolic diseases that may be treated using methods of the invention include those described in US2013/0251701, US2011/0206654, and US2004/0115185, the entire contents of which are hereby incorporated by reference.

In an embodiment, the metabolic disease is obesity. Early exposure to antibiotics (e.g. within about the first 2 years of life) can disrupt the microbiome and lead to eventual disease. Bailey, et al. JAMA Pediatr. 168(11), November 2014, the entire contents of which are hereby incorporated by reference, describes how early exposure to antibiotics is linked to obesity. Accordingly, in some embodiments, the present methods protect the microbiome of a child and prevent diseases such as obesity. In addition, a shift in the ratio between bacterial divisions Firmicutes and Bacteroidetes is often observed in obese individuals. Accordingly, in some embodiments, the present invention provides methods for treating or preventing obesity by administering an AP agent of the invention. Methods of the invention retain a normal diversity of bacteria in the intestinal tract, such as for example, Bacteroidetes, Proteobacteria, and Firmicutes, thereby treating or preventing obesity. Further still, alkaline phosphatases may influence fat absorption at the GI tract. Accordingly, in various embodiments, the present invention provides methods for treating or preventing obesity by limiting GI fat absorption. In various embodiments, methods of the invention are effective for inducing weight loss or preventing weight gain. In some embodiments, the subjects may have undertaken or will undertake a surgery of the digestive system; be greater than about 80-100 pounds overweight; have a BMI of greater than about 35 kg/m2; or have a health problem related to obesity. In some embodiments, the subjects may have dyslipidemia including hyperlipidemia and hyperlipoproteinemia.

6. Diabetes

In another embodiment, the metabolic disease is diabetes. In various embodiments, the present invention relates to the treatment for diabetes (type 1 or type 2) and/or glucose intolerance. In some embodiments, the present invention relates to a method for treating subjects at risk of diabetes, one or more of insulin resistance, prediabetes, impaired fasting glucose (IFG), and impaired glucose tolerance (IGT).

In various embodiments, the present invention relates to the treatment of type 1 diabetes with AP, including the formulations described herein. Type 1 diabetes, once known as juvenile diabetes or insulin-dependent diabetes, is a chronic condition in which the pancreas produces little or no insulin. Treatment is often via intensive insulin regimens, which attempt to mimic the body's normal pattern of insulin secretion, and often involve basal and bolus insulin coverage. For example, one common regimen is the administration of a long-acting insulin (including, for example, glargine/detemir) once or twice a day with rapid acting insulin (including, for example, aspart, glulisine, lispro) preprandially or postprandially and as needed to correct high blood sugars (as monitored by a glucose meter, for example). Doses administered preprandially or postprandially or as needed to correct high blood sugars may be referred to as bolus administrations. Another common regimen involves dosing, including continuous dosing, via an insulin pump (or continuous subcutaneous insulin infusion device (CSII)) of, for example a rapid acting insulin (as described herein and including, for example, aspart, glulisine, lispro). In various embodiments, AP, including the formulations described herein, may replace any of the insulins used in various regimens, including instances in which the insulins are not providing effective therapy in the patient. AP, including the formulations described herein, may cause an increase in patient compliance as it may allow for easier self-dosing relative to various forms of insulin, which must be administered as various doses throughout the day—even in the context of an insulin pump, which requires programming. Further, AP, including the formulations described herein, can offset common frustration of diabetic patient dosing, such as, for example, the dawn phenomenon. Alternatively, AP, including the formulations described herein, may be used adjuvant to any of the type 1 diabetes treatments described herein to, for example, normalize a patient's regimen and avoid blood sugar "dips" (e.g. hypoglycemia, e.g. blood sugar of below about 70 mg/dL) and "spikes" (e.g. hyperglycemia, e.g. blood sugar of greater than about 200 mg/dL) that afflict many patients. Accordingly, in some embodiments, AP, including the formulations described herein, may treat or prevent symptoms associated with hypoglycemia, including for example, shakiness, anxiety, nervousness, palpitations, tachycardia, pallor, coldness, clamminess, dilated pupils (mydriasis), hunger, borborygmus, nausea, vomiting, abdominal discomfort, headache, abnormal mentation, impaired judgment, nonspecific dysphoria, paresthesia, negativism, irritability, belligerence, combativeness, rage, personality change, emotional lability, fatigue, weakness, apathy, lethargy, daydreaming, sleep, confusion, amnesia, lightheadedness or dizziness, delirium, staring, "glassy" look, blurred vision, double vision, flashes of light in the field of vision, automatism, difficulty speaking, slurred speech, ataxia, incoordination, focal or general motor deficit, paralysis, hemiparesis, paresthesia, headache, stupor, coma, abnormal breathing, generalized or focal seizures, memory loss, CNS damage (e.g. cognitive impairment), amnesia, and death. Accordingly, in some embodiments, AP, including the formulations described herein, may treat or prevent symptoms associated with hyperglycemia, including for example, polyphagia, polydipsia, polyuria, blurred vision, fatigue, weight loss, poor wound healing, dry mouth, dry or itchy skin, tingling in feet or heels, erectile dysfunction, recurrent infections, external ear infections (e.g. swimmer's ear), cardiac arrhythmia, stupor, coma, and seizures. In various regimens, a type 1 diabetes patient may receive additional agents to supplement insulin therapy. In some embodiments, AP, including the formulations described herein, are used in this manner. AP, including the formulations described herein, may provide additional therapeutic benefits in patients that are struggling to manage type 1 diabetes with insulin therapy alone. In some embodiments, patients that are struggling to manage type 1 diabetes with insulin therapy alone have poor glycemic control as described herein.

In some embodiments, AP, including the formulations described herein, finds use in reducing a patient's blood glucose level to below about 10 mM, e.g. within the range of about 4 mM to about 7 mM.

In some aspects, the present invention provides a method for treating type 1 or type 2 diabetes, comprising administering an effective amount of AP, including the formulations described herein.

In a number of embodiments, including those in which AP, including the formulations described herein, prevents diabetes and/or treats a pre-diabetic condition, a patient is at risk of diabetes if the patient is characterized by one or more of: being physically inactive; having a parent or sibling with diabetes; having a family background associated with high incidence of diabetes, selected from that is African American, Alaska Native, American Indian, Asian American, Hispanic/Latino, or Pacific Islander American; giving birth to a baby weighing more than 9 pounds; being diagnosed with gestational diabetes; having high blood pressure of about 140/90 mmHg or above; being treated for high blood pressure; having HDL cholesterol level below about 35 mg/dL and/or a triglyceride level above about 250 mg/dL; having polycystic ovary syndrome (PCOS); and having cardiovascular disease.

In various embodiments, AP, including the formulations described herein, may be used to treat diabetes in the context of hospitalization. For example, in some embodiments, AP, including the formulations described herein, may be administered to a patient that is in a diabetic coma. In some embodiments, the patient may be administered to a patient that has one or more of a severe diabetic hypoglycemia, advanced diabetic ketoacidosis (e.g. advanced enough to result in unconsciousness, contributing factors may include one or more of hyperglycemia, dehydration, shock, and exhaustion), hyperosmolar nonketotic coma (e.g. with one or more of hyperglycemia and dehydration are contributing factors). In these embodiments, AP, including the formulations described herein, may be used in conjunction with standard treatment regimens of diabetic comas, including administering one or more of glucose, glucagon, insulin, fluids (e.g. saline with potassium and/or other electrolytes), any of which, optionally, are administered intravenously. In some embodiments, AP, including the formulations described herein, may replace insulin in these treatment regimens and, optionally, is administered orally.

Further, in various embodiments pertaining to diabetes, the patient may be recieving or there may be co-administration with one or more additional agents. Illustrative additional agents include insulin or any anti-diabetic agents (e.g. biguanides, insulin secretogogues such as sulphonylureas or meglitinides, inhibitors of α-glucosidase, thiazolidinediones, and others). The methods of treatment described herein, in various embodiments may comprise administering AP, including the formulations described herein, to a patient that is receiving one or more additional agents and/or non-insulin diabetes agents. Additional agents include one or more of a sulfonylurea (e.g. DYMELOR (acetohexamide), DIABINESE (chlorpropamide), ORINASE (tolbutamide), and TOLINASE (tolazamide), GLUCOTROL (glipizide), GLUCOTROL XL (extended release), DIABETA (glyburide), MICRONASE (glyburide), GLYNASE PRESTAB (glyburide), and AMARYL (glimepiride)); a Biguanide (e.g. metformin (GLUCOPHAGE, GLUCOPHAGE XR, RIOMET, FORTAMET, and GLUMETZA)); a thiazolidinedione (e.g. ACTOS (pioglitazone) and AVANDIA (rosiglitazone); an alpha-glucosidase inhibitor (e.g., PRECOSE (acarbose) and GLYSET (miglitol); a Meglitinide (e.g., PRANDIN (repaglinide) and STARLIX (nateglinide)); a Dipeptidyl peptidase IV (DPP-IV) inhibitor (e.g., JANUVIA (sitagliptin), NESINA (alogliptin), ONGLYZA (saxagliptin), and TRADJENTA (linagliptin)); Sodium-glucose co-transporter 2 (SGLT2) inhibitor (e.g. INVOKANA (canaglifozin)); and a combination pill (e.g. GLUCOVANCE, which combines glyburide (a sulfonylurea) and metformin, METAGLIP, which combines glipizide (a sulfonylurea) and metformin, and AVANDAMET, which uses both metformin and rosiglitazone (AVANDIA) in one pill, KAZANO (alogliptin and metformin), and OSENI (alogliptin plus pioglitazone).

Other additional agents include METFORMIN oral, ACTOS oral, BYETTA subcutaneous, JANUVIA oral, WELCHOL oral, JANUMET oral, glipizide oral, glimepiride oral, GLUCOPHAGE oral, LANTUS subcutaneous, glyburide oral, ONGLYZA oral, AMARY1 oral, LANTUS SOLOSTAR subcutaneous, BYDUREON subcutaneous, LEVEMIR FLEXPEN subcutaneous, ACTOPLUS MET oral, GLUMETZA oral, TRADJENTA oral, bromocriptine oral, KOMBIGLYZE XR oral, INVOKANA oral, PRANDIN oral, LEVEMIR subcutaneous, PARLODEL oral, pioglitazone oral, NOVOLOG subcutaneous, NOVOLOG FLEXPEN subcutaneous, VICTOZA 2-PAK subcutaneous, HUMALOG subcutaneous, STARLIX oral, FORTAMET oral, GLUCOVANCE oral, GLUCOPHAGE XR oral, NOVOLOG Mix 70-30 FLEXPEN subcutaneous, GLYBURIDE-METFORMIN oral, acarbose oral, SYMLINPEN 60 subcutaneous, GLUCOTROl XL oral, NOVOLIN R inj, GLUCOTROL oral, DUETACT oral, sitagliptin oral, SYMLINPEN 120 subcutaneous, HUMALOG KWIKPEN subcutaneous, JANUMET XR oral, GLIPIZIDE-METFORMIN oral, CYCLOSET oral, HUMALOG MIX 75-25 subcutaneous, nateglinide oral, HUMALOG Mix 75-25 KWIKPEN subcutaneous, HUMULIN 70/30 subcutaneous, PRECOSE oral, APIDRA subcutaneous, Humulin R inj, Jentadueto oral, Victoza 3-Pak subcutaneous, Novolin 70/30 subcutaneous, NOVOLIN N subcutaneous, insulin detemir subcutaneous, glyburide micronized oral, GLYNASE oral, HUMULIN N subcutaneous, insulin glargine subcutaneous, RIOMET oral, pioglitazone-metformin oral, APIDRA SOLOSTAR subcutaneous, insulin lispro subcutaneous, GLYSET oral, HUMULIN 70/30 Pen subcutaneous, colesevelam oral, sitagliptin-metformin oral, DIABETA oral, insulin regular human inj, HUMULIN N Pen subcutaneous, exenatide subcutaneous, HUMALOG Mix 50-50 KWIKPEN subcutaneous, liraglutide subcutaneous, KAZANO oral, repaglinide oral, chlorpropamide oral, insulin aspart subcutaneous, NOVOLOG Mix 70-30 subcutaneous, HUMALOG Mix 50-50 subcutaneous, saxagliptin oral, ACTOPLUS Met XR oral, miglitol oral, NPH insulin human recomb subcutaneous, insulin NPH and regular human subcutaneous, tolazamide oral, mifepristone oral, insulin aspart protam-insulin aspart subcutaneous, repaglinide-metformin oral, saxagliptin-metformin oral, linagliptin-metformin oral, NESINA oral, OSENI oral, tolbutamide oral, insulin lispro protamine and lispro subcutaneous, pramlintide subcutaneous, insulin glulisine subcutaneous, pioglitazone-glimepiride oral, PRANDIMET oral, NOVOLOG PenFill subcutaneous, linagliptin oral, exenatide microspheres subcutaneous, KORLYM oral, alogliptin oral, alogliptin-pioglitazone oral, alogliptin-metformin oral, and canagliflozin oral.

Other additional agents include Lispro (HUMALOG); Aspart (NOVOLOG); Glulisine (APIDRA); Regular (NOVOLIN R or HUMULIN R); NPH (NOVOLIN N or HUMULIN N); Glargine (LANTUS); Detemir (LEVEMIR); HUMULIN or NOVOLIN 70/30; and NOVOLOG Mix 70/30 HUMALOG Mix 75/25 or 50/50.

7. Neurological Disease

In various embodiments, the present invention is used to treat or prevent various neurodegenerative diseases. In some embodiments, the neurodegenerative disease is selected from multiple sclerosis (MS; including, without limitation benign multiple sclerosis, relapsing-remitting multiple sclerosis (RRMS), secondary progressive multiple sclerosis (SPMS), progressive relapsing multiple sclerosis (PRMS), and primary progressive multiple sclerosis (PPMS)), Alzheimer's. disease (including, without limitation, Early-onset Alzheimer's, Late-onset Alzheimer's, and Familial Alzheimer's disease (FAD), Parkinson's disease and parkinsonism (including, without limitation, Idiopathic Parkinson's disease, Vascular parkinsonism, Drug-induced parkinsonism, Dementia with Lewy bodies, Inherited Parkinson's, Juvenile Parkinson's), Huntington's disease, Amyotrophic lateral sclerosis (ALS, including, without limitation, Sporadic ALS, Familial ALS, Wesrtern Pacific ALS, Juvenile ALS, Hiramaya Disease).

8. Sepsis

In various embodiments, the present invention provides methods of treating or preventing sepsis. Sepsis is characterized by a whole-body inflammatory state caused by infection. Sepsis includes the presence of various pus-forming and other pathogenic organisms, or their toxins, in the blood or tissues. In some embodiments, the present invention provides methods of treating or preventing septicemia (blood poisoning), bacteremia, viremia, and/or fungemia. In various embodiments, the present invention treats the various end-organ pathologies associated with sepsis such as hypotension, acute tubular necrosis (ATN) and acute respiratory distress syndrome (ARDS).

In various embodiments, the present invention provides methods of treating or preventing renal failure such as acute renal failure (ARF). Acute renal failure involves an acute loss of kidney function that results in an increase of the serum creatinine level. In acute renal failure, the glomerular filtration rate decreases over days to weeks. As a result, excretion of nitrogenous waste is reduced, and fluid and electrolyte balances cannot be maintained. Patients with acute renal failure are often asymptomatic, and the condition is diagnosed by observed elevations of blood urea nitrogen (BUN) and serum creatinine levels. Complete renal shutdown is present when the serum creatinine level rises by at least 0.5 mg per dL per day and the urine output is less than 400 mL per day (oliguria). The AP-based agents described herein can be used not only in the treatment of renal failure but also to improve renal cases where the renal function is at least partly impaired or reduced.

9. Radiation-Induced Enteropathy, Colitis, and/or Proctitis

In various embodiments, the present invention provides methods of treating or preventing radiation-induced enteropathy, colitis, and/or proctitis. Radiation-induced enteropathy is characterized by mucosal atrophy, vascular sclerosis, and progressive intestinal wall fibrosis. Symptoms of the disorder can include malabsorption of nutrients, altered intestinal transit, dysmotility, and abnormal propulsion of intestinal contents. In some embodiments, acute radiation-induced enteropathy occurs within the first month, first 2 months, or first 3 months after radiation exposure. In some embodiments, delayed radiation enteropathy symptoms are chronic and may not present until at least 3, at least 4, at least 5, at least 6, at least 7, at least 8, at least 9, at least 10, at least 11, or at least 12 months after radiation exposure. In some embodiments, delayed radiation enteropathy symptoms may not present until about 3, about 4, about 5, about 6, about 7, about 8, about 9, about 10, about 11, or about 12 months after radiation exposure. In some embodiments, delayed radiation enteropathy symptoms may not present until about 1 year, about 2 years, about 3 years, about 4 years, or about 5 years after radiation exposure.

In various embodiments, administration of the AP-based agent occurs prior to exposure to radiation, such as, for example, prior to radiotherapy as part of a cancer treatment. In certain embodiments, administration of the AP-based agent occurs at the time of radiation exposure. In various embodiments, administration of the AP-based agent occurs at the time of exposure to radiation, as well as shortly after exposure to radiation. In some embodiments, administration of the AP-based agent occurs shortly after exposure to radiation. In various embodiments, administration of the AP-based agent occurs at the time of exposure to radiation, as well as continued long term after exposure to radiation. In some embodiments, administration of the AP-based agent continues for a long term after exposure to radiation. In various embodiments, administration of the AP-based agent occurs at the onset of delayed radiation enteropathy. In some embodiments, the present invention provides for the treatment and/or administration of an AP-based agent to a subject that has been exposed to or will be exposed to radiation, where the administration of the AP-based agent occurs for at least 1 year, at least 1.5 years, at least 2 years, at least 2.5 years, at least 3 years, at least 3.5 years, 4 years, at least 4.5 years, at least 5 years, at least 5.5 years, at least 6 years, at least 6.5 years, or at least 7 years after the exposure to radiation.

In some embodiments, the present invention relates to a method of treating or preventing radiation-related diseases or disorders in a subject in need thereof. In various embodiments, the radiation-related disease or disorder is a result or side effect of radiotherapy. In some embodiments, the radiotherapy may be part of a cancer treatment, as a primary or adjuvant therapy (e.g. with chemotherapy). In some embodiments, the radiotherapy may be used to prevent tumor recurrence after surgery and/or to remove a primary malignant tumor. In various embodiments, the subject is a cancer patient.

In various embodiments, the present methods reduce or eliminate a side effect of radiotherapy, including acute side effects, long-term side effects), or cumulative side effects. In various embodiments, the present methods reduce or eliminate a local or systemic side effect of radiotherapy. In various embodiments, the side effect of radiotherapy is one or more of fatigue, nausea and vomiting, damage to the epithelial surfaces (e.g., without limitation, moist desquamation), Mouth, throat and stomach sores, Intestinal discomfort (e.g., without limitation, soreness, diarrhea, and nausea), swelling, infertility, fibrosis, epilation, dryness (e.g. without limitation, dry mouth (xerostomia) and dry eyes (xerophthalmia), and dryness of the armpit and vaginal mucosa), lymphedema, heart disease, cognitive decline, radiation enteropathy (e.g. without limitation, atrophy, fibrosis and vascular changes, which may produce malabsorption, diarrhea, steatorrhea and bleeding with bile acid diarrhea and vitamin B12 malabsorption commonly found due to ileal involvement. Pelvic radiation disease includes radiation proctitis, producing bleeding, diarrhoea and urgency, and radiation cystitis.

EXAMPLES

Example 1. Development of IAP Formulation

Freeze Drying of IAP Solution

A solution containing IAP was prepared. 90.9 mL Intestinal Alkaline Phosphatase (IAP) solution (11 mg/mL IAP in 20 mM Tris, 0.1 mM $ZnSO_4$ and 1 mM $MgCl_2$ pH7.5 buffer) was mixed with 2.21 g of HPC (binder), and the subsequent solution was used for freeze drying. The IAP solution was placed in a 7 mL crimp vial with a fill volume was approximately 2 mL/vial and a rubber cap on top. Excipient stabilizing sugars (co-factors), either mannitol, sucrose or trehalose, were dissolved individually in IAP solution at ratios of 1:2 and 1:10 (w/w IAP/co-factor). The composition of the solutions for freeze-drying and the resultant lyophilisate post freeze-drying are displayed in Tables 1 and 2 for each IAP:sugar ratio tested.

TABLE 1

Composition of freeze drying solutions.

| Freeze-dried sample | Solution composition (%) | | | |
|---|---|---|---|---|
| | IAP | Salts | Sugar | Water |
| IAP | 1.09 | 0.25 | 0.00 | 98.66 |
| IAP:Sugar 1:2 | 0.97 | 0.22 | 1.94 | 96.87 |
| IAP:Sugar 1:10 | 0.65 | 0.15 | 6.48 | 92.72 |

TABLE 2

Composition of resulting lyophilisates.

| Freeze-dried sample | Lyophilisate composition (%) | | |
|---|---|---|---|
| | IAP | Salts | Sugar |
| IAP | 81.28 | 18.72 | 0.00 |
| IAP:Sugar 1:2 | 30.96 | 7.13 | 61.91 |
| IAP:Sugar 1:10 | 8.90 | 2.05 | 89.04 |

The freeze drying process was performed using the Christ-Epsilon 2-4 LSC system. In order to test the IAP enzyme activity, two assays were performed—an endpoint IAP activity assay and a kinetic IAP activity assay.

Endpoint IAP Activity Assay

The endpoint IAP activity assay utilized purified intestinal alkaline phosphatase (Sigma #PO114) as a standard by which the activity of samples assayed was quantified. IAP solution was also used as an indicative control; however, it is specified in the results if the values were compared to the IAP solution provided, rather than the Sigma standard. Each sample was tested using 2 replicate wells from which S.D. values were generated. Briefly, the various samples were dissolved in Sodium dihydrogen phosphate buffer ($NaH_2PO_4$ 50 mM+$ZnSO_4$ 0.5 mM, pH 7.0). A standard curve of IAP concentrations of the Sigma standard ranging from 0-20 nM was prepared alongside the IAP samples. 80 μl of samples or standards were added to the wells of a flat bottomed 96-well plate, followed by 50 μl of 5 mM pNPP solution. The plate was then incubated for one hour at 25° C. in a light protected environment. After one hour, 20 μl of stop solution (#Ab83369 composition undisclosed) was added to each well, then the OD at $A_{405}$ was read in a plate reader, and concentrations were derived through comparison to the standard curve generated through a linear fit trend line, the Y=X equation of which was used to calculate concentration values.

Kinetic IAP Activity Assay

The kinetic IAP activity assay utilized purified intestinal alkaline phosphatase (Sigma #PO114) as a control to test the activity of samples assayed. IAP solution was also used as an indicative control; however, it is specified in the results whether the values were compared to the IAP solution or the Sigma standard. Briefly, the various samples were dissolved in diethanolamine based buffer (pH 9.8 at 37° C.) and after five minutes of pre-incubation at 37° C. combined with a 5 mM solution of p-nitrophenyl phosphate (pNPP). After an additional 10 minutes, the colorimetric output at 405 nm as a function of pNPP→NPP dephosporylation via enzyme phosphatase activity was measured every 20 seconds over 5 minutes. This provides a readout of enzyme kinetics over this time period in comparison to the slope generated from the IAP Sigma standard.

The enzyme activity of the powder obtained was measured using the Endpoint Analysis and Kinetic Analysis, and the results are provided in FIG. 2. The cake obtained from freeze drying (IAP only) was also ground gently in a smooth pestle and mortar, and sieved through a 0.5 mm sieve, for ease of filling capsules. Cumulative weights of cake sections weighed were used to calculate [IAP]/section at 22 mg IAP in total, rather than the initial weight post lyophilization due to weight discrepancy arising from hygroscopicity of material. The enzyme activity of the freeze dried IAP alone with manipulation was measured as well, to understand the potential of de-activating the enzyme post-grinding.

FIG. 2 depicts the stability of IAP activity over time within the lyophilisates. As can be seen in the results depicted in FIG. 2, the endpoint analysis shows the activity of the lyophilized IAP solution without the addition of excipient sugars overlapped with the activity of the Sigma standard, at 99.2%. The material displayed a soft spongy consistency, and the activity was similar when the re-suspended material was re-assayed 5 days later at 97.3%. 12 days following re-suspension of the lyophilisates comprising IAP and excipient sugar at the various ratios, the IAP activity remained fairly unchanged at 90.0%. In comparison to the lyophilisate generated from the IAP alone, the inclusion of sugars to the IAP changed the consistency of the lyophilisates, hardening them to a hard, brittle, foamy consistency, but low in density. There was a small drop to 91-94% activity for the majority of sugars and ratios, with the exception of 1:2 sucrose which displayed 99.9% activity, and 1:10 mannitol which showed 78.3%. The mannitol however appeared as an anomalous result with the subsequent assay of the material 5 days later showing an activity of 93.5%. The rest of the lyophilisates remained relatively unchanged when assayed 5 days later, fluctuating between 90-95% activity. At this point the assay was adapted to the kinetic protocol as previously described, for the sake of improved accuracy and efficiency in comparison of the reaction rate based on the activity of the enzyme present rather than the generation of an overall product. Using this assay, the dilution buffer was changed from sodium dihydrogen phosphate (pH 7.0) to diethanolamine buffer pH 9.8. pH 9.8 is preferential to pH 7.0 in maintaining an optimum IAP activity during the assay. Using a fresh batch of lyophilised IAP alone, the activity was assessed to be 91.2%. After 2 weeks, the activity of the IAP alone was 73.2%; however, it is important to note that when compared to the IAP solution, the activity was 97.4%. IAP:trehalose 1:2, initially lyophilised 7 weeks prior, displayed an activity of 76.1%, (100.93% in comparison to the IAP solution). The activity of the IAP:trehalose 1:2 remained consistent after 8 days at 79.8% (114.7% of the IAP solution). The IAP:trehalose 1:10 was assayed and displayed an activity of 74.6% (107.2% of the IAP solution) following 8 weeks of storage at 4° C. The IAP:mannitol 1:2 and 1:10 were assayed after 10 weeks of storage at 4° C., generating an activity of 73.5% at the 1:2 ratio and 66.0% at the 1:10 ratio, (103% and 92.8% of the IAP solution). The IAP:sucrose 1:2 was also assayed, generating an activity of 76.4%, (107.3% that of the IAP solution).

The results show that the IAP enzyme is resilient to freeze drying conditions with and without the addition of excipient sugars. It maintains a high activity over time as a dry lyophilisate stored at 4° C. and after being re-suspended based on the time-periods tested. Despite fluctuations between the activity readout of the IAP solution versus the Sigma standard, the activity appeared high and stable for each lyophilisate tested.

The effects of manipulation on the above-mentioned lyophilisates were also determined and the results are depicted in FIG. 2. The lyophilized IAP solution produced a freeze-dried cake that was ground and sieved as a feasibility study for potential capsule filling. The sample of lyophilisate was initially ground and the activity was tested. A separate sample was then ground using less force and subsequently tested. The reduction in mechanical force between the first and second attempts to grind the material effectively increased the retained IAP activity. After the initial trial of grinding the lyophilisates in a smooth pestle and mortar, the IAP activity was 38.0%. When this was repeated on a separate sample using lower mechanical force, the activity increased to 51.8%, matching the activity of the material after sieving. To test the effects of the incorporation of sugar into the lyophilisate in terms of preserving the activity of the IAP in response to manipulation, the IAP:sucrose 1:2 was ground and the activity compared to the ground IAP alone. The sucrose did improve the preservation of the activity when ground, increasing the activity to 67.4%. When the lyophilisate was physically broken up within the vial with a spatula, and a portion of the cake was assayed, the activity was 51.7%.

A batch of IAP solution alone was also lyophilized, and the cake was removed from the vial, then sectioned into 5 pieces using a scalpel. The activity of these cake sections were assayed, specifically the inner cake, the outer cake, the cake surface and cake base as well as the rinsed empty vial. There was a notable weight difference of 32.9%, in terms of the cumulative weights of the cake sections, in comparison to the weight of the cake directly after lyophilization. The whole lyophilisate was removed from the vial, and the weight was noted. The cake was cut up and weighed over a period of 10-15 minutes. The total weight of the sections surpassed the weight of the whole cake, indicating weight gain as a result of water uptake which stems from high hygroscopicity of the material. As shown in FIG. 2, the activities of the regions of the cakes were significantly lower than when the cake was fully resuspended directly in the vial. Specifically, the activity of the outer cake and cake base, the regions proximal to the glass of the vial had a higher activity of 66.4% and 66.6%, respectively. The inner cake and cake surface demonstrated an activity of 62.2% and 60.5%, respectively, with the rinsed empty vial generating an activity of 3.1%.

Therefore, studies to date showed that freeze-drying the IAP solution yielded unstable powders that could not be further manipulated or processed.

Spray Drying

The IAP solution was spray-dried without additional co-factors. Various spray drying conditions were tested. Illustrative spray drying conditions utilized for the present invention are provided in Table 3.

TABLE 3

Spray drying parameters

| | | |
|---|---|---|
| Bifurcated Air flow = (0.1-.0.14 m³/min) | Air Inlet temperature = 100° C. (±3° C.) | Air Outlet Temperature = 45-48° C. |
| Nozzle Diameter = 0.2 mm | Feed Rate = 1 ml/min | Nozzle Pressure = 1.8 Bar |

The composition of spray drying solution and subsequent spray dried material is depicted in Table 4. A prior IAP composition (IAP:IPMCAS-HF:trehalose:salts at a ratio of 5.1:88.7:5.1:1.2) was prepared as a spray drying solution (see Table 4). First, the excipients were solubilized, namely the trehalose in purified water, followed by addition of the HPMCAS-HF under magnetic stirring. For the solubilization of HPMCAS-HF, the solution was carefully pH adjusted using 1M NaOH up to a final pH of 7.75 to facilitate the solubilization of the material. IAP solution was then added to an aliquot of the appropriate volume of the mixture of excipients, which in turn reduced the pH to 7.57. The enzyme activity of powder obtained was then assayed as per the endpoint and kinetic assays previously mentioned.

and the 1:2 to 78.2%). The material also became moderately granular and slightly waxy over time.

The lyophilisates comprising IAP:mannitol at 1:2 and 1:10 ratios, and IAP:sucrose at a 1:2 ratio were spray dried, following the initial lyophilisation 9 weeks prior. This was carried out to assess the proficiency of the various excipient sugars at conserving IAP activity during spray drying, along

TABLE 4

Composition of spray drying solution and subsequent spray dried material.

| Spray-dried sample | Solution composition (%) | | | | | | Spray-dried material composition (%) | | | | |
|---|---|---|---|---|---|---|---|---|---|---|---|
| | IAP | Salts | HPMCAS-HF | Sugar | NaOH | Water | IAP | Salts | HPMCAS-HF | Sugar | NaOH |
| IAP alone | 1.09 | 0.25 | 0.00 | 0.00 | 0.00 | 98.66 | 81.28 | 18.72 | 0.00 | 0.00 | 0.00 |
| Prior IAP composition* | 0.29 | 0.07 | 5.10 | 0.29 | 0.15 | 94.10 | 4.95 | 1.14 | 86.50 | 4.95 | 2.47 |
| IAP:trehalose 1:2** | 0.39 | 0.09 | 0.00 | 0.79 | 0.00 | 98.72 | 30.96 | 7.13 | 0.00 | 61.91 | 0.00 |
| IAP:trehalose 1:10** | 0.39 | 0.09 | 0.00 | 3.93 | 0.00 | 95.59 | 8.90 | 2.05 | 0.00 | 89.04 | 0.00 |
| IAP:mannitol 1:2** | 0.39 | 0.09 | 0.00 | 0.79 | 0.00 | 98.72 | 30.96 | 7.13 | 0.00 | 61.91 | 0.00 |
| IAP mannitol 1:10** | 0.27 | 0.06 | 0.00 | 2.71 | 0.00 | 96.95 | 8.90 | 2.05 | 0.00 | 89.04 | 0.00 |
| IAP: sucrose 1:2** | 0.39 | 0.09 | 0.00 | 0.79 | 0.00 | 98.72 | 30.96 | 7.13 | 0.00 | 61.91 | 0.00 |

*The sugar quoted in this composition was trehalose
**Each sample had been lyophiised prior to spray drying FIG. 3 represents the IAP activity of the spray dried material over time (stored at 4° C.). Following the spray drying of the prior IAP composition (IAP:HPMCAS-HF: trehalose:salts at a ratio of 5.1:88.7:5.1:1.2), the outlet temperature of which was kept between 45-48° C., the yield was 84.0%, and the IAP activity was about 100% following lengthy solubilization in diethanolamine buffer (pH 9.8, 25° C.), in comparison to 72.4% activity of the spray drying solution. The spray-dried material was stored at 4° C. without desiccation, and when re-tested a week later, the IAP activity had dropped to 79.9%. The material then mildly fluctuated in activity around 75% with 74.4% activity 9 days after spraying, 73.6% after 15 days and 75.8% after 23 days.

A combination of IAP:trehalose at a 1:2 and a 1:10 ratio were then prepared by spray drying without the inclusion of HPMCAS-HF. In an effort to conserve IAP, the samples lyophilized 2 months prior at the 1:2 and 1:10 IAP:trehalose ratios were used for this experiment, following re-suspension with ddH$_2$O. HPMCAS-HF is not a stabilizer of the IAP for spray drying from a formulation perspective. Therefore, the exclusion of HPMCAS-HF would not compromise the IAP activity, and would allow an increase in the drug load of the formulation. It was hypothesized that spray drying the material may increase the resilience of the material to manipulation, which reduced the activity in the case of the lyophilisates. The outlet temperature was maintained between 44.4° C. and 45.5° C. and gave a yield of 79.8% for the IAP:trehalose 1:2 ratio, gener salts at a ratio of 5.1:88.7:5.1:1.2) formulation gained 12.7%. Although the prior IAP composition (IAP: HPMCAS-HF:trehalose:salts at a ratio of 5.1:88.7:5.1:1.2) material showed just a 1.8% weight loss during heating, the weight gain at room temperature in the laboratory was comparable to the IAP:trehalose 1:10. The differential water uptake based on the sample composition agrees with the expected hygroscopicity of the constituents. In the case of the prior IAP composition material, the high HPMCAS-HF proportion resulted in a lower moisture uptake, likely as a result of the low rate of solubilization of the material. The material without HPMCAS-HF and high IAP and trehalose proportions demonstrated a higher moisture uptake based on the affinity of these constituents to water.

TABLE 5a

Spray dried materials were heated at 40° C. for 2 hours and the loss on drying was monitored.

| Sample | Loss on drying (%) |
|---|---|
| Prior IAP composition (IAP:HPMCAS-HF:trehalose:salts at a ratio of 5.1:88.7:5.1:1.2) | 1.82 |
| IAP:Trehalose 1:10 | 6.90 |
| IAP:Trehalose 1:2 | 17.65 |

TABLE 5b

Spray dried materials were exposed to laboratory conditions for 2 hours and the moisture uptake was monitored.

| Sample | Weight gain (%) | Age of material in fridge (days) |
|---|---|---|
| Prior IAP composition (IAP:HPMCAS-HF:trehalose:salts at a ratio of 5.1:88.7:5.1:1.2) | 12.70 | 15 |
| IAP:Trehalose 1:10 | 12.50 | 6 |
| IAP:Trehalose 1:2 | 22.22 | 6 |

Example 2: Tablet Formation

Tableting conditions were assessed to determine parameters. The spray dried prior IAP composition formulation (at ratio of IAP:trehalose:HPMCAS-HF:salts:NaOH 4.95:4.95:86.5:1.14:2.47) was compressed using a Gamlen® D series dynamic powder compaction analyser. The composition appeared slightly different to that which was previously described due to the inclusion of NaOH, which facilitates the solubilization of HPMCAS-HF. A range of different compression forces from 50-200 kp was tested and 1% magnesium stearate was also included as lubricant to facilitate the tableting process. Briefly, 50 mg of the spray-dried material was loaded into a 5 mm diameter die and compressed at a rate of 120 mm/min. In the case of the samples containing 1% magnesium stearate, this was added to an aliquot of the spray dried powder prior to compression. Table 6 depicts IAP activity of prior IAP composition formulation (at ratio of IAP:trehalose:HPMCAS-HF:salts:NaOH 4.95:4.95:86.5:1.14:2.47) tablets were formed at 100 kp and 200 kp compression force. Tablet characteristics were observed and measured, including tablet size, tablet hardness, friability, and dissolution/disintegration.

TABLE 6

IAP activity of prior IAP composition formulation tablets

| | | 1 Day Comparing against | | | |
|---|---|---|---|---|---|
| | | Sigma Standard | | IAP solution | |
| | | Activity (%) | S.D. (%) | Activity (%) | S.D. (%) |
| Tablet (prior IAP formulation at ratio of IAP:trehalose:HPMCAS-HF:salts:NaOH 4.95:4.95:86.5:1.14:2.47) | 100 kp compression | 71.6 | 0.2 | 101.9 | 0.2 |
| | 200 kp compression | 56.4 | 1.24 | 79.0 | 1.7 |

As shown in Table 6, the tablets retained the activity well during 1 day of storage at 4° C., and showed good resilience to the 100 kp compression force with about 100% activity in comparison to the IAP solution and 71.6% when compared to the Sigma standard. One tablet was compressed at each compression force for the activity assay, and the activity was tested using duplicate wells, allowing the generation of S.D values.

Tablets were then prepared using 50 kp and 100 kp compression forces, and comprised the aforementioned prior IAP composition formulation with the addition of 1% magnesium stearate. Two tablets were compressed at each compression force in order to perform tests on both the modified friability and the hardness. FIG. 4 depicts tablets formed through 50 kp and 100 kp of compression force, with an appreciable difference between the tablets in the heights of the tablets—the 100 kp tablet shorter than the 50 kp tablet.

Size and Hardness

The hardness characteristic of tablets is derived from the formulation and compression force and is predictive of friability; thus, it is an important factor to consider for the successful and homogenous coating of tablets.

The size and tensile strength of the tablets were measured through diametral compression based tablet fracture testing using a Gamlen® tablet fracture tester. The force applied at the point at which the tablet fractured was recorded by the instrument. This was carried out on one tablet per formulation in order to demonstrate the force required to fracture the tablet.

As shown below in Table 7, the yield of the tablets in regards to the weight of the powder utilized was 95-100% for all tablets except for the 100 kp compressed tablet used for hardness testing, which was 92.6%. This resulted in tablets of 46.6-49.4 mg. The diameter was standardized to the size of the die and was assumed based on a die diameter of 5 mm. The widths of the tablets were correlative with the compression force with the 50 kp compressed tablets residing between 2.74 mm and 2.87 mm, and the 100 kp compressed tablets between 2.29 mm and 2.42 mm. The relatively low detachment and ejection forces appeared to show sufficient lubrication from the Mg stearate within the formulation. The hardness testing is a tensile test which measures the force required to fracture the tablet. The hardness correlates with the compression force utilized with the 100 kp tablet attaining a hardness approximately twice that of the 50 kp tablet at 4.80 kp and 2.49 kp, respectively. The results provide a readout of the strength of the tablet matrix and may be predictive of the tablet's relative resilience in terms of weight loss when subjected to mechanical agitation and airflow within a coating apparatus.

TABLE 7

Characteristics of tablets formed through 50 kp and 100 kp compression forces

|  | Tablets used for Tensile Hardness Testing | | Tablets used for resistance to coating conditions testing | |
| --- | --- | --- | --- | --- |
| Compression force | 50 kp | 100 kp | 50 kp | 100 kp |
| Weight | 48.3 mg | 46.6 mg | 47.9 mg | 49.4 mg |
| Width (post compression) | 2.87 mm | 2.29 mm | 2.74 mm | 2.42 mm |
| Diameter (in die) | 5 mm | 5 mm | 5 mm | 5 mm |
| Yield | 96.6% | 92.6% | 95.8% | 98.8% |
| Compression force | 51.51 kp | 106.77 kp | 51.73 kp | 105.85 kp |
| Detachment force | 1.43 kp | 0.47 kp | 0.62 kp | n/a |
| Ejection force | 2.15 kp | 1.88 kp | 0.52 kp | 1.11 kp |
| Hardness | 2.49 kp | 4.80 kp | not tested | not tested |

Friability

A tablet friability test using a mini-coater, which has air flow directed from the top and bottom, as well as with agitation, was carried out as a feasibility study to test the resilience of the tablets in terms of destruction and subsequent weight loss of the tablets in response to simulated coating conditions and how compression forces affect these results. The assay carried out assumed spray coating of the tablets, hence the utilization of the same apparatus used for said coating procedure.

Figure 5:
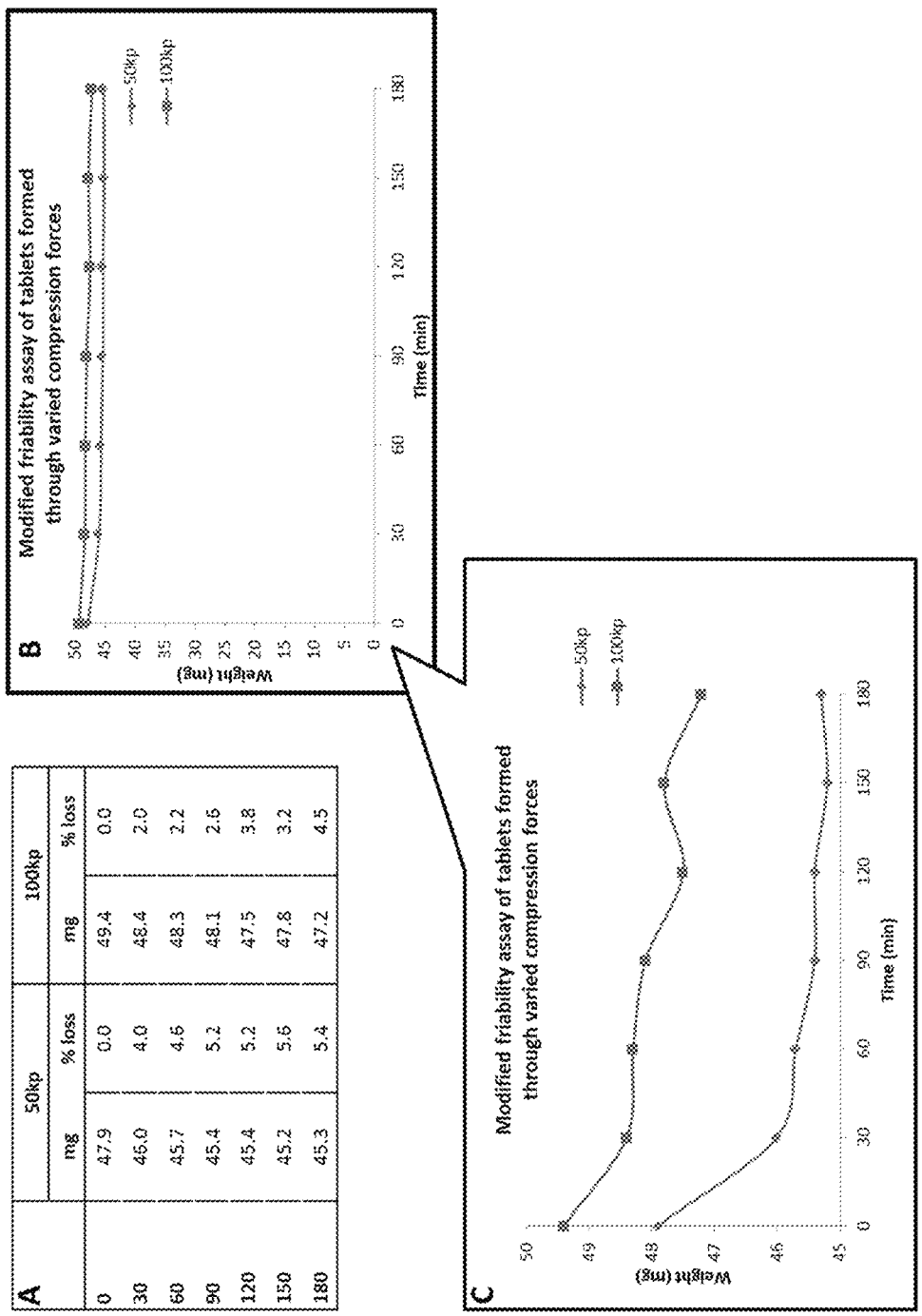
FIG. 5A-C depicts the weight amount and percent weight lost from the 50 kp compressed tablet and the 100 kp tablet over time (FIG. 5A); a schematic of the weight loss exhibited from the tablets (FIG. 5B), and a magnified view of the schematic so that the weight range and weight loss of the tablets is appreciated (FIG. 5C).

As shown in FIG. 5A, the 50 kp compressed tablet lost weight more rapidly in the initial 30 minutes of agitation (4.0%), but slowed after this losing an additional 1.4% over the subsequent 150 minutes, losing a total weight of 5.4%. The 100 kp compressed tablet also lost weight more rapidly in the initial 30 minutes, (2.0%) but slowed and continued to lose weight throughout the 3 hours, reaching an overall weight loss of 4.5%. FIG. 5B depicts a schematic of the weight loss exhibited from the tablets, and FIG. 5C provides a magnified view of the schematic so that the weight range and weight loss of the tablets is appreciated. The results suggest that with just 2% weight loss in the first hour of agitation, the 100 kp compressed tablets appear fairly robust, and viable to be utilized for coating trials. Although there was weight loss over the 3 hours tested, the tablets remained intact, without splitting or disintegrating.

Dissolution/Disintegration

Figure 6:
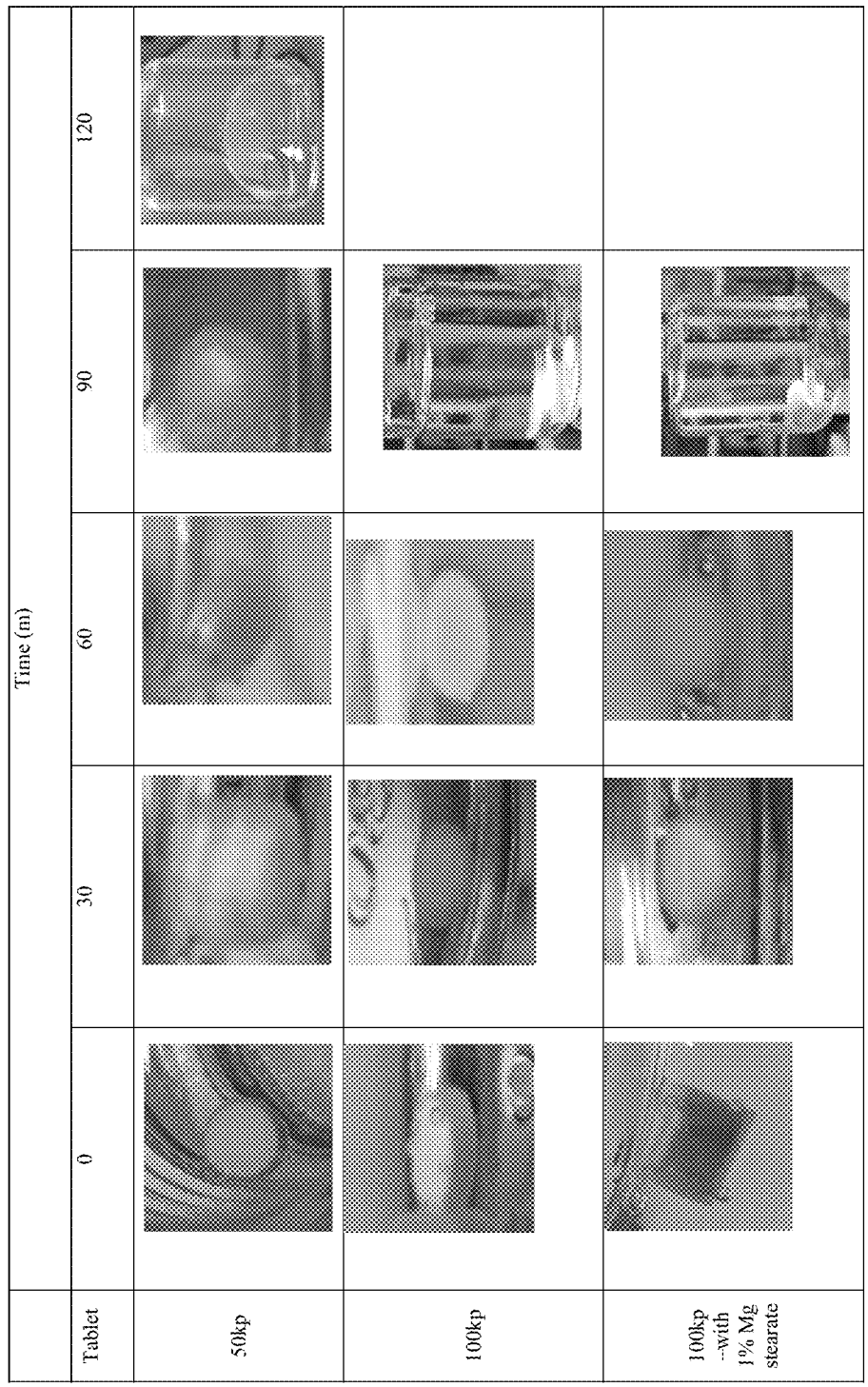
FIG. 6 depicts visual representations of the dissolution of tablets formed by 50 kp and 100 kp compression force in diethanolamine buffer (pH 9.8) under magnetic stirring at 25° C. at predefined time-points throughout the assay

A dissolution/disintegration test was performed under magnetic stirring in 30 mL of pH 9.8 diethanolamine buffer. FIG. 6 depicts visual representations of the dissolution of tablets formed by 50 kp and 100 kp compression force in diethanolamine buffer (pH 9.8) under magnetic stirring at 25° C. at predefined time-points throughout the assay. Unexpectedly, tablets formed through 100 kp compression, with and without 1% Mg stearate, completely solubilized in 90 minutes, whereas the tablet formed through 50 kp compression completely solubilized in 120 minutes. The term "solubilized" was used as the tablets swelled and eroded gradually. Characteristic "disintegration" was not observed, with no tablet fragments present. One would expect that a tablet formed at a lower compression force of 50 kp (hardness 2.49 kg), would be inherently more susceptible to disintegration at a higher rate than a more compact tablet formed at 100 kp (hardness 4.8 kg), due to the proportionality between the tablet density and the compression force. A tablet of a lower density would have a looser conformation of matrix components, thus allowing a higher rate of perfusion through the tablet core and subsequently enact a higher rate of disintegration.

Example 3. Illustrative Tablet bIAP Formulation Results

Bovine IAP formulations were produced and formed into tablets according to the methods described in the aforementioned examples. In order to increase drug loading, concentration of HPMCAS-LF was decreased, and various excipient sugars were utilized as stabilizers, including sucrose and lactose. Various properties were measured in each formulation, including SD powder properties, tablet properties (hardness, friability, and weight loss), IAP activity recovered, and dissolution properties. Compositions of four illustrative formulations (e.g., uncoated tablets) containing different amounts of IAP, HPMCAS-LF, sugar, salts (buffer), Ludipress, and Mg-Stearate are provided in Table 8a, along with the aforementioned properties. Tables 8b and 8c provide the compositions for coated tablet formulations of Tablet #3 and Tablet #4, respectively, when the enteric coating is included.

TABLE 8a

IAP Formulations (Uncoated tablets)

|  | IAP Formulation Number | | | | |
| --- | --- | --- | --- | --- | --- |
|  | Prior IAP[1] | #1 | #2 | #3 | #4 |
| Composition | 5.1% IAP | 30.65% IAP | 35.52% IAP | 39.96% IAP | 44.8% IAP |
|  | 88.7% HPMCAS-HF | 30.65% HPMCAS-LF | 9.9% HPMCAS-LF | 0% HPMCAS-LF | 0% HPMCAS-LF |
|  | 5.1% trehalose | 30.65% sucrose | 35.52% sucrose | 39.96% sucrose | 44.8% lactose |
|  | 1.2% salts (buffer) | 7.05% salts (buffer) | 8.17% salts (buffer) | 9.19% salts (buffer) | 10.21% salts (buffer) |
|  |  | 1% Mg-Stearate | 9.9% Ludipress | 9.9% Ludipress | 1% Mg-Stearate |
|  |  |  | 1% Mg-Stearate | 1% Mg-Stearate |  |

TABLE 8a-continued

IAP Formulations (Uncoated tablets)

| | IAP Formulation Number | | | | |
|---|---|---|---|---|---|
| | Prior IAP[1] | #1 | #2 | #3 | #4 |
| SD Powder Properties | Fine silky powder | Fine | Fine, flowed well, clumped slightly during handling | Extremely fine, flowed very well, no clumping during handling | Fine |
| Tablet Properties | | Minor signs of friability | Minor signs of friability; 10% weight loss; hardness 1.98 kg | Appeared perfect | Appeared perfect; 1% weight loss; hardness 5.63 kg |
| IAP Activity Recovered (*vs IAP sln) | 80% from powder; 100% from tablet | 77.59% from powder; 77.21% from tablet | *84.88% from powder; 77.03% from tablet | *80.84% from powder; 77.82% from tablet | 91.02% from powder; 79.59% from tablet |
| Dissolution Properties (FaSSIF: pH 5.5 for 45 minutes, then pH 6.5 for 120 minutes) | 39% release in 45 minutes; slowly reached 72% at 150 minutes; not fully dissolved at 24 hrs | | 66% released in 15 minutes; plateau at 86% at 30 minutes | 40% released in 30 minutes; plateau at 86% at 75 minutes | 78% release in 15 minutes; plateau at 87% in 60 minutes |

[1]As used herein, the term "prior IAP" refers to this formulation as reflected in Table 8a.

TABLE 8b

IAP Formulation #3 (Coated tablets)

| | Component Tablet #3 Composition (%) | | |
|---|---|---|---|
| Tablet identifier | #3.0% HPMCAS-LF, Sucrose + Ludipress | Tablet + 15% Eudragit L30D 55 | Tablet + 7% HPC + 10% Eudragit L30D 55 |
| IAP | 39.96 | 34.30 | 33.64 |
| Sucrose | 39.96 | 34.30 | 33.64 |
| Salts (from IAP solution) | 9.19 | 7.89 | 7.74 |
| Tris | 8.79 | 7.55 | 7.40 |
| MgCl2 | 0.34 | 0.29 | 0.29 |
| ZnSO4 | 0.06 | 0.05 | 0.05 |
| Ludipress | 9.9 | 8.50 | 8.34 |
| Magnesium stearate | 1 | 0.86 | 0.84 |
| HPC | — | — | 5.89 |
| TEC | — | 1.29 | 0.90 |
| L30D55 | — | 12.88 | 9.01 |
| Total | 100.0 | 100.0 | 100.0 |

TABLE 8c

IAP Formulation #3 (Coated tablets)

| | Component Tablet #4 Composition (%) | | |
|---|---|---|---|
| Tablet identifier | #4.0% HPMCAS-LF + Lactose | Tablet + 10% Eudragit L30D 55 | Tablet + 7% HPC + 10% Eudragit L30D 55 |
| IAP | 44.4 | 40.00 | 37.38 |
| Lactose | 44.4 | 40.00 | 37.38 |
| Salts (from IAP solution: Tris, MgCl2, ZnSO4) | 10.21 | 9.20 | 8.60 |
| Tris | 9.76 | 8.79 | 8.22 |
| MgCl2 | 0.38 | 0.34 | 0.32 |
| ZnSO4 | 0.07 | 0.06 | 0.06 |
| Magnesium stearate | 1 | 0.90 | 0.84 |

TABLE 8c-continued

IAP Formulation #3 (Coated tablets)

| | Component Tablet #4 Composition (%) | | |
|---|---|---|---|
| Tablet identifier | #4.0% HPMCAS-LF + Lactose | Tablet + 10% Eudragit L30D 55 | Tablet + 7% HPC + 10% Eudragit L30D 55 |
| HPC | 0 | 0.00 | 5.89 |
| TEC | 0 | 0.90 | 0.90 |
| L30D55 | 0 | 9.01 | 9.01 |
| Total | 100.0 | 100.0 | 100.0 |

Figure 7:
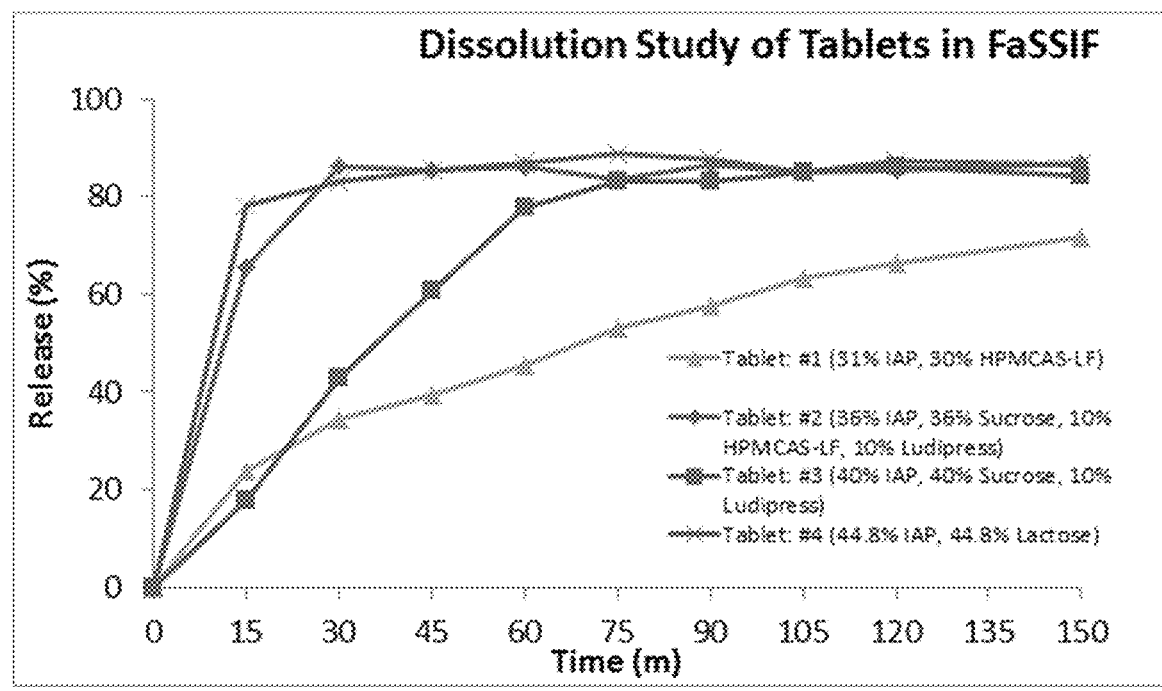
FIG. 7 depicts the dissolution rate (% release over time) of the four tableted formulations previously discussed.

A disintegration assay was performed using a disintegration apparatus combined with a biologically relevant FaSSIF buffer for uncoated tablets in order to assess the dissolution rate of the different compositions listed in Table 8a above. FIG. 7 depicts the dissolution rate (% release over time) of the four tableted formulations previously discussed. As shown in both Table 8a and FIG. 7, Formulation Tablets #2 and #4, in particular, exhibited fast-release, or "burst," release profiles, i.e. 78% release in 15 minutes and 87% release at 60 minutes for Tablet #4. Tablet #1 exhibits a sustained release profile, and Tablet #3 fell between sustained release and burst release profiles.

Tablet Formulations #2 and #4 underwent additional fracture testing and modified friability assays. The modified friability assay mirrored the parameters used for previous tablet coating trials: (1) 30 minutes of agitation at 11%, a fan speed of 55% and at 40° C.; (2) 1 hour without agitation, a fan speed of 55% and at 40° C.; (3) 30 minutes of 5% agitation, a fan speed of 50% and at 40° C. As shown in Table 9, Formulation Tablet #4 was found to be much harder than Formulation Tablet #2, with a hardness of 5.63 kg as compared to 1.98 kg. Table 10 depicts the results of the modified friability assay correlated with the hardness of the tablets, with Formulation Tablet #2 losing about 11% over the assay in comparison to Tablet #4 which lost about 1%. FIG. 8A depicts the weight change of Tablets #2 and #4 over time, and FIG. 8B shows the % weight that was lost from Tablets #2 and #4 over time.

TABLE 9

Tablet properties pertaining to Tablet Compositions #2 and #4

| Tablet Composition | Tablet # | Tablet weight (mg) | Tablet Dimensions (w/h (mm)) | Tablet Hardness (kg) |
|---|---|---|---|---|
| #2) 36% IAP, 10% HPMCAS-LF, 36% Sucrose, 10% Ludipress, 1% Mg Stearate | 1 | 50.1 | 5.05/2.80 | n/a |
| | 2 | 51.5 | 5.06/2.84 | 1.98 |
| #4) 44% IAP, 44% Lactose 1% Mg Stearate | 3 | 49.9 | 5.06/3.06 | n/a |
| | 4 | 49.2 | 5.06/3.00 | 5.63 |

TABLE 10

Percent weight loss over time in Tablet Formulations #2 and #4

| | #2 | | #4 | |
|---|---|---|---|---|
| Time (m) | mg | % loss | mg | % loss |
| 0 | 49.8 | 0 | 49.7 | 0 |
| 15 | 47.1 | 5.4 | 49.6 | 0.2 |
| 30 | 46 | 7.6 | 49.1 | 1.2 |
| 45 | 46.1 | 7.4 | 49.2 | 1.0 |
| 60 | 45.8 | 8.0 | 49.4 | 0.6 |
| 75 | 45.4 | 8.8 | 49.8 | −0.2 |
| 90 | 44.8 | 10.0 | 49.4 | 0.6 |
| 105 | 44.5 | 10.6 | 49.2 | 1.0 |
| 120 | 44.5 | 10.6 | 49.8 | −0.2 |

Example 4. Enteric Coating of Tablets

Tablets were formed via the procedure of Example 2 using the illustrative IAP formulation Number 4 of Example 3 (see Table 8a, #4). A formulation composed of 44.8% IAP, 44.8% lactose, and 10.3% salts was spray-dried at about 45° C. or below, and a yield of about 100% was observed. 100 Mg-Stearate was added to the spray-dried material and mixed on a tubular mixer and vortex. After, tablets were formed with compressing at 100 kg. The average weight of each tablet was 49.25 mg, and the diameter/height was 5.07/3.36 mm. Furthermore, the tablets appeared pristine with no signs of friability.

The tablets were then split into two groups comprising 5 tablets each. Group #1 was coated with a 10% weight gain of Eudragit L 30 D 55. Group #2 was coated with a 7% weight gain HPC subcoat (to isolate the IAP from the acidic L 30 D 55 coating), followed by a 10% weight gain of Eudragit L 30 D 55. The compositions of each group of tablets is provided in Table 8c.

An IAP activity assay was performed after the tablets had been coated. The results of the activity assay are depicted in Table 11.

TABLE 11

IAP % activity of IAP solution after enteric coating.

| Sample | Activity (%) | S.D. |
|---|---|---|
| Sigma Std | 100.00 | 0.99 |
| IAP solution | 98.84 | 1.19 |
| Spray dried material | 63.58 | 0.44 |
| Tablet Group 1 - 1 layer enteric coat | 72.44 | 1.96 |
| Tablet Group 2 - Isolation layer + enteric | 69.89 | 1.94 |

Tablet dissolution was then observed at 37° C. and 200 RPM orbital agitation. To test the resilience of the different coatings, the dissolution was carried out in FaSSGF ("Fasted State Simulated Gastric Fluid", pH 1.6) for 2 hours, followed by an addition of FaSSIF ("Fasted State Simulated Intestinal Fluid"), with a pH adjustment to pH 5.5 for 45 minutes, and finally, with an additional pH adjustment to pH 6.5. The release of IAP from the tablets was monitored through UV absorbance, and the activity was monitored through IAP activity assays.

Figure 9:
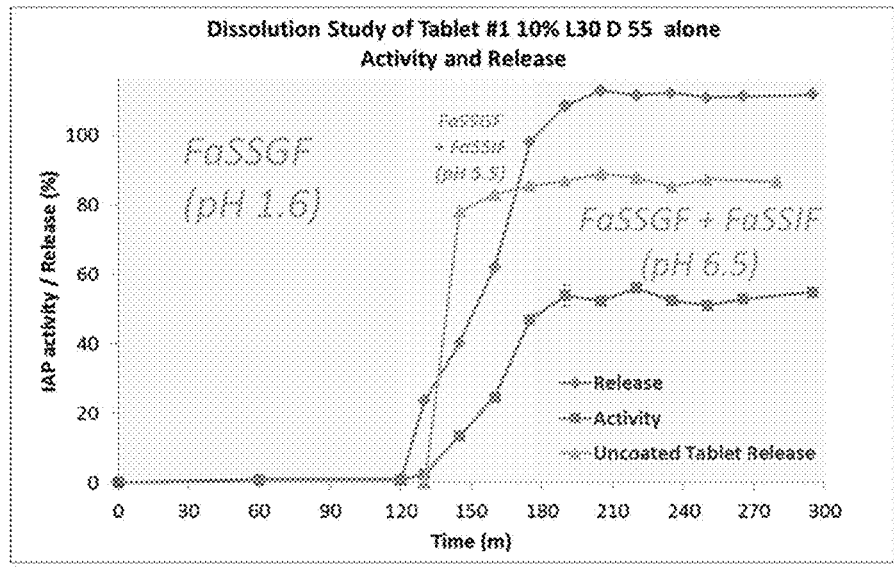
FIGS. 9A-B depict the results of a dissolution study, in which the protein release (A280) and enzyme activity from tablet #1 comprising the 10% L 30 D 55 coating alone were monitored over time at varying pH (FIG. 9A); and raw data associated with the dissolution test of tablet #1 (L30 D 55 coating alone), including 1) raw activity, 2) the activity as a percentage of total activity of the tablet, and 3) the release as discerned through UV absorbance (FIG. 9B).

FIG. 9A displays the protein release (A280) and enzyme activity from Tablet Group #1 comprising the 10% L 30 D 55 coating alone. No release was observed in the first 2 h in FaSSGF, validating its resilience when challenged with simulated gastric conditions. The release increased to 60% after 45 minutes at pH 5.5 and further to about 100% after 15-30 minutes at pH 6.5. The activity increased rapidly after the addition of FaSSIF to 46.9% after 45 minutes at pH 5.5, and plateaued at about 53% for the remainder of the dissolution. For comparative purposes, the figure shows the release profile as calculated through UV absorbance of the uncoated tablet from the previous dissolution repeat of the same formulation composition as well. The uncoated tablet was not exposed to FaSSGF, but was added to FaSSIF pH 5.5 directly, in advance to the pH change to 6.5 after 45 minutes. The profile displayed a burst release in the first 15 minutes of dissolution to just below 80% in FaSSIF pH 5.5, and then rapidly reached a plateau of about 87% release. FIG. 9B depicts the Tablet Group #1 (L30 D 55 coating alone) raw data comprising 1) raw activity, 2) the activity as a percentage of total activity of the tablet, and 3) the release as discerned through UV absorbance.

Figure 10:
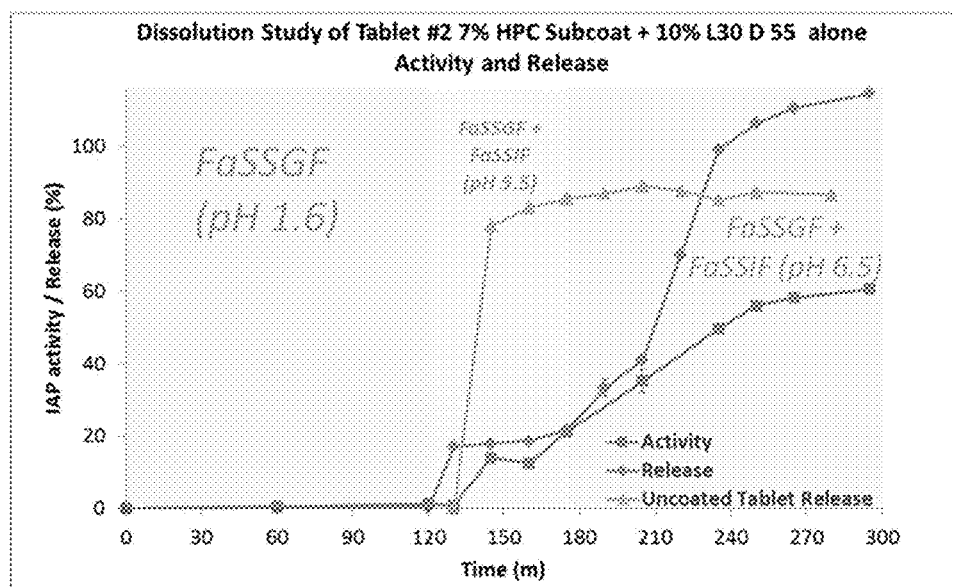
FIGS. 10A-B display the results of a dissolution study, in which the protein release (A280) and enzyme activity from tablet #2 comprising the 7% HPC subcoat and the 10% L 30 D 55 coating were monitored over time at varying pH (FIG. 10A); and raw data associated with the dissolution test of tablet #2 (7% HPC subcoat and 10% L 30 D 55 coating), including 1) raw activity, 2) the activity as a percentage of total activity of the tablet, and 3) the release as discerned through UV absorbance (FIG. 10B).

FIG. 10 displays the release and activity from Tablet Group #2 comprising the 7% HPC subcoat and the 10% L 30 D 55 coating. No release was observed in the first 2 h in FaSSGF, validating its resilience to simulated gastric condition. The release increased to 17% after the pH change to 5.5 and plateaued until the pH was further increased to 6.5. The release increased to 41.2% after 30 minutes at pH 6.5, then rapidly increased to 100% after 1 hour in pH 6.5, and finally plateaued after 295 minutes. FIG. 10*b* depicts the Tablet Group #2 (HPC subcoat+L30 D 55 coating) raw data comprising 1) raw activity, 2) the activity as a percentage of total activity of the tablet, and 3) the release as discerned through UV absorbance.

The activity increased rapidly to 46.9% when FaSSIF was added after 45 minutes at pH 5.5, and plateaued at about 53% for the remainder of the dissolution. The activity results were slightly delayed in comparison to those of the release, with an increase to 14% only after 15 minutes at pH 5.5. The activity increased to 58% after 45 minutes at pH 6.5, and finally plateaued there for the remainder of the dissolution. Without wishing to be bound to any theory, the difference in release, and activity rates between Tablet Group #1 and Tablet Group #2 at pH 5.5 may be a result of dissolution of the HPC subcoat.

Example 5. IAP Spray-Dried Powder Maintains Activity Over Extended Duration

Activity assays were run at 5 weeks or 7 weeks on the illustrative spray-dried powder formulations of Table 8a. The results of the IAP activity assays are depicted in Table 12 below.

TABLE 12

IAP activity of spray-dried powder over time

| | Time (weeks) | 0 | 7 | 9 | 12 |
|---|---|---|---|---|---|
| Formulation #1 | Activity (%) | 81.2 | 67.6 | 64.9 | 60.1 |
| | S.D. (%) | 2.4 | 0.3 | 1.2 | 1.0 |
| | Time (weeks) | 0 | 5 | 7 | 10 |
| Formulation #2 | Activity (%) | 72.3 | 68.7 | 66.6 | 59.8 |
| | S.D. (%) | 0.4 | 0.5 | 0.8 | 1.3 |
| | Time (weeks) | 0 | 5 | 7 | 10 |
| Formulation #3 | Activity (%) | 68.85 | 67.80 | 64.56 | 59.84 |
| | S.D. (%) | 0.59 | 0.74 | 0.54 | 0.42 |
| | Time (weeks) | 0 | | | 2 |
| Formulation #3 Repeat | Activity (%) | 75.8 | | | 61.1 |
| | S.D. (%) | 0.1 | | | 1.4 |
| | Time (weeks) | 0 | 7 | 9 | 12 |
| Formulation #4 | Activity (%) | 95.2 | 71.0 | 64.9 | 62.7 |
| | S.D. (%) | 0.2 | 1.2 | 0.6 | 0.4 |
| | Time (weeks) | 0 | 1 | 2 | 4 | 7 |
| Formulation #4 Repeat | Activity (%) | 63.6 | 65.9 | 69.5 | 65.4 | 61.5 |
| | S.D. (%) | 0.4 | 0.5 | 0.5 | 0.3 | 1.1 |

Example 6. Activity and Disintegration of Spray-Dried IAP Tablet Formulations with Various Levels of HPMCAS-HF IAP tablets were formed with IAP:sucrose 1:1 ratios in combination with 3000 and 10% HPMCAS-HF. The compositions of the tablet formulations are provided in Table 13.

TABLE 13

Composition of IAP formulations with 30% and 10% HPMCAS-HF

| | Composition (%) | |
|---|---|---|
| Component | 30% HPMCAS | 10% HPMCAS |
| IAP | 30.52 | 40.00 |
| HPMCAS-HF | 30.52 | 9.90 |
| Sucrose | 30.52 | 40.00 |
| Salts (from IAP solution), including Tris, MgCl2, and/or ZnSO4 | 7.02 | 9.20 |
| Magnesium stearate | 1.00 | 1.00 |

A visual disintegration study was conducted on tablets containing about 30% and about HPMCAS-HF with or without 500 disintegrant. The tablets were tested under disintegration conditions in Fasted State Simulated Intestinal Fluid at pH 6.5 until the tablets were no longer visible. The results showed that the tablets containing about 30% HPMCAS-HF took about 30 minutes to disintegrate, while the tablets containing about 10% HPMCASE-HF took about 15 minutes to disintegrate, and IAP activity was retained in both formulations from about 70-90%.

A dissolution study was performed in which a 30% HPMCAS-HF tablet (50 mg tablet) was used for dissolution in FaSSIF (pH 6.5, 37° C.) using an orbital shaker in 20 ml fluid volume in a 60 ml vessel under agitation at 200 RPM. The total IAP concentration was 0.77 mg/ml for the 30% HPMCAS-HF tablet. Results showed the 30% HPMCAS-HF formulation released IAP gradually over the course of 2 hours, reaching a peak release of 67% and disintegrating completely.

Example 7. Stability of IAP Tablet Formulation Activity is Maintained Over Extended Duration of Time The IAP enzyme activity of the tablet formulations described previously was measured after various storage conditions.

Figure 11:
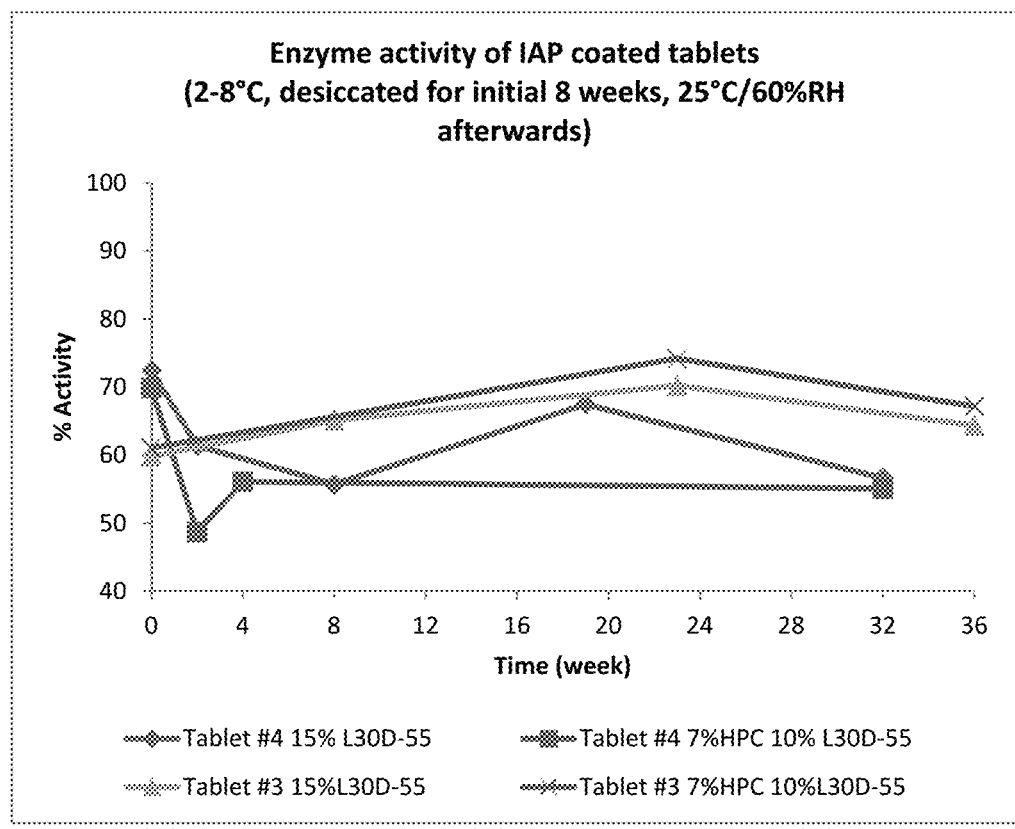
FIG. 11 depicts stability of IAP activity in coated tablets stored at 2-8° C. under dessication and 25° C./60% RH.

The data provided in FIG. 11 and Table 14 shows that there was not a significant decrease in IAP activity from either single layer or double layer coated tablets over 8 weeks at 25° C./60% RH. FIG. 11 depicts stability of IAP activity in coated tablets stored at 2-8° C. under dessication and 25° C./60% RH.

After the initial 8 weeks, the tablets were stored at refrigerated temperatures under dessication at 2-8° C. During this time, the IAP activity did not further decline in value, which indicated stable tablet formulations after approximately 8 months of production.

TABLE 14

Stability of IAP activity in coated tablets stored at 25° C./60% RH and then at 2-8° C. under dessication

| Time point | Sample (stored under 25° C./60% RH) | | % Activity against Sigma standard |
|---|---|---|---|
| 0 weeks | IAP solution (control) | | 72.05 |
| | Tablet #4 | 15% L30D-55 | 72.44 |
| | | 7% HPC 10% L30D-55 | 69.89 |
| | Tablet #3 | 15% L30D-55 | 59.84 |
| | | 7% HPC 10% L30D-55 | 61.07 |
| 2 weeks | Tablet #4 | 15% L30D-55 | 61.37 |
| | | 7% HPC 10% L30D-55 | 48.73 |
| 4 weeks | Tablet #4 | 7% HPC 10% L30D-55 | 56.11 |
| 8 weeks | Tablet #3 | 15% L30D-55 | 65.13 |
| | Tablet #4 | 15% L30D-55 | 55.73 |

After 8 weeks, samples were stored at refrigerated temperatures under desiccation

| Sample age | Sample | | % Activity |
|---|---|---|---|
| 19 weeks | Tablet #4 | 15% L30D-55 | 67.46 |
| 23 weeks | Tablet #3 | 15% L30D-55 | 70.22 |
| | | 7% HPC 10% L30D-55 | 74.20 |
| 32 weeks | Tablet #4 | 15% L30D-55 | 56.63 |
| | | 7% HPC 10% L30D-55 | 55.09 |
| 36 weeks | Tablet #3 | 15% L30D-55 | 64.35 |
| | | 7% HPC 10% L30D-55 | 67.18 |

Definitions

As used herein, the terms "patient" and "subject" are used interchangeably. In some embodiments, the subject and/or animal refers to a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal refers to a nonmammal, such, for example, a zebrafish. In various embodiments, methods of the invention are useful in treatment of a human subject. In some embodiments, the human is a pediatric human. In other embodiments, the human is an adult human. In other embodiments, the human is a geriatric human. In other embodiments, the human may be referred to as a patient. In some embodiments, the human is a female. In some embodiments, the human is a male. In certain embodiments, the human is a patient with a feeding tube. In certain embodiments, the human is a patient who cannot swallow. In certain embodiments, the human has an age in a range of from about less than 1 day to about 1 day old, from about 1 to about 7 days old, from about 7 to about 14 days old, from about 14 to about 21 days old, from about 21 to about 29 days old, from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old. In some embodiments, the human patient is a premature baby.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

The term "pharmaceutically acceptable salt," as used herein, refers to a salt of the alkaline phosphatases having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl) amine; N-methyl-D-glucamine; and amino acids such as arginine, lysine, and the like.

As used herein, "pH independent" refers to the water permeability of the polymer used for enteric coating and its ability to release pharmaceutical ingredients is not a function of pH and/or is only very slightly dependent on pH. For example, by way of non-limiting example, the enteric coating may degrade as a function of time when in aqueous solution without regard to the pH and/or presence of enzymes in the solution.

By "modification" herein refers to an amino acid substitution, insertion, and/or deletion in a polypeptide sequence or an alteration to a moiety chemically linked to a protein. For example, a modification may be an altered carbohydrate or PEG structure attached to a protein. An "amino acid modification" herein refers to an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

As used herein, "amino acid substitution" or "substitution" refers to the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution. In some embodiments, the amino acid substitutions may include conservative and/or non-conservative substitutions. "Conservative substitutions" may be made, for instance, on the basis of similarity in polarity, charge, size, solubility, hydrophobicity, hydrophilicity, and/or the amphipathic nature of the amino acid residues involved. For example, the exchange of Asp by Glu retains one negative charge in the so modified polypeptide. In addition, glycine and proline may be substituted for one another based on their ability to disrupt α-helices. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe. As used herein, "non-conservative substitutions" are defined as exchanges of an amino acid by another amino acid listed in a different group of the six standard amino acid groups (1) to (6) shown above.

The term "amino acid insertion" or "insertion" as used herein refers to the addition of an amino acid sequence at a particular position in a parent polypeptide sequence.

The term "amino acid deletion" or "deletion" as used herein refers to the removal of an amino acid sequence at a particular position in a parent polypeptide sequence.

As used herein, the term "variant protein" or "protein variant", or "variant" refers to a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g., from about one to about seventy amino acid modifications, and preferably from about one to about five amino acid modifications compared to the parent.

"Percent (%) amino acid sequence identity" with respect to a protein sequence is herein defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNAS-TAR) software. Those skilled in the art can determine appropriate parameters for measuring alignment, including any algorithms needed to achieve maximal alignment over the full length of the sequences being compared. One particular program is the ALIGN-2 program outlined at paragraphs [0279] to [0280] of US Pub. No. 20160244525, hereby incorporated by reference.

The degree of identity between an amino acid sequence of the present invention ("invention sequence") and the parental amino acid sequence is calculated as the number of exact matches in an alignment of the two sequences, divided by the length of the "invention sequence," or the length of the parental sequence, whichever is the shortest. The result is expressed in percent identity.

In some embodiments, two or more amino acid sequences are at least 50%, 60%, 70%, 80%, or 90% identical. In some embodiments, two or more amino acid sequences are at least 95%, 97%, 98%, 99%, or even 100% identical.

The term "Fc domain" as used herein refers to the CH2-CH3 domain, optionally including a hinge domain, generally derived from the Fc domain and/or hinge region of an antibody (e.g., of IgG, IgA, IgD, and IgE, inclusive of subclasses (e.g. IgG1, IgG2, IgG3, and IgG4, and IgA1 and IgA2)). Accordingly, "CH" domains in the context of IgG are as follows: "CH2" refers to positions 237-340 according to the EU index as in Kabat, and "CH3" refers to positions 341-447 according to the EU index as in Kabat. By "hinge" or "hinge region" or "antibody hinge region" or "immunoglobulin hinge region" herein is meant the flexible polypeptide comprising the amino acids between the first and second constant domains of an antibody. Structurally, the IgG CH1 domain ends at EU position 220, and the IgG CH2 domain begins at residue EU position 237. Thus for IgG the antibody hinge is herein defined to include positions 221 (D221 in IgG1) to 236 (G236 in IgG1), wherein the numbering is according to the EU index as in Kabat. In some embodiments, for example in the context of an Fc region, the lower hinge is included, with the "lower hinge" generally referring to positions 226 or 230.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

SEQUENCE LISTING

```
<160> NUMBER OF SEQ ID NOS: 37

<210> SEQ ID NO 1
<211> LENGTH: 528
<212> TYPE: PRT
<213> ORGANISM: Artificial Sequence
<220> FEATURE:
<223> OTHER INFORMATION: Synthetic polymer

<400> SEQUENCE: 1

Met Gln Gly Pro Trp Val Leu Leu Leu Gly Leu Arg Leu Gln Leu
1               5                   10                  15

Ser Leu Gly Val Ile Pro Ala Glu Glu Glu Asn Pro Ala Phe Trp Asn
            20                  25                  30
```

```
Arg Gln Ala Ala Glu Ala Leu Asp Ala Ala Lys Lys Leu Gln Pro Ile
     35                  40                  45
Gln Lys Val Ala Lys Asn Leu Ile Leu Phe Leu Gly Asp Gly Leu Gly
     50                  55                  60
Val Pro Thr Val Thr Ala Thr Arg Ile Leu Lys Gly Gln Lys Asn Gly
 65                  70                  75                  80
Lys Leu Gly Pro Glu Thr Pro Leu Ala Met Asp Arg Phe Pro Tyr Leu
                 85                  90                  95
Ala Leu Ser Lys Thr Tyr Asn Val Asp Arg Gln Val Pro Asp Ser Ala
             100                 105                 110
Ala Thr Ala Thr Ala Tyr Leu Cys Gly Val Lys Ala Asn Phe Gln Thr
             115                 120                 125
Ile Gly Leu Ser Ala Ala Ala Arg Phe Asn Gln Cys Asn Thr Thr Arg
     130                 135                 140
Gly Asn Glu Val Ile Ser Val Met Asn Arg Ala Lys Gln Ala Gly Lys
145                 150                 155                 160
Ser Val Gly Val Val Thr Thr Thr Arg Val Gln His Ala Ser Pro Ala
                 165                 170                 175
Gly Thr Tyr Ala His Thr Val Asn Arg Asn Trp Tyr Ser Asp Ala Asp
             180                 185                 190
Met Pro Ala Ser Ala Arg Gln Glu Gly Cys Gln Asp Ile Ala Thr Gln
             195                 200                 205
Leu Ile Ser Asn Met Asp Ile Asp Val Ile Leu Gly Gly Gly Arg Lys
     210                 215                 220
Tyr Met Phe Pro Met Gly Thr Pro Asp Pro Glu Tyr Pro Ala Asp Ala
225                 230                 235                 240
Ser Gln Asn Gly Ile Arg Leu Asp Gly Lys Asn Leu Val Gln Glu Trp
                 245                 250                 255
Leu Ala Lys His Gln Gly Ala Trp Tyr Val Trp Asn Arg Thr Glu Leu
             260                 265                 270
Met Gln Ala Ser Leu Asp Gln Ser Val Thr His Leu Met Gly Leu Phe
             275                 280                 285
Glu Pro Gly Asp Thr Lys Tyr Glu Ile His Arg Asp Pro Thr Leu Asp
     290                 295                 300
Pro Ser Leu Met Glu Met Thr Glu Ala Ala Leu Arg Leu Leu Ser Arg
305                 310                 315                 320
Asn Pro Arg Gly Phe Tyr Leu Phe Val Glu Gly Gly Arg Ile Asp His
                 325                 330                 335
Gly His His Glu Gly Val Ala Tyr Gln Ala Leu Thr Glu Ala Val Met
             340                 345                 350
Phe Asp Asp Ala Ile Glu Arg Ala Gly Gln Leu Thr Ser Glu Glu Asp
             355                 360                 365
Thr Leu Thr Leu Val Thr Ala Asp His Ser His Val Phe Ser Phe Gly
     370                 375                 380
Gly Tyr Thr Leu Arg Gly Ser Ser Ile Phe Gly Leu Ala Pro Ser Lys
385                 390                 395                 400
Ala Gln Asp Ser Lys Ala Tyr Thr Ser Ile Leu Tyr Gly Asn Gly Pro
                 405                 410                 415
Gly Tyr Val Phe Asn Ser Gly Val Arg Pro Asp Val Asn Glu Ser Glu
             420                 425                 430
Ser Gly Ser Pro Asp Tyr Gln Gln Gln Ala Ala Val Pro Leu Ser Ser
             435                 440                 445
```

Glu Thr His Gly Gly Glu Asp Val Ala Val Phe Ala Arg Gly Pro Gln
450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Cys Thr Thr Asp Ala Ala His Pro Val Ala Ala Ser Leu
            500                 505                 510

Pro Leu Leu Ala Gly Thr Leu Leu Leu Gly Ala Ser Ala Ala Pro
            515                 520                 525

<210> SEQ ID NO 2
<211> LENGTH: 533
<212> TYPE: PRT
<213> ORGANISM: Artificial Sequence
<220> FEATURE:
<223> OTHER INFORMATION: Synthetic polymer

<400> SEQUENCE: 2

Met Gln Gly Ala Cys Val Leu Leu Leu Gly Leu His Leu Gln Leu
1               5                   10                  15

Ser Leu Gly Leu Ile Pro Ala Glu Glu Asn Pro Ala Phe Trp Asn
            20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
        50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Arg Thr
        115                 120                 125

Ile Gly Val Ser Ala Ala Arg Tyr Asn Gln Cys Asn Thr Thr Arg
        130                 135                 140

Gly Asn Glu Val Thr Ser Val Ile Asn Arg Ala Lys Lys Ala Gly Lys
145                 150                 155                 160

Ala Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Lys Asn Gly Cys Gln Asp Ile Ala Ala Gln
        195                 200                 205

Leu Val Tyr Asn Met Asp Ile Asp Val Ile Leu Gly Gly Gly Arg Met
    210                 215                 220

Tyr Met Phe Pro Glu Gly Thr Pro Asp Pro Glu Tyr Pro Asp Asp Ala
225                 230                 235                 240

Ser Val Asn Gly Val Arg Lys Asp Lys Gln Asn Leu Val Gln Glu Trp
                245                 250                 255

Gln Ala Lys His Gln Gly Ala Gln Tyr Val Trp Asn Arg Thr Ala Leu
            260                 265                 270

Leu Gln Ala Ala Asp Asp Ser Ser Val Thr His Leu Met Gly Leu Phe
        275                 280                 285

Glu Pro Ala Asp Met Lys Tyr Asn Val Gln Gln Asp His Thr Lys Asp
290                 295                 300

Pro Thr Leu Ala Glu Met Thr Glu Ala Ala Leu Gln Val Leu Ser Arg
305                 310                 315                 320

Asn Pro Arg Gly Phe Tyr Leu Phe Val Glu Gly Gly Arg Ile Asp His
            325                 330                 335

Gly His His Asp Gly Lys Ala Tyr Met Ala Leu Thr Glu Ala Ile Met
                340                 345                 350

Phe Asp Asn Ala Ile Ala Lys Ala Asn Glu Leu Thr Ser Glu Leu Asp
            355                 360                 365

Thr Leu Ile Leu Val Thr Ala Asp His Ser His Val Phe Ser Phe Gly
370                 375                 380

Gly Tyr Thr Leu Arg Gly Thr Ser Ile Phe Gly Leu Ala Pro Gly Lys
385                 390                 395                 400

Ala Leu Asp Ser Lys Ser Tyr Thr Ser Ile Leu Tyr Gly Asn Gly Pro
                405                 410                 415

Gly Tyr Ala Leu Gly Gly Gly Ser Arg Pro Asp Val Asn Gly Ser Thr
                420                 425                 430

Ser Glu Glu Pro Ser Tyr Arg Gln Gln Ala Ala Val Pro Leu Ala Ser
                435                 440                 445

Glu Thr His Gly Gly Glu Asp Val Ala Val Phe Ala Arg Gly Pro Gln
450                 455                 460

Ala His Leu Val His Gly Val Gln Glu Glu Thr Phe Val Ala His Ile
465                 470                 475                 480

Met Ala Phe Ala Gly Cys Val Glu Pro Tyr Thr Asp Cys Asn Leu Pro
                485                 490                 495

Ala Pro Ala Thr Ala Thr Ser Ile Pro Asp Ala Ala His Leu Ala Ala
                500                 505                 510

Ser Pro Pro Pro Leu Ala Leu Leu Ala Gly Ala Met Leu Leu Leu Leu
                515                 520                 525

Ala Pro Thr Leu Tyr
                530

<210> SEQ ID NO 3
<211> LENGTH: 530
<212> TYPE: PRT
<213> ORGANISM: Artificial Sequence
<220> FEATURE:
<223> OTHER INFORMATION: Synthetic polymer

<400> SEQUENCE: 3

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
                20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
        50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
                100                 105                 110

-continued

```
Gly Thr Ala Thr Ala Tyr Leu Cys Gly Val Lys Gly Asn Tyr Lys Thr
            115                 120                 125

Ile Gly Val Ser Ala Ala Arg Tyr Asn Gln Cys Asn Thr Thr Ser
130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Arg Met
210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
        290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335

Gly His His Glu Gly Lys Ala Tyr Met Ala Leu Thr Asp Thr Val Met
            340                 345                 350

Phe Asp Asn Ala Ile Ala Lys Ala Asn Glu Leu Thr Ser Glu Leu Asp
        355                 360                 365

Thr Leu Ile Leu Ala Thr Ala Asp His Ser His Val Phe Ser Phe Gly
370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Leu Arg Pro Asp Val Asn Asp Ser Ile
            420                 425                 430

Ser Glu Asp Pro Ser Tyr Arg Gln Gln Ala Ala Val Pro Leu Ser Ser
        435                 440                 445

Glu Ser His Gly Gly Glu Asp Val Ala Val Phe Ala Arg Gly Pro Gln
        450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
                485                 490                 495

Ala Pro Ser Gly Leu Ser Asp Ala His Leu Ala Ala Ser Pro Pro
            500                 505                 510

Ser Leu Ala Leu Leu Ala Gly Ala Met Leu Leu Leu Ala Pro Ala
        515                 520                 525

Leu Tyr
```

```
<210> SEQ ID NO 4
<211> LENGTH: 503
<212> TYPE: PRT
<213> ORGANISM: Artificial Sequence
<220> FEATURE:
<223> OTHER INFORMATION: Synthetic polymer

<400> SEQUENCE: 4
```

Met Gln Gly Pro Trp Val Leu Leu Leu Leu Gly Leu Arg Leu Gln Leu
1               5                   10                  15

Ser Leu Gly Val Ile Pro Ala Glu Glu Asn Pro Ala Phe Trp Asn
            20                  25                  30

Arg Gln Ala Ala Glu Ala Leu Asp Ala Ala Lys Lys Leu Gln Pro Ile
            35                  40                  45

Gln Lys Val Ala Lys Asn Leu Ile Leu Phe Leu Gly Asp Gly Leu Gly
        50                  55                  60

Val Pro Thr Val Thr Ala Thr Arg Ile Leu Lys Gly Gln Lys Asn Gly
65                  70                  75                  80

Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
            100                 105                 110

Ala Thr Ala Thr Ala Tyr Leu Cys Gly Val Lys Ala Asn Phe Gln Thr
        115                 120                 125

Ile Gly Leu Ser Ala Ala Ala Arg Phe Asn Gln Cys Asn Thr Thr Arg
130                 135                 140

Gly Asn Glu Val Ile Ser Val Met Asn Arg Ala Lys Gln Ala Gly Lys
145                 150                 155                 160

Ser Val Gly Val Val Thr Thr Thr Arg Val Gln His Ala Ser Pro Ala
                165                 170                 175

Gly Thr Tyr Ala His Thr Val Asn Arg Asn Trp Tyr Ser Asp Ala Asp
            180                 185                 190

Met Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
            260                 265                 270

Met Gln Ala Ser Leu Asp Gln Ser Val Thr His Leu Met Gly Leu Phe
        275                 280                 285

Glu Pro Gly Asp Thr Lys Tyr Glu Ile His Arg Asp Pro Thr Leu Asp
        290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Arg Ile Asp His
                325                 330                 335

Gly His His Glu Gly Val Ala Tyr Gln Ala Leu Thr Glu Ala Val Met
            340                 345                 350

Phe Asp Asp Ala Ile Glu Arg Ala Gly Gln Leu Thr Ser Glu Glu Asp

```
                355                 360                 365
Thr Leu Thr Leu Val Thr Ala Asp His Ser His Val Phe Ser Phe Gly
    370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
            420                 425                 430

Ser Gly Ser Pro Asp Tyr Gln Gln Gln Ala Ala Val Pro Leu Ser Ser
        435                 440                 445

Glu Thr His Gly Gly Glu Asp Val Ala Val Phe Ala Arg Gly Pro Gln
    450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Gly Thr Thr Asp
            500

<210> SEQ ID NO 5
<211> LENGTH: 506
<212> TYPE: PRT
<213> ORGANISM: Artificial Sequence
<220> FEATURE:
<223> OTHER INFORMATION: Synthetic polymer

<400> SEQUENCE: 5

Met Gln Gly Ala Cys Val Leu Leu Leu Gly Leu His Leu Gln Leu
1               5                   10                  15

Ser Leu Gly Leu Ile Pro Ala Glu Glu Asn Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Arg Thr
        115                 120                 125

Ile Gly Val Ser Ala Ala Arg Tyr Asn Gln Cys Asn Thr Thr Arg
    130                 135                 140

Gly Asn Glu Val Thr Ser Val Ile Asn Arg Ala Lys Lys Ala Gly Lys
145                 150                 155                 160

Ala Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Lys Asn Gly Cys Gln Asp Ile Ala Ala Gln
        195                 200                 205

Leu Val Tyr Asn Met Asp Ile Asp Val Ile Leu Gly Gly Gly Arg Met
```

```
            210                 215                 220

Tyr Met Phe Pro Glu Gly Thr Pro Asp Pro Glu Tyr Pro Asp Asp Ala
225                 230                 235                 240

Ser Val Asn Gly Val Arg Lys Asp Lys Gln Asn Leu Val Gln Glu Trp
                245                 250                 255

Gln Ala Lys His Gln Gly Ala Gln Tyr Val Trp Asn Arg Thr Ala Leu
                    260                 265                 270

Leu Gln Ala Ala Asp Asp Ser Ser Val Thr His Leu Met Gly Leu Phe
                275                 280                 285

Glu Pro Ala Asp Met Lys Tyr Asn Val Gln Gln Asp His Thr Lys Asp
                290                 295                 300

Pro Thr Leu Ala Glu Met Thr Glu Ala Ala Leu Gln Val Leu Ser Arg
305                 310                 315                 320

Asn Pro Arg Gly Phe Tyr Leu Phe Val Glu Gly Gly Arg Ile Asp His
                    325                 330                 335

Gly His His Asp Gly Lys Ala Tyr Met Ala Leu Thr Glu Ala Ile Met
                340                 345                 350

Phe Asp Asn Ala Ile Ala Lys Ala Asn Glu Leu Thr Ser Glu Leu Asp
                355                 360                 365

Thr Leu Ile Leu Val Thr Ala Asp His Ser His Val Phe Ser Phe Gly
                370                 375                 380

Gly Tyr Thr Leu Arg Gly Thr Ser Ile Phe Gly Leu Ala Pro Gly Lys
385                 390                 395                 400

Ala Leu Asp Ser Lys Ser Tyr Thr Ser Ile Leu Tyr Gly Asn Gly Pro
                    405                 410                 415

Gly Tyr Ala Leu Gly Gly Gly Ser Arg Pro Asp Val Asn Gly Ser Thr
                420                 425                 430

Ser Glu Glu Pro Ser Tyr Arg Gln Gln Ala Ala Val Pro Leu Ala Ser
                435                 440                 445

Glu Thr His Gly Gly Glu Asp Val Ala Val Phe Ala Arg Gly Pro Gln
                450                 455                 460

Ala His Leu Val His Gly Val Gln Glu Glu Thr Phe Val Ala His Ile
465                 470                 475                 480

Met Ala Phe Ala Gly Cys Val Glu Pro Tyr Thr Asp Cys Asn Leu Pro
                    485                 490                 495

Ala Pro Ala Thr Ala Thr Ser Ile Pro Asp
                500                 505

<210> SEQ ID NO 6
<211> LENGTH: 503
<212> TYPE: PRT
<213> ORGANISM: Artificial Sequence
<220> FEATURE:
<223> OTHER INFORMATION: Synthetic polymer

<400> SEQUENCE: 6

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
                20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
        50                  55                  60

Val Pro Thr Val Thr Ala Thr Arg Ile Leu Lys Gly Gln Met Asn Gly
```

```
                65                  70                  75                  80
Lys Leu Gly Pro Glu Thr Pro Leu Ala Met Asp Gln Phe Pro Tyr Val
                        85                  90                  95

Ala Leu Ser Lys Thr Tyr Asn Val Asp Arg Gln Val Pro Asp Ser Ala
                100                 105                 110

Gly Thr Ala Thr Ala Tyr Leu Cys Gly Val Lys Gly Asn Tyr Lys Thr
                115                 120                 125

Ile Gly Val Ser Ala Ala Arg Tyr Asn Gln Cys Asn Thr Thr Ser
        130                 135                 140

Gly Asn Glu Val Thr Ser Val Met Asn Arg Ala Lys Lys Ala Gly Lys
145                 150                 155                 160

Ser Val Gly Val Val Thr Ser Arg Val Gln His Ala Ser Pro Ala
                        165                 170                 175

Gly Ala Tyr Ala His Thr Val Asn Arg Asn Trp Tyr Ser Asp Ala Asp
                180                 185                 190

Leu Pro Ala Asp Ala Gln Thr Tyr Gly Cys Gln Asp Ile Ala Thr Gln
                195                 200                 205

Leu Val Asn Asn Met Asp Ile Asp Val Ile Leu Gly Gly Gly Arg Met
        210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                        245                 250                 255

Gln Ala Lys His Gln Gly Ala Gln Tyr Val Trp Asn Arg Thr Glu Leu
                260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                        325                 330                 335

Gly His His Glu Gly Lys Ala Tyr Met Ala Leu Thr Asp Thr Val Met
                340                 345                 350

Phe Asp Asn Ala Ile Ala Lys Ala Asn Glu Leu Thr Ser Glu Leu Asp
        355                 360                 365

Thr Leu Ile Leu Ala Thr Ala Asp His Ser His Val Phe Ser Phe Gly
370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                        405                 410                 415

Gly Tyr Val Leu Gly Gly Gly Leu Arg Pro Asp Val Asn Asp Ser Ile
                420                 425                 430

Ser Glu Asp Pro Ser Tyr Arg Gln Gln Ala Ala Val Pro Leu Ser Ser
        435                 440                 445

Glu Ser His Gly Gly Glu Asp Val Ala Val Phe Ala Arg Gly Pro Gln
450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Pro
                        485                 490                 495
```

```
Ala Pro Ser Gly Leu Ser Asp
            500

<210> SEQ ID NO 7
<211> LENGTH: 508
<212> TYPE: PRT
<213> ORGANISM: Artificial Sequence
<220> FEATURE:
<223> OTHER INFORMATION: Synthetic polymer

<400> SEQUENCE: 7

Met Gln Trp Ala Cys Val Leu Leu Leu Gly Leu Trp Leu Gln Leu
1               5                   10                  15

Ser Leu Thr Phe Ile Pro Ala Glu Glu Asp Pro Ala Phe Trp Asn
                20                  25                  30

Arg Gln Ala Ala Gln Ala Leu Asp Val Ala Lys Lys Leu Gln Pro Ile
                35                  40                  45

Gln Thr Ala Ala Lys Asn Val Ile Leu Phe Leu Gly Asp Gly Met Gly
                50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                    85                  90                  95

Ala Leu Ser Lys Thr Tyr Asn Val Asp Arg Gln Val Pro Asp Ser Ala
                100                 105                 110

Gly Thr Ala Thr Ala Tyr Leu Cys Gly Val Lys Gly Asn Tyr Lys Thr
                115                 120                 125

Ile Gly Val Ser Ala Ala Arg Tyr Asn Gln Cys Asn Thr Thr Ser
        130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                    165                 170                 175

Gly Ala Tyr Ala His Thr Val Asn Arg Asn Trp Tyr Ser Asp Ala Asp
                180                 185                 190

Leu Pro Ala Asp Ala Gln Thr Tyr Gly Cys Gln Asp Ile Ala Thr Gln
                195                 200                 205

Leu Val Asn Asn Met Asp Ile Asp Val Ile Leu Gly Gly Gly Arg Met
        210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                    245                 250                 255

Gln Ala Lys His Gln Gly Ala Gln Tyr Val Trp Asn Arg Thr Glu Leu
                260                 265                 270

Leu Gln Ala Ala Asn Asp Pro Ser Val Thr His Leu Met Gly Leu Phe
        275                 280                 285

Glu Pro Ala Asp Met Lys Tyr Asn Val Gln Gln Asp Pro Thr Lys Asp
        290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                    325                 330                 335

Gly His His Glu Gly Lys Ala Tyr Met Ala Leu Thr Asp Thr Val Met
                340                 345                 350
```

```
Phe Asp Asn Ala Ile Ala Lys Ala Asn Glu Leu Thr Ser Glu Leu Asp
            355                 360                 365

Thr Leu Ile Leu Ala Thr Ala Asp His Ser His Val Phe Ser Phe Gly
        370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Leu Arg Pro Asp Val Asn Asp Ser Ile
                420                 425                 430

Ser Glu Asp Pro Ser Tyr Arg Gln Gln Ala Ala Val Pro Leu Ser Ser
            435                 440                 445

Glu Ser His Gly Gly Glu Asp Val Ala Val Phe Ala Arg Gly Pro Gln
        450                 455                 460

Ala His Leu Val His Gly Val Gln Glu Thr Phe Val Ala His Val
465                 470                 475                 480

Met Ala Phe Ala Gly Cys Val Glu Pro Tyr Thr Asp Cys Asn Leu Pro
                485                 490                 495

Ala Pro Ser Gly Leu Ser Asp Ala Ala His Leu Ala
            500                 505

<210> SEQ ID NO 8
<211> LENGTH: 754
<212> TYPE: PRT
<213> ORGANISM: Artificial Sequence
<220> FEATURE:
<223> OTHER INFORMATION: Synthetic polymer

<400> SEQUENCE: 8

Met Gln Gly Ala Cys Val Leu Leu Leu Gly Leu His Leu Gln Leu
1               5                   10                  15

Ser Leu Gly Leu Ile Pro Ala Glu Glu Glu Asn Pro Ala Phe Trp Asn
                20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
        50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Arg Thr
        115                 120                 125

Ile Gly Val Ser Ala Ala Ala Arg Tyr Asn Gln Cys Asn Thr Thr Arg
    130                 135                 140

Gly Asn Glu Val Thr Ser Val Ile Asn Arg Ala Lys Lys Ala Gly Lys
145                 150                 155                 160

Ala Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Lys Asn Gly Cys Gln Asp Ile Ala Ala Gln
        195                 200                 205
```

-continued

Leu Val Tyr Asn Met Asp Ile Asp Val Ile Leu Gly Gly Arg Met
    210                 215                 220

Tyr Met Phe Pro Glu Gly Thr Pro Asp Pro Glu Tyr Pro Asp Asp Ala
225                 230                 235                 240

Ser Val Asn Gly Val Arg Lys Asp Lys Gln Asn Leu Val Gln Glu Trp
                245                 250                 255

Gln Ala Lys His Gln Gly Ala Gln Tyr Val Trp Asn Arg Thr Ala Leu
            260                 265                 270

Leu Gln Ala Ala Asp Asp Ser Ser Val Thr His Leu Met Gly Leu Phe
        275                 280                 285

Glu Pro Ala Asp Met Lys Tyr Asn Val Gln Gln Asp His Thr Lys Asp
    290                 295                 300

Pro Thr Leu Ala Glu Met Thr Glu Ala Ala Leu Gln Val Leu Ser Arg
305                 310                 315                 320

Asn Pro Arg Gly Phe Tyr Leu Phe Val Glu Gly Gly Arg Ile Asp His
                325                 330                 335

Gly His His Asp Gly Lys Ala Tyr Met Ala Leu Thr Glu Ala Ile Met
            340                 345                 350

Phe Asp Asn Ala Ile Ala Lys Ala Asn Glu Leu Thr Ser Glu Leu Asp
        355                 360                 365

Thr Leu Ile Leu Val Thr Ala Asp His Ser His Val Phe Ser Phe Gly
    370                 375                 380

Gly Tyr Thr Leu Arg Gly Thr Ser Ile Phe Gly Leu Ala Pro Gly Lys
385                 390                 395                 400

Ala Leu Asp Ser Lys Ser Tyr Thr Ser Ile Leu Tyr Gly Asn Gly Pro
                405                 410                 415

Gly Tyr Ala Leu Gly Gly Gly Ser Arg Pro Asp Val Asn Gly Ser Thr
            420                 425                 430

Ser Glu Glu Pro Ser Tyr Arg Gln Gln Ala Ala Val Pro Leu Ala Ser
        435                 440                 445

Glu Thr His Gly Gly Glu Asp Val Ala Val Phe Ala Arg Gly Pro Gln
    450                 455                 460

Ala His Leu Val His Gly Val Gln Glu Glu Thr Phe Val Ala His Ile
465                 470                 475                 480

Met Ala Phe Ala Gly Cys Val Glu Pro Tyr Thr Asp Cys Asn Leu Pro
                485                 490                 495

Ala Pro Ala Thr Ala Thr Ser Ile Pro Asp Gly Gly Ser Gly Gly Ser
            500                 505                 510

Gly Gly Gly Gly Ser Gly Gly Gly Ser Glu Pro Lys Ser Cys Asp
        515                 520                 525

Lys Thr His Thr Cys Pro Pro Cys Pro Ala Pro Glu Leu Leu Gly Gly
    530                 535                 540

Pro Ser Val Phe Leu Phe Pro Pro Lys Pro Lys Asp Thr Leu Met Ile
545                 550                 555                 560

Ser Arg Thr Pro Glu Val Thr Cys Val Val Val Asp Val Ser His Glu
                565                 570                 575

Asp Pro Gln Val Lys Phe Asn Trp Tyr Val Asp Gly Val Gln Val His
            580                 585                 590

Asn Ala Lys Thr Lys Pro Arg Glu Gln Gln Tyr Asn Ser Thr Tyr Arg
        595                 600                 605

Val Val Ser Val Leu Thr Val Leu His Gln Asn Trp Leu Asp Gly Lys
    610                 615                 620

```
Glu Tyr Lys Cys Lys Val Ser Asn Lys Ala Leu Pro Ala Pro Ile Glu
625                 630                 635                 640

Lys Thr Ile Ser Lys Ala Lys Gly Gln Pro Arg Glu Pro Gln Val Tyr
            645                 650                 655

Thr Leu Pro Pro Ser Arg Glu Glu Met Thr Lys Asn Gln Val Ser Leu
        660                 665                 670

Thr Cys Leu Val Lys Gly Phe Tyr Pro Ser Asp Ile Ala Val Glu Trp
    675                 680                 685

Glu Ser Asn Gly Gln Pro Glu Asn Asn Tyr Lys Thr Thr Pro Pro Val
690                 695                 700

Leu Asp Ser Asp Gly Ser Phe Phe Leu Tyr Ser Lys Leu Thr Val Asp
705                 710                 715                 720

Lys Ser Arg Trp Gln Gln Gly Asn Val Phe Ser Cys Ser Val Met His
            725                 730                 735

Glu Ala Leu His Asn His Tyr Thr Gln Lys Ser Leu Ser Leu Ser Pro
            740                 745                 750

Gly Lys

<210> SEQ ID NO 9
<211> LENGTH: 751
<212> TYPE: PRT
<213> ORGANISM: Artificial Sequence
<220> FEATURE:
<223> OTHER INFORMATION: Synthetic polymer

<400> SEQUENCE: 9

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
            20                  25                  30

Arg Gln Ala Ala Gln Ala Leu Asp Val Ala Lys Lys Leu Gln Pro Ile
        35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
        115                 120                 125

Ile Gly Val Ser Ala Ala Arg Tyr Asn Gln Cys Asn Thr Thr Ser
130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
        195                 200                 205

Leu Val Asn Asn Met Asp Ile Asp Val Ile Leu Gly Gly Gly Arg Met
    210                 215                 220

Tyr Met Phe Pro Glu Gly Thr Pro Asp Pro Glu Tyr Pro Tyr Asp Val
```

```
            225                 230                 235                 240
Asn Gln Thr Gly Val Arg Lys Asp Lys Arg Asn Leu Val Gln Glu Trp
                245                 250                 255
Gln Ala Lys His Gln Gly Ala Gln Tyr Val Trp Asn Arg Thr Glu Leu
                260                 265                 270
Leu Gln Ala Ala Asn Asp Pro Ser Val Thr His Leu Met Gly Leu Phe
                275                 280                 285
Glu Pro Ala Asp Met Lys Tyr Asn Val Gln Gln Asp Pro Thr Lys Asp
                290                 295                 300
Pro Thr Leu Glu Glu Met Thr Glu Ala Ala Leu Gln Val Leu Ser Arg
305                 310                 315                 320
Asn Pro Gln Gly Phe Tyr Leu Phe Val Glu Gly Gly Arg Ile Asp His
                325                 330                 335
Gly His His Glu Gly Lys Ala Tyr Met Ala Leu Thr Asp Thr Val Met
                340                 345                 350
Phe Asp Asn Ala Ile Ala Lys Ala Asn Glu Leu Thr Ser Glu Leu Asp
                355                 360                 365
Thr Leu Ile Leu Ala Thr Ala Asp His Ser His Val Phe Ser Phe Gly
370                 375                 380
Gly Tyr Thr Leu Arg Gly Thr Ser Ile Phe Gly Leu Ala Pro Ser Lys
385                 390                 395                 400
Ala Ser Asp Asn Lys Ser Tyr Thr Ser Ile Leu Tyr Gly Asn Gly Pro
                405                 410                 415
Gly Tyr Val Leu Gly Gly Gly Leu Arg Pro Asp Val Asn Asp Ser Ile
                420                 425                 430
Ser Glu Asp Pro Ser Tyr Arg Gln Gln Ala Ala Val Pro Leu Ser Ser
                435                 440                 445
Glu Ser His Gly Gly Glu Asp Val Ala Val Phe Ala Arg Gly Pro Gln
                450                 455                 460
Ala His Leu Val His Gly Val Gln Glu Glu Thr Phe Val Ala His Val
465                 470                 475                 480
Met Ala Phe Ala Gly Cys Val Glu Pro Tyr Thr Asp Cys Asn Leu Pro
                485                 490                 495
Ala Pro Ser Gly Leu Ser Asp Gly Gly Ser Gly Gly Ser Gly Gly Gly
                500                 505                 510
Gly Ser Gly Gly Gly Ser Glu Pro Lys Ser Cys Asp Lys Thr His
                515                 520                 525
Thr Cys Pro Pro Cys Pro Ala Pro Glu Leu Leu Gly Gly Pro Ser Val
530                 535                 540
Phe Leu Phe Pro Pro Lys Pro Lys Asp Thr Leu Met Ile Ser Arg Thr
545                 550                 555                 560
Pro Glu Val Thr Cys Val Val Val Asp Val Ser His Glu Asp Pro Gln
                565                 570                 575
Val Lys Phe Asn Trp Tyr Val Asp Gly Val Gln Val His Asn Ala Lys
                580                 585                 590
Thr Lys Pro Arg Glu Gln Gln Tyr Asn Ser Thr Tyr Arg Val Val Ser
                595                 600                 605
Val Leu Thr Val Leu His Gln Asn Trp Leu Asp Gly Lys Glu Tyr Lys
                610                 615                 620
Cys Lys Val Ser Asn Lys Ala Leu Pro Ala Pro Ile Glu Lys Thr Ile
625                 630                 635                 640
Ser Lys Ala Lys Gly Gln Pro Arg Glu Pro Gln Val Tyr Thr Leu Pro
                645                 650                 655
```

```
Pro Ser Arg Glu Glu Met Thr Lys Asn Gln Val Ser Leu Thr Cys Leu
            660                 665                 670

Val Lys Gly Phe Tyr Pro Ser Asp Ile Ala Val Glu Trp Glu Ser Asn
            675                 680                 685

Gly Gln Pro Glu Asn Asn Tyr Lys Thr Thr Pro Pro Val Leu Asp Ser
            690                 695                 700

Asp Gly Ser Phe Phe Leu Tyr Ser Lys Leu Thr Val Asp Lys Ser Arg
705                 710                 715                 720

Trp Gln Gln Gly Asn Val Phe Ser Cys Ser Val Met His Glu Ala Leu
                725                 730                 735

His Asn His Tyr Thr Gln Lys Ser Leu Ser Leu Ser Pro Gly Lys
            740                 745                 750

<210> SEQ ID NO 10
<211> LENGTH: 539
<212> TYPE: PRT
<213> ORGANISM: Artificial Sequence
<220> FEATURE:
<223> OTHER INFORMATION: Synthetic polymer

<400> SEQUENCE: 10

Met Gln Trp Ala Cys Val Leu Leu Leu Gly Leu Trp Leu Gln Leu
1               5                   10                  15  Leu

Ser Leu Thr Phe Ile Pro Ala Glu Glu Glu Asp Pro Ala Phe Trp Asn
            20                  25                  30

Arg Gln Ala Ala Gln Ala Leu Asp Val Ala Lys Lys Leu Gln Pro Ile
            35                  40                  45

Gln Thr Ala Ala Lys Asn Val Ile Leu Phe Leu Gly Asp Gly Met Gly
    50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

Ala Leu Ser Lys Thr Tyr Asn Val Asp Arg Gln Val Pro Asp Ser Ala
            100                 105                 110

Gly Thr Ala Thr Ala Tyr Leu Cys Gly Val Lys Gly Asn Tyr Lys Thr
            115                 120                 125

Ile Gly Val Ser Ala Ala Ala Arg Tyr Asn Gln Cys Asn Thr Thr Ser
    130                 135                 140

Gly Asn Glu Val Thr Ser Val Met Asn Arg Ala Lys Lys Ala Gly Lys
145                 150                 155                 160

Ser Val Gly Val Val Thr Thr Ser Arg Val Gln His Ala Ser Pro Ala
                165                 170                 175

Gly Ala Tyr Ala His Thr Val Asn Arg Asn Trp Tyr Ser Asp Ala Asp
            180                 185                 190

Leu Pro Ala Asp Ala Gln Thr Tyr Gly Cys Gln Asp Ile Ala Thr Gln
            195                 200                 205

Leu Val Asn Asn Met Asp Ile Asp Val Ile Leu Gly Gly Gly Arg Met
    210                 215                 220

Tyr Met Phe Pro Glu Gly Thr Pro Asp Pro Glu Tyr Pro Tyr Asp Val
225                 230                 235                 240

Asn Gln Thr Gly Val Arg Lys Asp Lys Arg Asn Leu Val Gln Glu Trp
                245                 250                 255

Gln Ala Lys His Gln Gly Ala Gln Tyr Val Trp Asn Arg Thr Glu Leu
            260                 265                 270
```

-continued

Leu Gln Ala Ala Asn Asp Pro Ser Val Thr His Leu Met Gly Leu Phe
                275                 280                 285

Glu Pro Ala Asp Met Lys Tyr Asn Val Gln Gln Pro Thr Lys Asp
290                 295                 300

Pro Thr Leu Glu Glu Met Thr Glu Ala Ala Leu Gln Val Leu Ser Arg
305                 310                 315                 320

Asn Pro Gln Gly Phe Tyr Leu Phe Val Glu Gly Gly Arg Ile Asp His
                325                 330                 335

Gly His His Glu Gly Lys Ala Tyr Met Ala Leu Thr Asp Thr Val Met
                340                 345                 350

Phe Asp Asn Ala Ile Ala Lys Ala Asn Glu Leu Thr Ser Glu Leu Asp
                355                 360                 365

Thr Leu Ile Leu Ala Thr Ala Asp His Ser His Val Phe Ser Phe Gly
                370                 375                 380

Gly Tyr Thr Leu Arg Gly Thr Ser Ile Phe Gly Leu Ala Pro Ser Lys
385                 390                 395                 400

Ala Ser Asp Asn Lys Ser Tyr Thr Ser Ile Leu Tyr Gly Asn Gly Pro
                405                 410                 415

Gly Tyr Val Leu Gly Gly Gly Leu Arg Pro Asp Val Asn Asp Ser Ile
                420                 425                 430

Ser Glu Asp Pro Ser Tyr Arg Gln Gln Ala Ala Val Pro Leu Ser Ser
                435                 440                 445

Glu Ser His Gly Gly Glu Asp Val Ala Val Phe Ala Arg Gly Pro Gln
                450                 455                 460

Ala His Leu Val His Gly Val Gln Glu Glu Thr Phe Val Ala His Val
465                 470                 475                 480

Met Ala Phe Ala Gly Cys Val Glu Pro Tyr Thr Asp Cys Asn Leu Glu
                485                 490                 495

Val Leu Phe Gln Gly Pro Ala Pro Ala Gly Thr Thr Asp Ala Ala
                500                 505                 510

His Pro Gly Arg Ser Val Val Pro Ala Leu Leu Pro Leu Arg Ala Gly
                515                 520                 525

Thr Leu Leu Leu Glu Thr Ala Thr Ala Pro
                530                 535

<210> SEQ ID NO 11
<211> LENGTH: 534
<212> TYPE: PRT
<213> ORGANISM: Artificial Sequence
<220> FEATURE:
<223> OTHER INFORMATION: Synthetic polymer

<400> SEQUENCE: 11

Met Gln Trp Ala Cys Val Leu Leu Leu Gly Leu Trp Leu Gln Leu
1               5                   10                  15

Ser Leu Thr Phe Ile Pro Ala Glu Glu Glu Asp Pro Ala Phe Trp Asn
                20                  25                  30

Arg Gln Ala Ala Gln Ala Leu Asp Val Ala Lys Lys Leu Gln Pro Ile
                35                  40                  45

Gln Thr Ala Ala Lys Asn Val Ile Leu Phe Leu Gly Asp Gly Met Gly
                50                  55                  60

Val Pro Thr Val Thr Ala Thr Arg Ile Leu Lys Gly Gln Met Asn Gly
65                  70                  75                  80

Lys Leu Gly Pro Glu Thr Pro Leu Ala Met Asp Gln Phe Pro Tyr Val
                85                  90                  95

```
Ala Leu Ser Lys Thr Tyr Asn Val Asp Arg Gln Val Pro Asp Ser Ala
            100                 105                 110
Gly Thr Ala Thr Ala Tyr Leu Cys Gly Val Lys Gly Asn Tyr Lys Thr
        115                 120                 125
Ile Gly Val Ser Ala Ala Arg Tyr Asn Gln Cys Asn Thr Thr Ser
130                 135                 140
Gly Asn Glu Val Thr Ser Val Met Asn Arg Ala Lys Lys Ala Gly Lys
145                 150                 155                 160
Ser Val Gly Val Val Thr Thr Ser Arg Val Gln His Ala Ser Pro Ala
                165                 170                 175
Gly Ala Tyr Ala His Thr Val Asn Arg Asn Trp Tyr Ser Asp Ala Asp
            180                 185                 190
Leu Pro Ala Asp Ala Gln Thr Tyr Gly Cys Gln Asp Ile Ala Thr Gln
        195                 200                 205
Leu Val Asn Asn Met Asp Ile Asp Val Ile Leu Gly Gly Gly Arg Met
    210                 215                 220
Tyr Met Phe Pro Glu Gly Thr Pro Asp Pro Glu Tyr Pro Tyr Asp Val
225                 230                 235                 240
Asn Gln Thr Gly Val Arg Lys Asp Lys Arg Asn Leu Val Gln Glu Trp
                245                 250                 255
Gln Ala Lys His Gln Gly Ala Gln Tyr Val Trp Asn Arg Thr Glu Leu
            260                 265                 270
Leu Gln Ala Ala Asn Asp Pro Ser Val Thr His Leu Met Gly Leu Phe
        275                 280                 285
Glu Pro Ala Asp Met Lys Tyr Asn Val Gln Gln Asp Pro Thr Lys Asp
    290                 295                 300
Pro Thr Leu Glu Glu Met Thr Glu Ala Ala Leu Gln Val Leu Ser Arg
305                 310                 315                 320
Asn Pro Gln Gly Phe Tyr Leu Phe Val Glu Gly Gly Arg Ile Asp His
                325                 330                 335
Gly His His Glu Gly Lys Ala Tyr Met Ala Leu Thr Asp Thr Val Met
            340                 345                 350
Phe Asp Asn Ala Ile Ala Lys Ala Asn Glu Leu Thr Ser Glu Leu Asp
        355                 360                 365
Thr Leu Ile Leu Ala Thr Ala Asp His Ser His Val Phe Ser Phe Gly
    370                 375                 380
Gly Tyr Thr Leu Arg Gly Thr Ser Ile Phe Gly Leu Ala Pro Ser Lys
385                 390                 395                 400
Ala Ser Asp Asn Lys Ser Tyr Thr Ser Ile Leu Tyr Gly Asn Gly Pro
                405                 410                 415
Gly Tyr Val Leu Gly Gly Gly Leu Arg Pro Asp Val Asn Asp Ser Ile
            420                 425                 430
Ser Glu Asp Pro Ser Tyr Arg Gln Gln Ala Ala Val Pro Leu Ser Ser
        435                 440                 445
Glu Ser His Gly Gly Glu Asp Val Ala Val Phe Ala Arg Gly Pro Gln
    450                 455                 460
Ala His Leu Val His Gly Val Gln Glu Glu Thr Phe Val Ala His Val
465                 470                 475                 480
Met Ala Phe Ala Gly Cys Val Glu Pro Tyr Thr Asp Cys Asn Leu Ala
                485                 490                 495
Pro Pro Ala Gly Thr Thr Asp Ala Ala His Pro Ile Glu Gly Arg Ser
            500                 505                 510
```

Val Val Pro Ala Leu Leu Pro Leu Arg Ala Gly Thr Leu Leu Leu Leu
    515                 520                 525

Glu Thr Ala Thr Ala Pro
    530

<210> SEQ ID NO 12
<211> LENGTH: 1669
<212> TYPE: DNA
<213> ORGANISM: Artificial Sequence
<220> FEATURE:
<223> OTHER INFORMATION: Synthetic polymer

<400> SEQUENCE: 12

```
atgcaggggc cctgggtgct gctgctgctg ggcctgaggc tacagctctc cctgggcgtc      60
atcccaggta atgaggctcc ccaagctgtt ccacacacag gcacccccct cagccaggct     120
gacctgatct ctactctccc cctggccagc tgaggaggag aacccggcct tctggaaccg     180
ccaggcagct gaggccctgg atgctgccaa gaagctgcag cccatccaga aggtcgccaa     240
gaacctcatc ctcttcctgg gcgatgggtt ggggtgccc acggtgacag ccaccaggat     300
cctaaagggg cagaagaatg caaactggg gcctgagacg ccctggcca tggaccgctt     360
cccatacctg gctctgtcca agacatacaa tgtggacaga caggtgccag acagcgcagc     420
cacagccacg gcctacctgt gcggggtcaa ggccaacttc cagaccatcg gcttgagtgc     480
agccgcccgc tttaaccagt gcaacacgac acgcggcaat gaggtcatct ccgtgatgaa     540
ccgggccaag caagcaggaa agtcagtagg agtggtgacc accacacggg tgcagcacgc     600
ctcgccagcc ggcaccctacg cacacacagt gaaccgcaac tggtactcag atgctgacat     660
gcctgcctca gcccgccagg agggtgccaa ggacatcgcc actcagctca tctccaacat     720
ggacattgac gtgatccttg gcggaggccg caagtacatg tttcccatgg ggaccccaga     780
ccctgagtac ccagctgatg ccagccagaa tggaatcagg ctggacggga agaacctggt     840
gcaggaatgg ctggcaaagc accagggtgc ctggtatgtg tggaaccgca ctgagctcat     900
gcaggcgtcc ctggaccagt ctgtgaccca tctcatgggc ctctttgagc ccggagacac     960
gaaatatgag atccaccgag accccacact ggacccctcc ctgatggaga tgacagaggc    1020
tgccctgcgc ctgctgagca ggaaccccg cggcttctac ctctttgtgg agggcggccg    1080
catcgaccat ggtcatcatg agggtgtggc ttaccaggca ctcactgagg cggtcatgtt    1140
cgacgacgcc attgagaggg cgggccagct caccagcgag aggacacgc tgaccctcgt    1200
caccgctgac cactcccatg tcttctcctt tggtggctac accttgcgag ggagctccat    1260
cttcggggttg gcccccagca aggctcagga cagcaaagcc tacacgtcca tcctgtacgg    1320
caatggcccg ggctacgtgt tcaactcagg cgtgcgacca gacgtgaatg agagcgagag    1380
cgggagcccc gattaccagc agcaggcggc ggtgccctg tcgtccgaga cccacggagg    1440
cgaagacgtg gcggtgtttg cgcgcggccc gcaggcgcac ctggtgcatg tgtgcagga    1500
gcagagcttc gtagcgcatg tcatggcctt cgctgcctgt ctggagccct acacggcctg    1560
cgacctggcg cctcccgcct gcaccaccga cgccgcgcac ccagttgccg cgtcgctgcc    1620
actgctggcc gggaccctgc tgctgctggg ggcgtccgct gctccctga                1669
```

<210> SEQ ID NO 13
<211> LENGTH: 1671
<212> TYPE: DNA
<213> ORGANISM: Artificial Sequence
<220> FEATURE:
<223> OTHER INFORMATION: Synthetic polymer

<400> SEQUENCE: 13

```
atgcaggggc cctgggtgct gctgctgctg ggcctgaggc tacagctctc cctgggcgtc     60
atcccagctg aggaggagaa cccggccttc tggaaccgcc aggcagctga ggccctggat    120
gctgccaaga agctgcagcc catccagaag gtcgccaaga acctcatcct cttcctgggc    180
gatgggttgg gggtgcccac ggtgacagcc accaggatcc taaagggggca gaagaatggc    240
aaactggggc ctgagacgcc cctggccatg gaccgcttcc catacctggc tctgtccaag    300
acatacaatg tggacagaca ggtgccagac agcgcagcca cagccacggc ctacctgtgc    360
ggggtcaagg ccaacttcca gaccatcggc ttgagtgcag ccgcccgctt taaccagtgc    420
aacacgacac gcggcaatga ggtcatctcc gtgatgaacc gggccaagca agcaggaaag    480
tcagtaggag tggtgaccac cacacgggtg cagcacgcct cgccagccgg cacctacgca    540
cacacagtga accgcaactg gtactcagat gctgacatgc ctgcctcagc ccgccaggag    600
gggtgccagg acatcgccac tcagctcatc tccaacatgg acattgacgt gatccttggc    660
ggaggccgca agtacatgtt tcccatgggg accccagacc ctgagtaccc agctgatgcc    720
agccagaatg gaatcaggct ggacgggaag aacctggtgc aggaatggct ggcaaagcac    780
cagggtgcct ggtatgtgtg aaccgcact gagctcatgc aggcgtccct ggaccagtct    840
gtgacccatc tcatgggcct ctttgagccc ggagacacga aatatgagat ccaccgagac    900
cccacactgg accctccct gatggagatg acagaggctg ccctgcgcct gctgagcagg    960
aaccccgcg gcttctacct cttgtggag ggcggccgca tcgaccatgg tcatcatgag   1020
ggtgtggctt accaggcact cactgaggcg gtcatgttcg acgacgccat tgagagggcg   1080
ggccagctca ccagcgagga ggacacgctg accctcgtca ccgctgacca ctcccatgtc   1140
ttctcctttg gtggctacac cttgcgaggg agctccatct tcgggttggc ccccagcaag   1200
gctcaggaca gcaaagccta cacgtccatc ctgtacggca atggcccggg ctacgtgttc   1260
aactcaggcg tgcgaccaga cgtgaatgag agcgagagcg ggagccccga ttaccagcag   1320
caggcggcgg tgcccctgtc gtccgagacc cacggaggcg aagacgtggc ggtgtttgcg   1380
cgcggcccgc aggcgcacct ggtgcatggt gtgcaggagc agagcttcgt agcgcatgtc   1440
atggccttcg ctgcctgtct ggagccctac acggctgcg acctggcgcc tccgcctgc   1500
accaccgacg ccgcgcaccc agttgccgcg tcgctgccac tgctggccgg accctgctg   1560
ctgctggggg cgtccgctgc tccctgattt actaaaacct gaaataaaa ttgtaaaaca   1620
tcagtttgaa ggcctgactc tcagggtagt tcttttttaa ttctgggttt t          1671
```

<210> SEQ ID NO 14
<211> LENGTH: 1672
<212> TYPE: DNA
<213> ORGANISM: Artificial Sequence
<220> FEATURE:
<223> OTHER INFORMATION: Synthetic polymer

<400> SEQUENCE: 14

```
atgcagtggg cctgtgtgct gctgctgctg ggcctgtggc tacagctctc cctcaccttc     60
atcccaggta atcaggcggc tcccagcagc ccctactcac aggggcggct ctaggctgac    120
ctgaccaaca ctctccccct tgggcagctga ggaggaagac cccgccttct ggaaccgcca    180
ggcagcccag gcccttgatg tagccaagaa gttcagccg atccagacag ctgccaagaa    240
tgtcatcctc ttcttggggg atgggatggg ggtgcctacg gtgacagcca ctcggatcct    300
```

```
aaaggggcag atgaatggta agctgggacc tgagacaccc ctggccatgg accagttccc    360
atacgtggct ctgtccaaga catacaacgt ggacagacag gtgccagaca gcgcaggcac    420
tgccactgcc tacctgtgtg gggtcaaggg caactacaaa accattggtg taagtgcagc    480
cgcccgctac aaccagtgca acacaacaag tggcaatgag gtcacgtctg tgatgaaccg    540
ggccaagaaa gcaggaaagt cagtgggagt ggtgaccacc tccagggtgc agcatgcctc    600
cccagccggt gcttatgcac acacggtgaa ccgaaactgg tactcagatg ccgacctgcc    660
tgccgatgca cagacgtatg gctgccagga catcgccaca caactggtca caacatgga    720
tattgacgtg atcctgggtg aggccgaat gtacatgttt cctgagggga ccccggatcc    780
tgaataccca tacgatgtca atcagactgg agtccggaag acaagcgga atctggtgca    840
ggagtggcag gccaagcacc agggagccca gtatgtgtgg aaccgcacgg agctccttca    900
ggcagccaat gaccccagtg taacacacct catgggcctc tttgagccgg cagacatgaa    960
gtataatgtt cagcaagacc ccaccaagga cccgaccctg gaggagatga cggaggcggc   1020
cctgcaagtg ctgagcagga accccagggg cttctacctc ttcgtggagg aggccgcat   1080
tgaccacggt caccatgaag gcaaagctta tatggcactg actgatacag tcatgtttga   1140
caatgccatc gccaaggcta acgagctcac tagcgaactg acacgctga tccttgccac   1200
tgcagaccac tcccatgtct tctcttttgg tggctacaca ctgcgtggga cctccatttt   1260
cggtctggcc cccagcaagg cctcagacaa caagtcctac acctccatcc tctatgcaa   1320
tggccctggc tacgtgcttg gtgggggctt aaggcccgat gttaatgaca gcataagcga   1380
ggaccctcg taccggcagc aggcggccgt gccctgtct agtgagtccc acggggcga   1440
ggacgtggcg gtgttcgcgc gaggcccgca ggcgcacctg gtgcacggcg tgcaggagga   1500
gaccttcgtg gcgcacgtca tggcctttgc gggctgcgtg gagccctaca ccgactgcaa   1560
tctgccggcc ccctctggcc tctccgacgc gcgcacctg gcggccagcc gcccttcgct   1620
ggcgctgctg gccggggcga tgctgctgct gctggcgcct gccttgtact ga           1672

<210> SEQ ID NO 15
<211> LENGTH: 1869
<212> TYPE: DNA
<213> ORGANISM: Artificial Sequence
<220> FEATURE:
<223> OTHER INFORMATION: Synthetic polymer

<400> SEQUENCE: 15
atgcagtggg cctgtgtgct gctgctgctg ggcctgtggc tacagctctc cctcaccttc    60
atcccagctg aggaggaaga ccccgccttc tggaaccgcc aggcagccca ggcccttgat   120
gtagccaaga agttgcagcc gatccagaca gctgccaaga atgtcatcct cttcttgggg   180
gatgggatgg gggtgcctac ggtgacagcc actcggatcc taaaggggca gatgaatggt   240
aagctgggac ctgagacacc cctggccatg accagttccc atacgtggct ctgtccaag    300
acatacaacg tggacagaca ggtgccagac agcgcaggca ctgccactgc ctacctgtgt   360
ggggtcaagg gcaactacaa aaccattggt gtaagtgcag ccgcccgcta caaccagtgc   420
aacacaacaa gtggcaatga ggtcacgtct gtgatgaacc gggccaagaa agcaggaaag   480
tcagtgggag tggtgaccac ctccagggtg cagcatgcct cccagccgg tgcttatgca   540
cacacggtga accgaaactg gtactcagat gccgacctgc ctgccgatgc acagacgtat   600
ggctgccagg acatcgccac acaactggtc aacaacatgg atattgacgt gatcctgggt   660
ggaggccgaa tgtacatgtt tcctgagggg accccggatc ctgaataccc atacgatgtc   720
```

| | |
|---|---|
| aatcagactg gagtccggaa ggacaagcgg aatctggtgc aggagtggca ggccaagcac | 780 |
| cagggagccc agtatgtgtg gaaccgcacg gagctccttc aggcagccaa tgaccccagt | 840 |
| gtaacacacc tcatgggcct ctttgagccg gcagacatga agtataatgt tcagcaagac | 900 |
| cccaccaagg acccgaccct ggaggagatg acggaggcgg ccctgcaagt gctgagcagg | 960 |
| aaccccccagg gcttctacct cttcgtggag ggaggccgca ttgaccacgg tcaccatgaa | 1020 |
| ggcaaagctt atatggcact gactgataca gtcatgtttg acaatgccat cgccaaggct | 1080 |
| aacgagctca ctagcgaact ggacacgctg atccttgcca ctgcagacca ctcccatgtc | 1140 |
| ttctcttttg gtggctacac actgcgtggg acctccattt tcggtctggc ccccagcaag | 1200 |
| gcctcagaca acaagtccta cacctccatc ctctatggca atggccctgg ctacgtgctt | 1260 |
| ggtgggggct taaggcccga tgttaatgac agcataagcg aggacccctc gtaccggcag | 1320 |
| caggcggccg tgcccctgtc tagtgagtcc cacggggggcg aggacgtggc ggtgttcgcg | 1380 |
| cgaggcccgc aggcgcacct ggtgcacggc gtgcaggagg agaccttcgt ggcgcacgtc | 1440 |
| atggcctttg cgggctgcgt ggagccctac accgactgca atctgccggc ccctctggc | 1500 |
| ctctccgacg ccgcgcacct ggcggccagc ccgccttcgc tggcgctgct ggccggggcg | 1560 |
| atgctgctgc tgctggcgcc tgccttgtac tgaggggacc cggggggtggg gacacaggcc | 1620 |
| ccgcccctccc tgggaggcag gaagcagctc tcaaataaac tgttctaagt atgatacagg | 1680 |
| agtgatacat gtgtgaagag aagcccttag gtgggggcac agagtgtctg ggtgagggg | 1740 |
| gtcagggtca catcaggagg ttagggaggg gttgatgaag ggctgacgtt gagcaaagac | 1800 |
| caaaggcaac tcagaaggac agtggtgcag gactgggtgt ggtcagcagg gggactggtt | 1860 |
| gggggatcc | 1869 |

<210> SEQ ID NO 16
<211> LENGTH: 1259
<212> TYPE: DNA
<213> ORGANISM: Artificial Sequence
<220> FEATURE:
<223> OTHER INFORMATION: Synthetic polymer

<400> SEQUENCE: 16

| | |
|---|---|
| aaaaaacaag acaaagctga gatcagaaat gtcattgtga tgataggcga cggcatgggg | 60 |
| acgccttaca taagagccta ccgttccatg aaaaataacg gtgacacacc gaataacccg | 120 |
| aagttaacag aatttgaccg gaacctgaca ggcatgatga tgacgcatcc ggatgaccct | 180 |
| gactataata ttacagattc agcagcagcc ggaacagcat tagcgacagg cgttaagaca | 240 |
| tataacaatg caattggcgt cgataaaaac ggaaaaaaag tgaaatctgt acttgaagag | 300 |
| gccaaacagc aaggcaagtc aacagggctt gtcgccacgt ctgaaattaa ccacgccact | 360 |
| ccagccgcat atggcgccca caatgaatca cggaaaaaca tggaccaaat cgccaacagc | 420 |
| tatatggatg caagataaa aggcaaacat aaaatagacg tgctgctcgg cggcggaaaa | 480 |
| tcttatttta accgcaagaa cagaaacttg acaaggaat tcaaacaagc cggctacagc | 540 |
| tatgtgacaa ctaaacaagc attgaaaaaa aataagatc agcaggtgct cgggcttttc | 600 |
| gcagatggag ggcttgctaa agcgctcgac cgtgacagta aaacaccgtc tctcaaagac | 660 |
| atgacggttt cagcaattga tcgcctgaac caaaataaaa aaggatttt cttgatggtc | 720 |
| gaagggagcc agattgactg gcggccccat gacaatgata cagtaggagc catgagcgag | 780 |
| gttaaagatt ttgaacaggc ctataaagcc gcgattgaat ttgcgaaaaa agacaaacat | 840 |

```
acacttgtga ttgcaactgc tgaccataca accggcggct ttaccattgg cgcaaacggg    900
gaaaagaatt ggcacgcaga accgattctc tccgctaaga aaacacctga attcatggcc    960
aaaaaaatca ggaaggcaag ccggttaaag atgtgctcgc ccgctatgcc aatctgaaag   1020
tcacatctga agaaatcaaa agcgttgaag cagctgcaca ggctgacaaa agcaaagggg   1080
cctccaaagc catcatcaag attttaata cccgctccaa cagcggatgg acgagtaccg    1140
atcataccgg cgaagaagta ccggtatacg cgtacggccc cggaaaagaa aaattccgcg   1200
gattgattaa caatacggac caggcaaaca tcatatttaa gattttaaaa actggaaaa    1259
```

<210> SEQ ID NO 17
<211> LENGTH: 420
<212> TYPE: PRT
<213> ORGANISM: Artificial Sequence
<220> FEATURE:
<223> OTHER INFORMATION: Synthetic polymer

<400> SEQUENCE: 17

```
Lys Lys Gln Asp Lys Ala Glu Ile Arg Asn Val Ile Val Met Ile Gly
1               5                   10                  15

Asp Gly Met Gly Thr Pro Tyr Ile Arg Ala Tyr Arg Ser Met Lys Asn
            20                  25                  30

Asn Gly Asp Thr Pro Asn Asn Pro Lys Leu Thr Glu Phe Asp Arg Asn
        35                  40                  45

Leu Thr Gly Met Met Met Thr His Pro Asp Asp Pro Asp Tyr Asn Ile
    50                  55                  60

Thr Asp Ser Ala Ala Ala Gly Thr Ala Leu Ala Thr Gly Val Lys Thr
65                  70                  75                  80

Tyr Asn Asn Ala Ile Gly Val Asp Lys Asn Gly Lys Lys Val Lys Ser
                85                  90                  95

Val Leu Glu Glu Ala Lys Gln Gln Gly Lys Ser Thr Gly Leu Val Ala
            100                 105                 110

Thr Ser Glu Ile Asn His Ala Thr Pro Ala Ala Tyr Gly Ala His Asn
        115                 120                 125

Glu Ser Arg Lys Asn Met Asp Gln Ile Ala Asn Ser Tyr Met Asp Asp
    130                 135                 140

Lys Ile Lys Gly Lys His Lys Ile Asp Val Leu Leu Gly Gly Gly Lys
145                 150                 155                 160

Ser Tyr Phe Asn Arg Lys Asn Arg Asn Leu Thr Lys Glu Phe Lys Gln
                165                 170                 175

Ala Gly Tyr Ser Tyr Val Thr Thr Lys Gln Ala Leu Lys Lys Asn Lys
            180                 185                 190

Asp Gln Gln Val Leu Gly Leu Phe Ala Asp Gly Gly Leu Ala Lys Ala
        195                 200                 205

Leu Asp Arg Asp Ser Lys Thr Pro Ser Leu Lys Asp Met Thr Val Ser
    210                 215                 220

Ala Ile Asp Arg Leu Asn Gln Asn Lys Lys Gly Phe Phe Leu Met Val
225                 230                 235                 240

Glu Gly Ser Gln Ile Asp Trp Ala Ala His Asp Asn Asp Thr Val Gly
                245                 250                 255

Ala Met Ser Glu Val Lys Asp Phe Glu Gln Ala Tyr Lys Ala Ala Ile
            260                 265                 270

Glu Phe Ala Lys Lys Asp Lys His Thr Leu Val Ile Ala Thr Ala Asp
        275                 280                 285

His Thr Thr Gly Gly Phe Thr Ile Gly Ala Asn Gly Glu Lys Asn Trp
```

```
                290                 295                 300
His Ala Glu Pro Ile Leu Ser Ala Lys Lys Thr Pro Glu Phe Met Ala
305                 310                 315                 320

Lys Lys Ile Ser Glu Gly Lys Pro Val Lys Asp Val Leu Ala Arg Tyr
                325                 330                 335

Ala Asn Leu Lys Val Thr Ser Glu Glu Ile Lys Ser Val Glu Ala Ala
            340                 345                 350

Ala Gln Ala Asp Lys Ser Lys Gly Ala Ser Lys Ala Ile Ile Lys Ile
        355                 360                 365

Phe Asn Thr Arg Ser Asn Ser Gly Trp Thr Ser Thr Asp His Thr Gly
    370                 375                 380

Glu Glu Val Pro Val Tyr Ala Tyr Gly Pro Gly Lys Glu Lys Phe Arg
385                 390                 395                 400

Gly Leu Ile Asn Asn Thr Asp Gln Ala Asn Ile Ile Phe Lys Ile Leu
                405                 410                 415

Lys Thr Gly Lys
            420

<210> SEQ ID NO 18
<211> LENGTH: 16
<212> TYPE: PRT
<213> ORGANISM: Artificial Sequence
<220> FEATURE:
<223> OTHER INFORMATION: Synthetic polymer

<400> SEQUENCE: 18

Gly Gly Ser Gly Gly Ser Gly Gly Gly Ser Gly Gly Gly Gly Gly Ser
1               5                   10                  15

<210> SEQ ID NO 19
<211> LENGTH: 5
<212> TYPE: PRT
<213> ORGANISM: Artificial Sequence
<220> FEATURE:
<223> OTHER INFORMATION: Synthetic polymer

<400> SEQUENCE: 19

Gly Gly Gly Gly Ser
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic polymer

<400> SEQUENCE: 20

Gly Gly Gly Gly Ser Gly Gly Gly Gly Ser
1               5                   10

<210> SEQ ID NO 21
<211> LENGTH: 15
<212> TYPE: PRT
<213> ORGANISM: Artificial Sequence
<220> FEATURE:
<223> OTHER INFORMATION: Synthetic polymer

<400> SEQUENCE: 21

Gly Gly Gly Gly Ser Gly Gly Gly Gly Ser Gly Gly Gly Gly Ser
1               5                   10                  15
```

```
<210> SEQ ID NO 22
<211> LENGTH: 20
<212> TYPE: PRT
<213> ORGANISM: Artificial Sequence
<220> FEATURE:
<223> OTHER INFORMATION: Synthetic polymer

<400> SEQUENCE: 22

Gly Gly Gly Gly Ser Gly Gly Gly Ser Gly Gly Gly Gly Ser Gly
1               5                   10                  15

Gly Gly Gly Ser
            20

<210> SEQ ID NO 23
<211> LENGTH: 8
<212> TYPE: PRT
<213> ORGANISM: Artificial Sequence
<220> FEATURE:
<223> OTHER INFORMATION: Synthetic polymer

<400> SEQUENCE: 23

Gly Gly Gly Gly Gly Gly Gly Gly
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic polymer

<400> SEQUENCE: 24

Gly Gly Gly Gly Gly Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic polymer

<400> SEQUENCE: 25

Glu Ala Ala Ala Lys
1               5

<210> SEQ ID NO 26
<211> LENGTH: 10
<212> TYPE: PRT
<213> ORGANISM: Artificial Sequence
<220> FEATURE:
<223> OTHER INFORMATION: Synthetic polymer

<400> SEQUENCE: 26

Glu Ala Ala Ala Lys Glu Ala Ala Ala Lys
1               5                   10

<210> SEQ ID NO 27
<211> LENGTH: 15
<212> TYPE: PRT
<213> ORGANISM: Artificial Sequence
<220> FEATURE:
<223> OTHER INFORMATION: Synthetic polymer

<400> SEQUENCE: 27

Glu Ala Ala Ala Lys Glu Ala Ala Ala Lys Glu Ala Ala Ala Lys
1               5                   10                  15
```

<210> SEQ ID NO 28
<211> LENGTH: 12
<212> TYPE: PRT
<213> ORGANISM: Artificial Sequence
<220> FEATURE:
<223> OTHER INFORMATION: Synthetic polymer

<400> SEQUENCE: 28

Ala Glu Ala Ala Ala Lys Glu Ala Ala Ala Lys Ala
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Synthetic polymer

<400> SEQUENCE: 29

Ala Glu Ala Ala Ala Lys Glu Ala Ala Ala Lys Glu Ala Ala Ala Lys
1               5                   10                  15

Ala

<210> SEQ ID NO 30
<211> LENGTH: 22
<212> TYPE: PRT
<213> ORGANISM: Artificial Sequence
<220> FEATURE:
<223> OTHER INFORMATION: Synthetic polymer

<400> SEQUENCE: 30

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 31
<211> LENGTH: 27
<212> TYPE: PRT
<213> ORGANISM: Artificial Sequence
<220> FEATURE:
<223> OTHER INFORMATION: Synthetic polymer

<400> SEQUENCE: 31

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 32
<211> LENGTH: 12
<212> TYPE: PRT
<213> ORGANISM: Artificial Sequence
<220> FEATURE:
<223> OTHER INFORMATION: Synthetic polymer

<400> SEQUENCE: 32

Ala Glu Ala Ala Ala Lys Glu Ala Ala Ala Lys Ala
1               5                   10

<210> SEQ ID NO 33
<211> LENGTH: 46
<212> TYPE: PRT
<213> ORGANISM: Artificial Sequence

```
<220> FEATURE:
<223> OTHER INFORMATION: Synthetic polymer

<400> SEQUENCE: 33

Ala Glu Ala Ala Ala Lys Glu Ala Ala Lys Glu Ala Ala Ala Lys
1               5                   10                  15

Glu Ala Ala Lys Ala Leu Glu Ala Glu Ala Ala Lys Glu Ala
            20                  25                  30

Ala Ala Lys Glu Ala Ala Ala Lys Glu Ala Ala Lys Ala
        35                  40                  45

<210> SEQ ID NO 34
<211> LENGTH: 5
<212> TYPE: PRT
<213> ORGANISM: Artificial Sequence
<220> FEATURE:
<223> OTHER INFORMATION: Synthetic polymer

<400> SEQUENCE: 34

Pro Ala Pro Ala Pro
1               5

<210> SEQ ID NO 35
<211> LENGTH: 18
<212> TYPE: PRT
<213> ORGANISM: Artificial Sequence
<220> FEATURE:
<223> OTHER INFORMATION: Synthetic polymer

<400> SEQUENCE: 35

Lys Glu Ser Gly Ser Val Ser Ser Glu Gln Leu Ala Gln Phe Arg Ser
1               5                   10                  15

Leu Asp

<210> SEQ ID NO 36
<211> LENGTH: 14
<212> TYPE: PRT
<213> ORGANISM: Artificial Sequence
<220> FEATURE:
<223> OTHER INFORMATION: Synthetic polymer

<400> SEQUENCE: 36

Glu Gly Lys Ser Ser Gly Ser Gly Ser Glu Ser Lys Ser Thr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic polymer

<400> SEQUENCE: 37

Gly Ser Ala Gly Ser Ala Ala Gly Ser Gly Glu Phe
1               5                   10
```

What is claimed is:

1. A formulation in the form of a tablet comprising:
   42-48% by an intestinal weight alkaline phosphatase (AP)-based agent, wherein the AP-based agent comprises an amino acid sequence of at least 95% sequence identity with the amino acid sequence set forth in SEQ ID NOs: 2, 3, 5, 6 or 7 and wherein activity of the intestinal alkaline phosphatase is maintained at least at 60% until 36 weeks of storage;
   42-48% by weight sugar;
   7-13% by weight buffer salts; and
   0.5-1.5% by weight magnesium stearate.

2. The formulation of claim 1, further comprising an enteric coating.

3. The formulation of claim 2, wherein the enteric coating comprises Eudragit L 30 D 55 (poly(methacrylic acid-ethyl acrylate copolymer) 1:1).

4. The formulation of claim 1, further comprising two coatings.

5. The formulation of claim 4, wherein the first coating comprises a hydroxypropyl cellulose (HPC) subcoat and the second coating comprises an enteric coating.

6. The formulation of claim 5, wherein the enteric coating comprises Eudragit L 30 D 55 (poly(methacrylic acid-ethyl acrylate copolymer) 1:1).

7. The formulation of claim 1 comprising:
45% by weight AP-based agent;
45% by weight sugar;
10% by weight buffer salts; and
1% by weight magnesium stearate.

8. The formulation of claim 7, further comprising an enteric coating.

9. The formulation of claim 8, wherein the enteric coating comprises Eudragit L 30 D 55 (poly(methacrylic acid-ethyl acrylate copolymer) 1:1).

10. The formulation of claim 7, further comprising two coatings.

11. The formulation of claim 10, wherein the first coating comprises a HPC subcoat and the second coating comprises an enteric coating.

12. The formulation of claim 11, wherein the enteric coating comprises Eudragit L 30 D 55 (poly(methacrylic acid-ethyl acrylate copolymer) 1:1).

13. The formulation of claim 1, wherein the AP-based agent comprises an amino acid sequence having at least 95% sequence identity with the amino acid sequence set forth in SEQ ID NO: 2.

14. The formulation of claim 1, wherein at least 75% of the AP-based agent is released within 15 minutes in pH of 4-5.

15. The formulation of claim 1, wherein the sugar is lactose.

16. The formulation of claim 1, wherein the buffer salts are selected from Tris, MgCl, and $ZnSO_4$.

* * * * *